United States Patent
Chang et al.

(10) Patent No.: US 10,322,993 B2
(45) Date of Patent: Jun. 18, 2019

(54) WATER-SOLUBLE UV-ABSORBING COMPOUNDS AND USES THEREOF

(71) Applicant: Novartis AG, Basel (CH)

(72) Inventors: Frank Chang, Cumming, GA (US); Ryan DeSousa, Atlanta, GA (US); Troy Vernon Holland, Suwanee, GA (US); Walter R. Laredo, Fort Worth, TX (US)

(73) Assignee: Novartis AG, Basel (CH)

( * ) Notice: Subject to any disclaimer, the term of this patent is extended or adjusted under 35 U.S.C. 154(b) by 207 days.

(21) Appl. No.: 15/352,132

(22) Filed: Nov. 15, 2016

(65) Prior Publication Data

US 2017/0158611 A1    Jun. 8, 2017

Related U.S. Application Data

(60) Provisional application No. 62/261,925, filed on Dec. 2, 2015.

(51) Int. Cl.

| | |
|---|---|
| *C07D 249/20* | (2006.01) |
| *C07C 225/22* | (2006.01) |
| *C07C 225/10* | (2006.01) |
| *C08F 116/06* | (2006.01) |
| *G02B 1/04* | (2006.01) |
| *G02C 7/04* | (2006.01) |
| *G02C 7/10* | (2006.01) |
| *B29D 11/00* | (2006.01) |

(52) U.S. Cl.
CPC ...... *C07C 225/22* (2013.01); *B29D 11/00038* (2013.01); *C07C 225/10* (2013.01); *C07D 249/20* (2013.01); *C08F 116/06* (2013.01); *G02B 1/043* (2013.01); *G02C 7/049* (2013.01); *G02C 7/108* (2013.01)

(58) Field of Classification Search
CPC ..................................................... C07D 249/20
See application file for complete search history.

(56) References Cited

U.S. PATENT DOCUMENTS

| 4,444,711 A | 4/1984 | Schad |
|---|---|---|
| 4,460,534 A | 7/1984 | Boehm et al. |

(Continued)

FOREIGN PATENT DOCUMENTS

| EP | 0314620 A1 | 5/1989 |
|---|---|---|
| EP | 0274844 B1 | 11/1991 |

(Continued)

OTHER PUBLICATIONS

William R. Brown and Frederick A. Mason, The Blue Sodium Salt of Rhodamine-B and some Related Substances, Journal of the Chemical Society, Jan. 1, 1933, pp. 1264-1269.

(Continued)

*Primary Examiner* — Michael F Pepitone
(74) *Attorney, Agent, or Firm* — Jian Zhou

(57) ABSTRACT

Described herein are dimethyl acetal-containing UV-absorbing compounds and their uses in preparing UV-absorbing polyvinyl alcohol prepolymers suitable for producing UV-absorbing contact lenses capable of blocking ultra-violet ("UV") radiation and optionally (but preferably) violet radiation with wavelengths from 380 nm to 440 nm, thereby protecting eyes to some extent from damages caused by UV radiation and potentially from violet radiation. This invention also provides a UV-absorbing polyvinyl alcohol prepolymer.

11 Claims, 2 Drawing Sheets

(56) References Cited

U.S. PATENT DOCUMENTS

| | | | |
|---|---|---|---|
| 4,528,311 | A | 7/1985 | Beard et al. |
| 4,612,358 | A | 9/1986 | Besecke et al. |
| 4,716,234 | A | 12/1987 | Dunks et al. |
| 5,124,723 | A | 6/1992 | Laver |
| 5,190,565 | A | 3/1993 | Berenbaum et al. |
| 5,508,317 | A | 4/1996 | Müller |
| 5,583,163 | A | 12/1996 | Müller |
| 5,789,464 | A | 8/1998 | Müller |
| 5,843,346 | A | 12/1998 | Morrill |
| 5,849,810 | A | 12/1998 | Müller |
| 5,894,002 | A | 4/1999 | Boneberger et al. |
| 5,925,787 | A | 7/1999 | Taylor et al. |
| 6,303,687 | B1 | 10/2001 | Müller |
| 6,627,124 | B1 | 9/2003 | Herbrechtsmeier et al. |
| 6,800,225 | B1 | 10/2004 | Hagmann et al. |
| 7,384,590 | B2 | 6/2008 | Kelly et al. |
| 7,387,759 | B2 | 6/2008 | Kelly et al. |
| 7,803,359 | B1 | 9/2010 | Jinkerson et al. |
| 7,884,228 | B1 | 2/2011 | Laredo |
| 7,947,849 | B2 | 5/2011 | Laredo |
| 8,088,313 | B2 | 1/2012 | Hagmann et al. |
| 8,153,703 | B2 | 4/2012 | Laredo |
| 8,207,244 | B2 | 6/2012 | Laredo |
| 8,232,326 | B2 | 7/2012 | Laredo |
| 8,262,947 | B2 | 9/2012 | Laredo |
| 8,262,948 | B2 | 9/2012 | Laredo et al. |
| 8,329,775 | B2 | 12/2012 | Laredo |
| 8,475,691 | B2 | 7/2013 | Laredo |
| 8,585,938 | B1 | 11/2013 | Jinkerson et al. |
| 2009/0275717 | A1 | 11/2009 | Hung et al. |
| 2014/0004061 | A1 | 1/2014 | Levins et al. |
| 2014/0004063 | A1 | 1/2014 | Daly |
| 2016/0357031 | A1 | 12/2016 | Holland et al. |

FOREIGN PATENT DOCUMENTS

| | | |
|---|---|---|
| EP | 0632329 A1 | 1/1995 |
| EP | 0915914 B1 | 3/2004 |
| EP | 2523943 B1 | 11/2014 |
| WO | 8800942 A2 | 2/1988 |
| WO | 2004052837 A2 | 6/2004 |
| WO | 2010060698 A2 | 6/2010 |
| WO | 2013055746 A1 | 4/2013 |

OTHER PUBLICATIONS

Alan J. McAlees, Robert McCrindle, and David W. Sneddon, Hydrogenation of Substituted Phthalic Anhydrides over Palladium, Journal of the Chemical Society, Jan. 1, 1977, pp. 2030-2036.

Peter J. Waters and Neil A. Evans, The Effect of Phenylbenzotriazole Derivatives on the Photoyellowing of Wool, Textile Research Journal, May 1978, pp. 251-255, Melbourne, Australia.

I. H. Leaver, P. J. Waters, and N. A. Evans, Dual Role of a Hydroxyphenylbenzotriazole UV Absorber in the Photooxidation of Wool, Journal of Polymer Science: Polymer Chemistry Edition, vol. 17, (1979) pp. 1531-1541, Melbourne, Australia.

Takashi Umeda, Tadao Nakaya, and Minoru Imoto, The Convenient Preparation of a Vinyl Monomer Containing a Phospholipid Analogue, Makromol. Chem., Rapid Commun. 3, pp. 457-459 (1982), Osaka, Japan.

D. B. Dess and J. C. Martin, Readily Accessible 12-I-5(1) Oxidant for the Conversion of Primary and Secondary Alcohols to Aldehydes and Ketones, Journal of Organic Chemistry, vol. 48, pp. 4155-4156 (1983), University of Illinois, Urbana, Illinois, USA.

N. A. Evans, J. Rosevear, P. J. Waters, and J. F. K. Wilshire, Photoprotection of Wool with Sulfonated 2-(2'-Hydroxyaryl)-2H-benzotriazoles, Polymer Degradation and Stability 14 (1986) pp. 263-284, Parkville Victoria 3052, Australia.

Sylvain Brunel, Yves Chevalier and Pierre Le Perchec, Synthesis of New Zwitterionic Surfactants with Improved Solubility in Water, Tetrahedron vol. 45, No. 11, pp. 3363-3370, (1989). Laboratorire des Materiaux Organiques, CNRS, BP 24, 69390 Vernaison, France.

Jochen Rieker, Elke Lemmert-Schmitt, Gernot Goeller, Manfred Roessler, Guido J. Stueber, Heike Schettler, Horst E.A Kramer, John J. Stezowski, Helga Hoier, Sonja Henkel, Armin Schmidt, Helmut Port, Martin Wiechmann, Jean Rody, Gerhard Rytz, Mario Slongo, and Jean-Luc Birbaum, Ultraviolet Stabilizers of the 2-(Hydroxyphenyl) benzotriazole Class. Influence of Substituents on Structure and Spectra, Journal of Physical Chemistry, vol. 96, No. 25, (1992), pp. 10225-10234.

Vandana Srivastava, Amita Tandon and Suprabhat Ray, Convenient and Selective Acetylations of Phenols, Amines and Alcohols, Synthetic Communications, 22(18), pp. 2703-2710 (1992). Lucknow, India.

Ahmed F. Abdel-Magid, Kenneth G. Carson, Bruce D. Harris, Cynthia A. Maryanoff, and Rekha D. Shah, Reductive Amination of Aldehydes and Ketones with Sodium Triacetoxyborohydride. Studies on Direct and Indirect Reductive Amination Procedures, Journal of Organic Chemistry, 61(11) (1996), pp. 3849-3862, Spring House, Pennsylvania.

Jeffrey A. Robl, Chong-Qing Sun, Jay Stevenson, Denis E. Ryono, Ligaya M. Simpkins, Maria P. Cimarusti, Tamara Dejneka, William A. Slusarchyk, Sam Chao, Leslie Stratton, Raj N. Misra, Mark S. Bednarz, Magdi M. Asaad, Hong Son Cheung, Benoni E. Abboa-Offei, Patricia L. Smith, Parker D. Mathers, Maxine Fox, Thomas R. Schaeffer, Andrea A. Seymour, and Nick C. Trippodo, Dual Metalloprotease Inhibitors: Mercaptoacetyl-Based Fused Heterocyclic Dipeptide Mimetics as Inhibitors of Angiotensin-Converting Enzme and Neutral Endopeptidase, Journal of Medicinal Chemistry, vol. 40, pp. 1570-1577 (1997), American Chemical Society.

J. Carsten Pieck, David Kuch, Friederike Grolle, Uwe Linne, Clemens Haas, and Thomas Carell, PNA-Based Reagents for the Direct and Site-Specific Synthesis of Thymine Dimer Lesions in Genomic DNA, Journal of American Chemical Society, (2006), 128, pp. 1404-1405, Munich, Germany.

Marcos Zayat, Pilar Garcia-Parejo and David Levy, Preventing UV-light damage of light sensitive materials using a highly protective UV-absorbing coating, Chemical Society Reviews, (2007), 36, pp. 1270-1281.

K. El-Tahlawy, K. El-Nagar, and A. G. Elhendawy, Cyclodextrin-4 Hydroxy benzophenone inclusion complex for UV protective cotton fabric, The Journal of the Textile Institute, 98:5, (2007) pp. 453-462, Egypt.

Renata Farkas, Virginie Lhiaubet-Vallet, Jordi Corbera, Mercedesz Törincsi, Olga Gorchs, Carles Trullas, Oscar Jiménez, Miguel A. Miranda, and Lajos Novak, Synthesis of New 2-(2'-Hydroxyaryl)benzotriazoles and Evaluation of Their Photochemical Behavior as Potential UV-Filters, Molecules (2010), 15, pp. 6205-6216.

Wei Ma, Xue Jiang, Yong Liu, Bing Tao Tang, Shu Fen Zhang, Synthesis of a novel water-soluble polymeric UV-absorber for cotton, Chinese Chemical Letters 22 (2011) pp. 1489-1491, Dalian, China.

Prasad B. Sambarkar and Anand C. Patil, Synthesis of amides from acid and aminc using coupling reagents, Journal of Curr Pharm Res, (2012), pp. 22-24, India.

Joseph B. Edson, Clay S. Macomber, Bryan S. Pivovar and James M. Boncella, Hydroxide based decomposition pathways of alkyltrimethylammonium cations, Journal of Membrane Science 399-400 (2012) pp. 49-59.

G. Buchi and Steven M. Weinreb, Total Syntheses of Aflatoxins M1 and G1 and an Improved Synthesis of Aflatoxin B1, Journal of the American Chemical Society, 93:3, Feb. 10, 1971, pp. 746-752.

WATER-SOLUBLE UV-ABSORBING COMPOUNDS AND USES THEREOF

This application claims the benefits under 35 USC § 119 (e) of U.S. provisional application No. 62/261,925 filed Dec. 2, 2015, incorporated by reference in its entirety.

This invention is related to water-soluble dimethyl acetal-containing compounds capable of absorbing ultra-violet (UV) radiation and optionally high-energy-violet (HEVL) radiation and their uses for producing water-soluble actinically-crosslinkable polyvinyl alcohols capable of absorbing UV and optionally HEVL radiations. In addition, the invention provides a method for making hydrogel contact lenses capable of blocking ultra-violet ("UV") radiation and optionally (but preferably) violet radiation with wavelengths from 380 nm to 440 nm.

BACKGROUND

Most commercially-available non-silicone hydrogel contact lenses are produced according to a conventional cast molding technique involving use of disposable plastic molds and a mixture of vinylic monomers and crosslinking agents. There are several disadvantages with the conventional cast-molding technique. For example, a traditional cast-molding manufacturing process often includes lens extraction in which unpolymerized monomers must be removed from the lenses by using an organic solvent. Use of organic solvents can be costly and is not environmentally friendly. In addition, disposable plastic molds inherently have unavoidable dimensional variations, because, during injection-molding of plastic molds, fluctuations in the dimensions of molds can occur as a result of fluctuations in the production process (temperatures, pressures, material properties), and also because the resultant molds may undergo non-uniformly shrinking after the injection molding. These dimensional changes in the mold may lead to fluctuations in the parameters of contact lenses to be produced (peak refractive index, diameter, basic curve, central thickness etc.) and to a low fidelity in duplicating complex lens design.

The above described disadvantages encountered in a conventional cast-molding technique can be overcome by using the so-called Lightstream Technology™ (CIBA Vision), which involves (1) a lens-forming composition being substantially free of monomers and comprising a substantially-purified, water-soluble prepolymer with ethylenically-unsaturated groups, (2) reusable molds produced in high precision, and (3) curing under a spatial limitation of actinic radiation (e.g., UV), as described in U.S. Pat. Nos. 5,508,317, 5,583,163, 5,789,464, 5,849,810, 6,800,225, and 8,088,313. Lenses produced according to the Lightstream Technology™ can have high consistency and high fidelity to the original lens design, because of use of reusable, high precision molds. In addition, contact lenses with high quality can be produced at relatively lower cost due to the short curing time, a high production yield, and free of lens extraction and in an environmentally friendly manner because of use of water as solvent for preparing lens formulations.

However, the Lightstream Technology™ has not been applied to make contact lenses capable of absorbing ultra-violet (UV) lights (between 280 nm and 380 nm) and optionally high-energy violet lights (HEVL) (between 380 nm and 440 nm), largely because of the lack of water-soluble polymerizable UV-absorbers which can be incorporated into the polymer matrix of a contact lens made from a water-based lens formulation. Examples of known polymerizable UV-absorbers include Norbloc 7966 (2-(2'-hydroxy-5'-methacryloxyethylphenyl)benzotriazole), 4-acryloylethoxy-2-hydroxybenzophone, 2-(2-hydroxy-5-methacrylamidophenyl)-5-methoxybenzotriazole (UV6), 2-Hydroxy-4-methacryloyloxybenzophenone (UV7), 2-(2'-hydroxy-5'-acryloylpropyl-3'-tert-butyl-phenyl)-5-methoxy-2H-benzotriazole (UV16A), and other benzotriazole-containing UV-absorbing vinyl monomers described in U.S. Pat. Nos. 4,612,358, 4,528,311, and 7,803,359 (herein incorporated by reference in their entireties). Examples of UV/HEVL include 2-(5-Chloro-2H-Benzotriazol-2-yl)-6-(1,1-dimethylethyl)-4-ethenylphenol and 2-(1,1-dimethylethyl)-4-[3-(4-ethenylphenyl)methoxy]propoxy-6-(5-methoxy-2H-benzotriazol-2-yl)-phenol. Additional examples of UV/HEVL absorbers disclosed in U.S. Pat. Nos. 8,153,703, 8,232,326, 4,716,234, and 8,585,938 (herein incorporated by references in their entireties). But, those available UV-absorbers and UV/HEVL-absorbers are insoluble in water and cannot be used in the production of contact lenses from an aqueous lens formulation according to the Lightstream Technology™.

Therefore, there are still needs for a new water-soluble UV absorber or a new water-soluble UV/HEVL absorber for making UV-absorbing or UV/HEVL-absorbing contact lenses from an aqueous lens formulation according to the Lightstream Technology™.

SUMMARY

In one aspect, the invention provides an UV-absorbing reactive compound comprising a moiety of benzophenone or benzotriazole and a dimethyl acetal or diethyl acetal group.

In another aspect, the invention provides a water-soluble, actinically-crosslinkable polyvinyl alcohol prepolymer comprising ethylenically unsaturated groups and UV-absorbing moieties derived from an UV-absorbing reactive compound of the invention.

In a further aspect, the invention provides a method for producing UV-absorbing contact lenses from an aqueous lens formulation comprising at least one water-soluble, actinically-crosslinkable polyvinyl alcohol prepolymer of the invention.

The invention provides in a still further aspect hydrogel contact lenses obtained according to a method of the invention.

DETAILED DESCRIPTION

Figure 1:
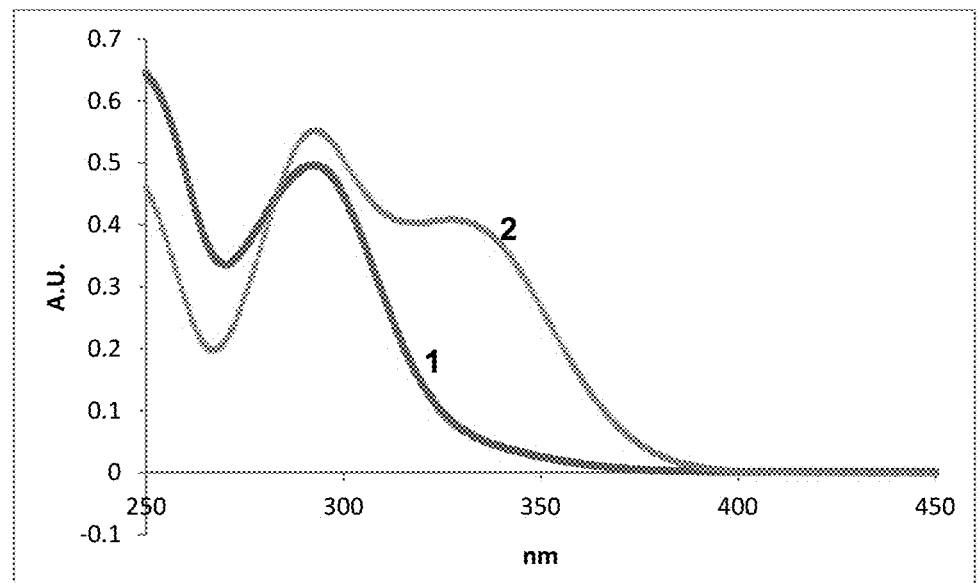
FIG. 1 shows the UV spectrum of a preferred water-soluble UV absorber of the invention in phosphate buffer (pH~7, 12.5 mM phosphate in 1:1 Water:n-propanol).

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well-known and commonly employed in the art.

"About" as used herein means that a number referred to as "about" comprises the recited number plus or minus 1-10% of that recited number.

"Optional" or "optionally" means that the subsequently described event or circumstance can or cannot occur, and that the description includes instances where the event or circumstance occurs and instances where it does not.

A "contact Lens" refers to a structure that can be placed on or within a wearer's eye. A contact lens can correct, improve, or alter a user's eyesight, but that need not be the case.

As used in this application, the term "hydrogel" or "hydrogel material" refers to a crosslinked polymeric material which is insoluble in water, but can hold at least 10 percent by weight of water in its three-dimensional polymer networks (i.e., polymer matrix) when it is fully hydrated.

A "vinylic monomer" refers to a compound that has one sole ethylenically-unsaturated group.

The term "soluble", in reference to a compound or material in a solvent, means that the compound or material can be dissolved in the solvent to give a solution with a concentration of at least about 0.1% by weight at room temperature (i.e., from about 20° C. to about 30° C.).

The term "insoluble", in reference to a compound or material in a solvent, means that the compound or material can be dissolved in the solvent to give a solution with a concentration of less than 0.005% by weight at room temperature (as defined above).

The term "ethylenically unsaturated group" is employed herein in a broad sense and is intended to encompass any groups containing at least one >C=C< group. Exemplary ethylenically unsaturated groups include without limitation (meth)acryloyl

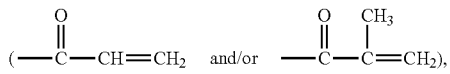

allyl, vinyl (—CH=CH$_2$), 1-methylethenyl

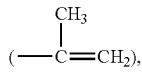

styrenyl, or the likes.

The term "(meth)acrylamide" refers to methacrylamide and/or acrylamide.

The term "(meth)acrylate" refers to methacrylate and/or acrylate.

A "hydrophilic vinylic monomer", as used herein, refers to a vinylic monomer which can be polymerized to form a homopolymer that is water-soluble or can absorb at least 10 percent by weight of water.

A "hydrophobic vinylic monomer" refers to a vinylic monomer which can be polymerized to form a homopolymer that is insoluble in water and can absorb less than 10 percent by weight of water.

"UVA" refers to radiation occurring at wavelengths between 315 and 380 nanometers; "UVB" refers to radiation occurring between 280 and 315 nanometers; "Violet" refers to radiation occurring at wavelengths between 380 and 440 nanometers.

"UVA transmittance" (or "UVA % T"), "UVB transmittance" or "UVB % T", and "violet-transmittance" or "Violet % T" are calculated by the following formula $$UVA\ \%\ T = \frac{\text{Average \% Transmission between 315 and 380 nm}}{\text{Luminescence \% } T} \times 100$$

$$UVB\ \%\ T = \frac{\text{Average \% Transmission between 280 and 315 nm}}{\text{Luminescence \% } T} \times 100$$

$$\text{Violet}\ \%\ T = \frac{\text{Average \% Transmission between 380 and 440 nm}}{\text{Luminescence \% } T} \times 100$$

in which is Luminescence % T is determined by the following formula

Luminescence % $T$=Average % Transmission between 780-380 nm.

As used in this application, the term "macromer" or "prepolymer" refers to a medium and high molecular weight compound or polymer that contains two or more ethylenically unsaturated groups. Medium and high molecular weight typically means average molecular weights greater than 700 Daltons.

As used in this application, the term "vinylic crosslinker" refers to a compound having at least two ethylenically unsaturated groups. A "vinylic crosslinking agent" refers to a vinylic crosslinker having a molecular weight of about 700 Daltons or less.

As used in this application, the term "polymer" means a material formed by polymerizing/crosslinking one or more monomers or macromers or prepolymers.

As used in this application, the term "molecular weight" of a polymeric material (including monomeric or macromeric materials) refers to the weight-average molecular weight unless otherwise specifically noted or unless testing conditions indicate otherwise.

The term "alkyl" refers to a monovalent radical obtained by removing a hydrogen atom from a linear or branched alkane compound. An alkyl group (radical) forms one bond with one other group in an organic compound.

The term "alkylene divalent group" or "alkylene diradical" or "alkyl diradical" interchangeably refers to a divalent radical obtained by removing one hydrogen atom from an alkyl. An alkylene divalent group forms two bonds with other groups in an organic compound.

The term "alkyl triradical" refers to a trivalent radical obtained by removing two hydrogen atoms from an alkyl. A alkyl triradical forms three bonds with other groups in an organic compound.

The term "alkoxy" or "alkoxyl" refers to a monovalent radical obtained by removing the hydrogen atom from the hydroxyl group of a linear or branched alkyl alcohol. An alkoxy group (radical) forms one bond with one other group in an organic compound.

In this application, the term "substituted" in reference to an alkyl diradical or an alkyl radical means that the alkyl diradical or the alkyl radical comprises at least one substituent which replaces one hydrogen atom of the alkyl diradical or the alkyl radical and is selected from the group consisting of hydroxy (—OH), carboxy (—COOH), —NH$_2$, sulfhydryl (—SH), $C_1$-$C_4$ alkyl, $C_1$-$C_4$ alkoxy, $C_1$-$C_4$ alkylthio (alkyl sulfide), $C_1$-$C_4$ acylamino, $C_1$-$C_4$ alkylamino, di-$C_1$-$C_4$ alkylamino, halogen atom (Br or Cl), and combinations thereof.

A "photoinitiator" refers to a chemical that initiates free radical crosslinking/polymerizing reaction by the use of light.

In this application, a "reactive UV-absorbing compound" refers to a compound comprising a dimethyl acetal or diethyl acetal group

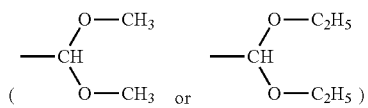

and a UV-absorbing moiety (benzophenone or benzotriazole moiety) which can absorb or screen out UV radiation in the range from 200 nm to 400 nm as understood by a person skilled in the art.

A "spatial limitation of actinic radiation" refers to an act or process in which energy radiation in the form of rays is directed by, for example, a mask or screen or combinations thereof, to impinge, in a spatially restricted manner, onto an area having a well-defined peripheral boundary. A spatial limitation of UV radiation is obtained by using a mask or screen having a radiation (e.g., UV and/or visible light) permeable region, a radiation (e.g., UV and/or visible light) impermeable region surrounding the radiation-permeable region, and a projection contour which is the boundary between the radiation-impermeable and radiation-permeable regions, as schematically illustrated in the drawings of U.S. Pat. No. 6,800,225 (FIGS. 1-11), and U.S. Pat. No. 6,627,124 (FIGS. 1-9), U.S. Pat. No. 7,384,590 (FIGS. 1-6), and U.S. Pat. No. 7,387,759 (FIGS. 1-6), all of which are incorporated by reference in their entireties. The mask or screen allows to spatially projects a beam of radiation (e.g., UV radiation and/or visible radiation) having a cross-sectional profile defined by the projection contour of the mask or screen. The projected beam of radiation (e.g., UV radiation and/or visible radiation) limits radiation impinging on a lens formulation located in the path of the projected beam from the first molding surface to the second molding surface of a mold. The resultant contact lens comprises an anterior surface defined by the first molding surface, an opposite posterior surface defined by the second molding surface, and a lens edge defined by the sectional profile of the projected UV and/or visible beam (i.e., a spatial limitation of radiation). The radiation used for the crosslinking is radiation energy, especially UV radiation (and/or visible radiation), gamma radiation, electron radiation or thermal radiation, the radiation energy preferably being in the form of a substantially parallel beam in order on the one hand to achieve good restriction and on the other hand efficient use of the energy.

The term "modulus" or "elastic modulus" in reference to a contact lens or a material means the tensile modulus or Young's modulus which is a measure of the stiffness of a contact lens or a material. The modulus can be measured using a method in accordance with ANSI Z80.20 standard. A person skilled in the art knows well how to determine the elastic modulus of a silicone hydrogel material or a contact lens. For example, all commercial contact lenses have reported values of elastic modulus.

In general, the invention is directed to a class of dimethyl acetal-containing UV-absorbing compounds which are soluble in water due to the presence of hydrophilic groups, and can be used, in combination with a dimethyl acetal- or diethyl acetal-containing vinylic monomer (e.g., (meth) acrylamidoacetaldehyde dimethyl or diethyl acetal), to chemically modified a polyvinyl alcohol polymer to form a water-soluble, actinically-crosslinkable polyvinyl alcohol prepolymer capable of absorbing UV radiation and optionally HEVL radiation. Resultant polyvinyl alcohol prepolymers are useful for making UV-absorbing hydrogel contact lenses, in particularly, according to the Lightstream Technology™.

In one aspect, the present invention provides an acetal-containing, UV-absorbing compound of any one of formula (I) to (V)

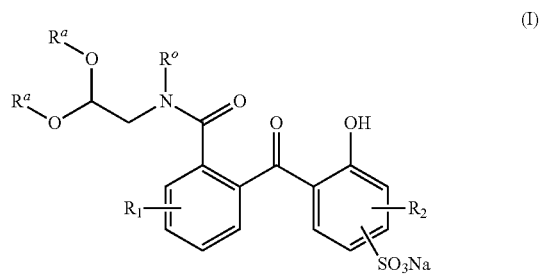

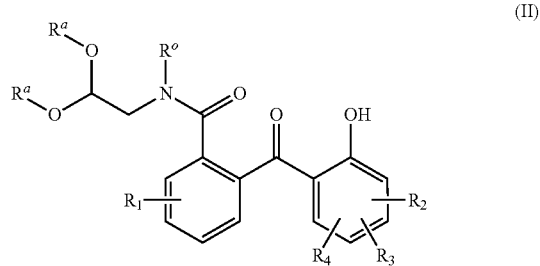

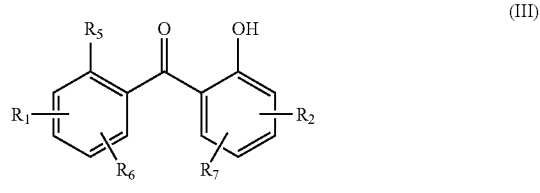

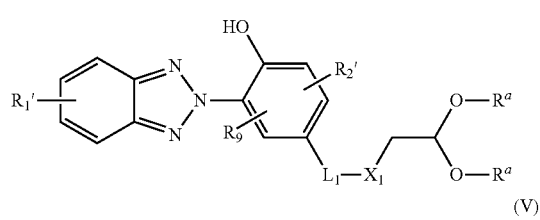

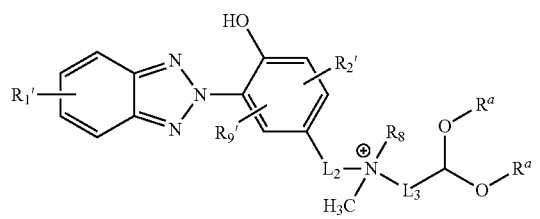

in which:

$R^a$ is $CH_3$ or $C_2H_5$;

$R^o$ is H or $CH_3$;

$R_1$, $R_2$ and $R_2'$ independent of one other are H, $CH_3$, $CCl_3$, $CF_3$, Cl, Br, NR'R" in which R' and R" independent of each other are H or $C_1$-$C_4$ alkyl, OH, or $OCH_3$;

$R_1'$ independent of each other are H, $CH_3$, $CCl_3$, $CF_3$, Cl, Br, NR'R" in which R' and R" independent of each other are H or $C_1$-$C_4$ alkyl, OH, $OCH_3$, $SO_3H$, or $SO_3^-Na^+$;

$R_3$ and $R_4$ independent of each other are H or a first hydrophilic group which is

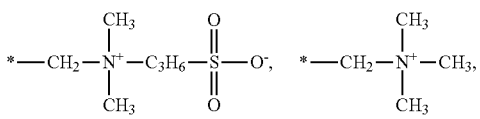

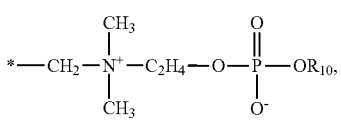

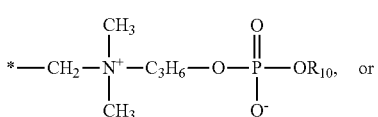

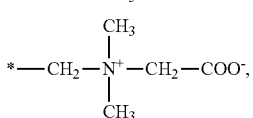

provided that at least one of $R_3$ and $R_4$ is the first hydrophilic group;

r1 is an integer of 1 to 8 (preferably 3 to 6);

n1 is an integer of 2 to 20 (preferably 3 to 15, more preferably 4 to 10);

$R_5$ is H, *—COOH, *—CONH—$C_2H_4$—$(OC_2H_4)_{n1}$—$OCH_3$, or —CONH—$C_2H_4$—$(OC_2H_4)_{n1}$—OH;

one of $R_6$ and $R_7$ is H or a second hydrophilic group which is

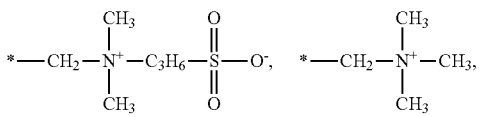

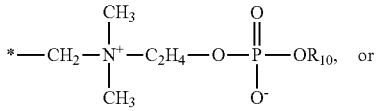

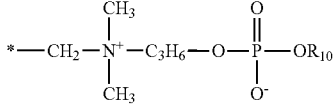

while the other of $R_6$ and $R_7$ is

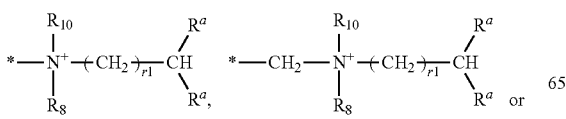

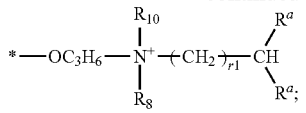

$R_8$ is $CH_3$, $C_2H_5$,

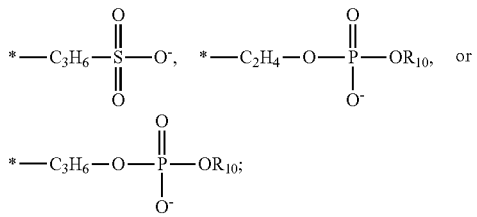

$R_9$ is $SO_3Na$,

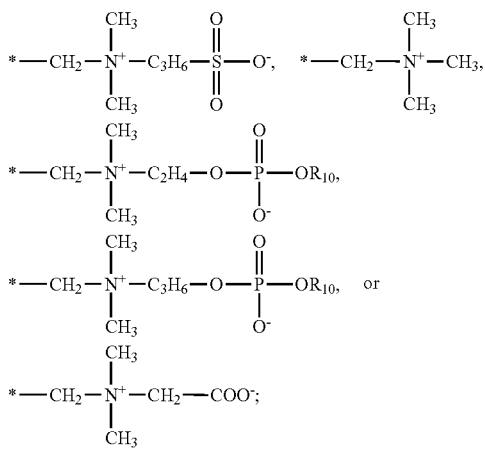

$R_9'$ is H, $SO_3Na$,

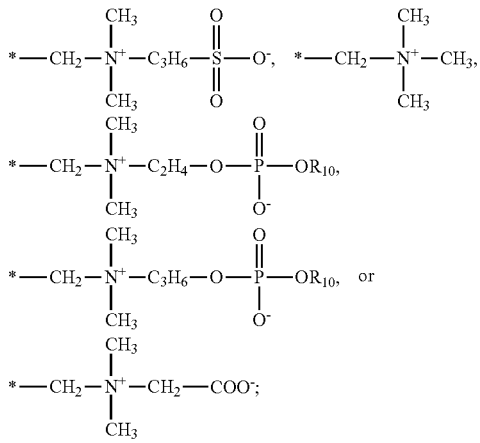

$R_{10}$ is methyl or ethyl;

L1 is a linkage of

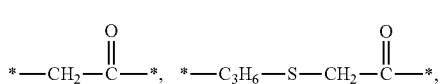

-continued

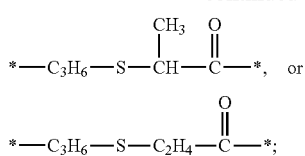

L2 is a linkage of

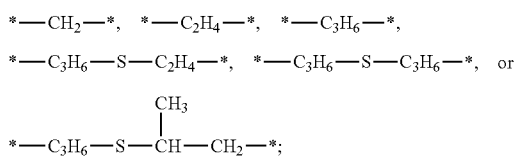

L3 is a linkage of

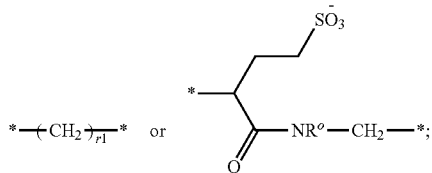

and

X1 is O or NR°.

Examples of preferred an acetal-containing, UV-absorbing compound of formula (I) include without limitation:

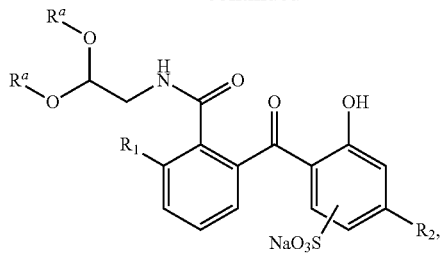

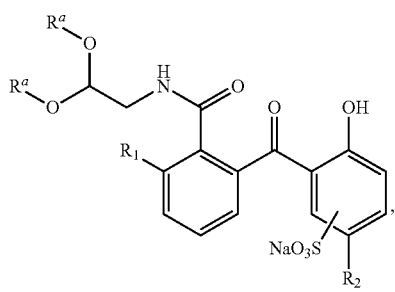

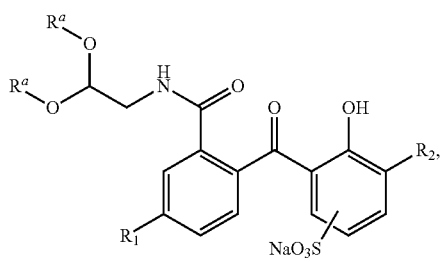

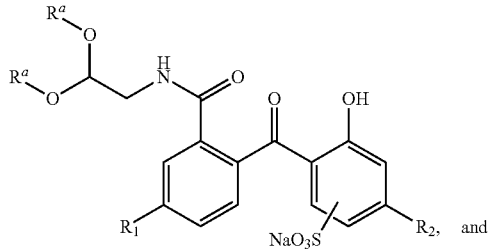

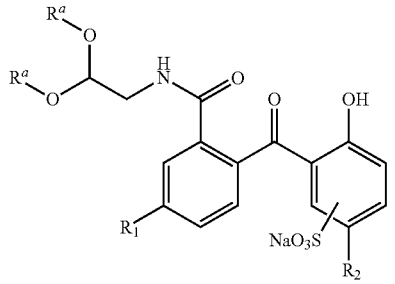

and in which $R^a$ is methyl or ethyl, $R_1$ and $R_2$ independent of each other are H, $CH_3$, $CCl_3$, $CF_3$, Cl, Br, NR'R", OH, or $OCH_3$, in which R' and R" independent of each other are H, methyl or ethyl.

Examples of preferred an acetal-containing, UV-absorbing compound of formula (II) include without limitation:

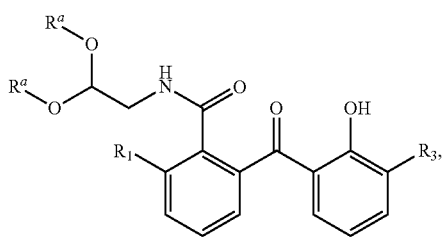
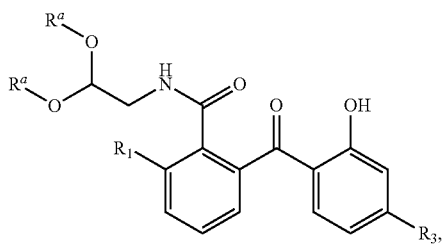
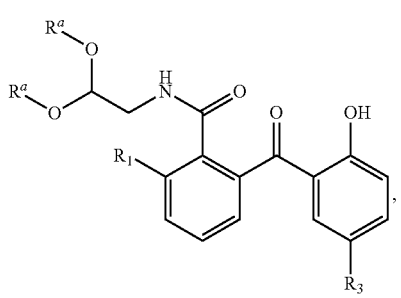
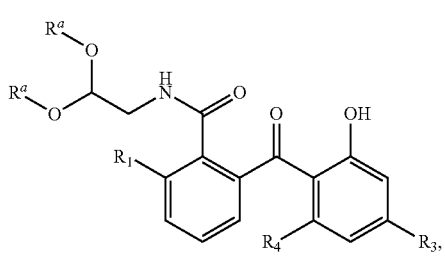
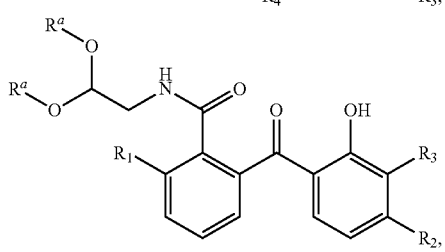
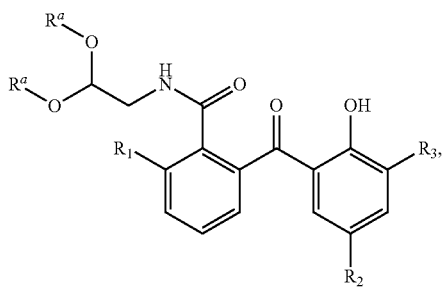
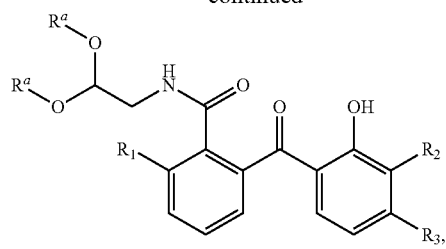
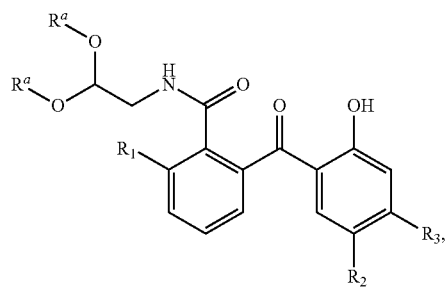
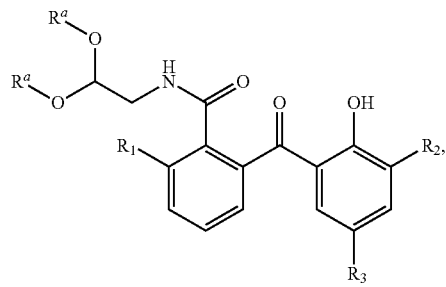
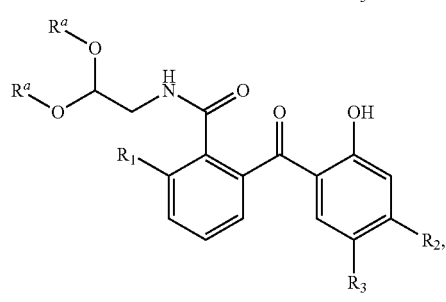
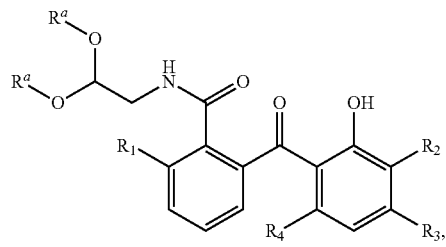
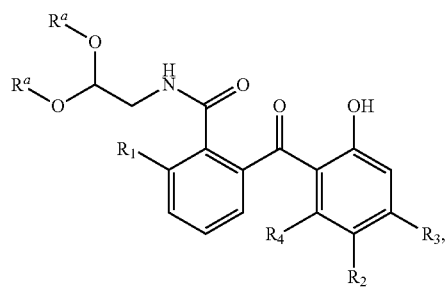

-continued
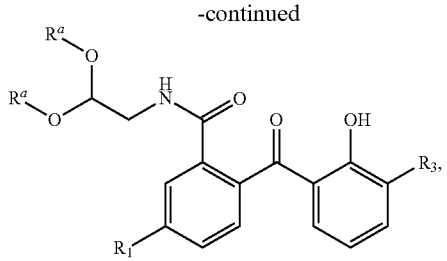
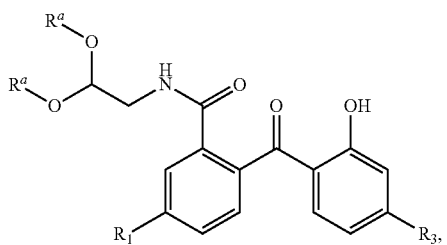
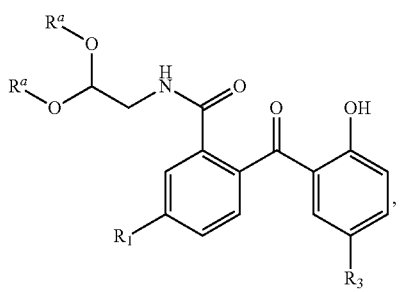
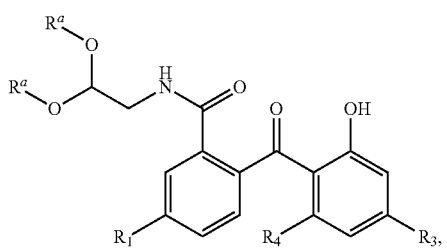
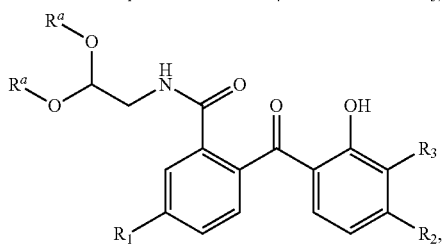
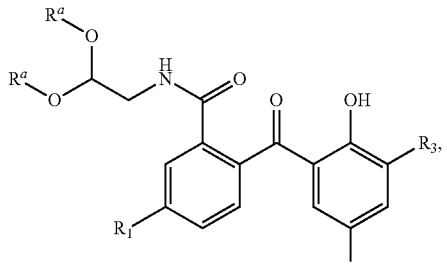
-continued
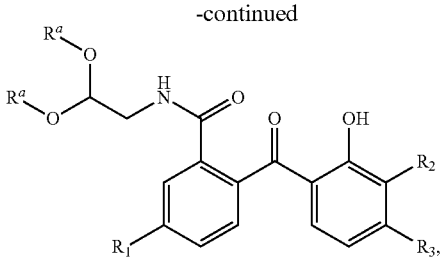
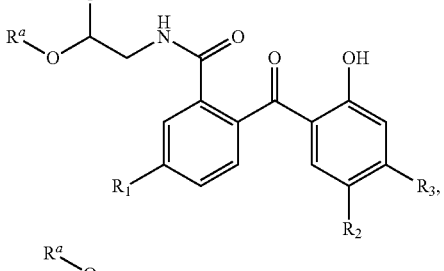
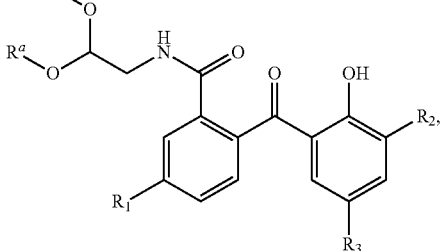
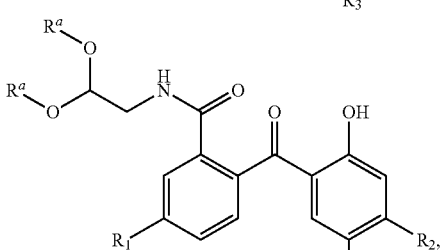
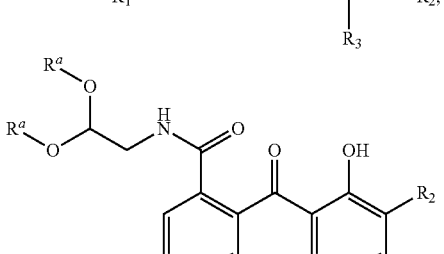
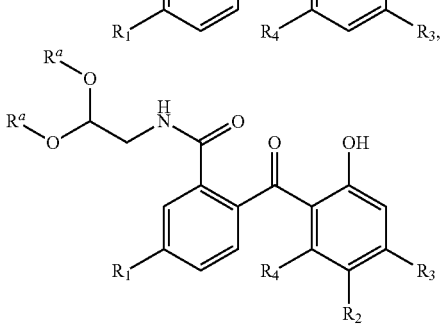
in which: $R^a$ is methyl or ethyl; $R_1$ and $R_2$ independent of each other are $CH_3$, $CCl_3$, $CF_3$, Cl, Br, NR'R", OH, or $OCH_3$; R' and R" independent of each other are H, methyl or ethyl; $R_3$ and $R_4$ independent of each other are

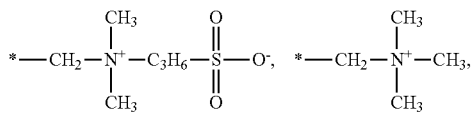
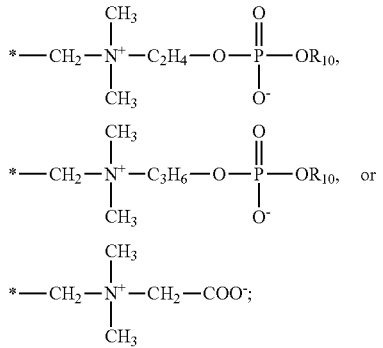
$R_{10}$ is methyl or ethyl.
Examples of preferred an acetal-containing, UV-absorbing compound of formula (III) include without limitation:
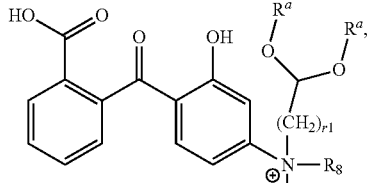
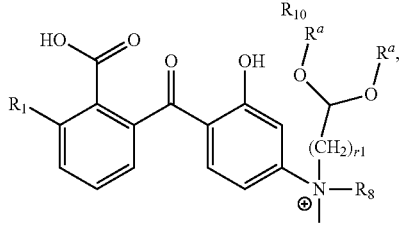
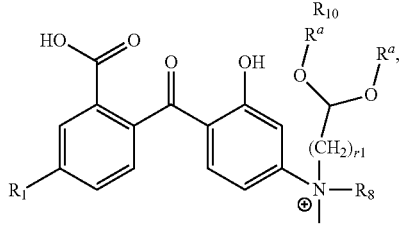
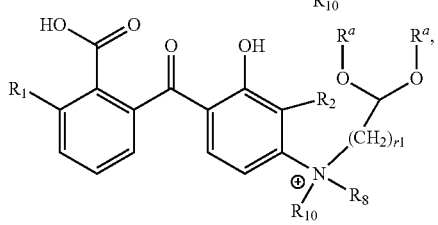
-continued
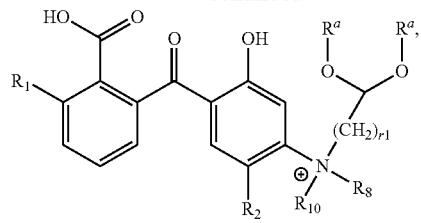
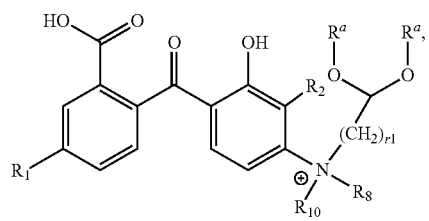
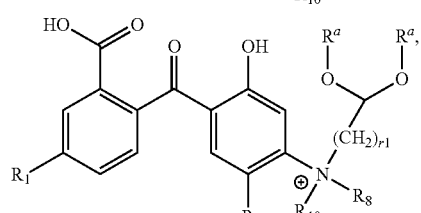
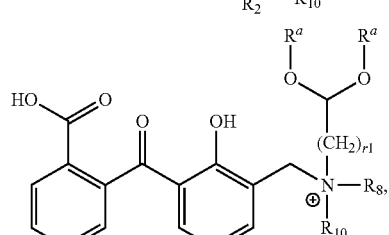
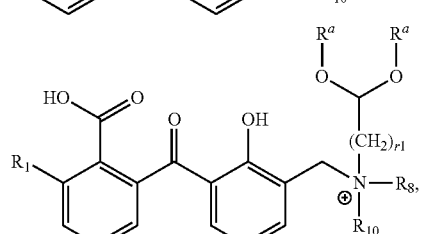
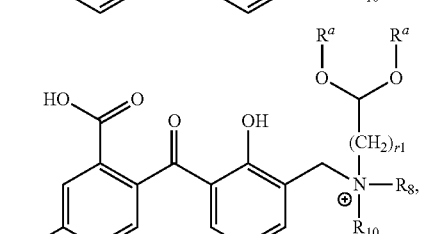
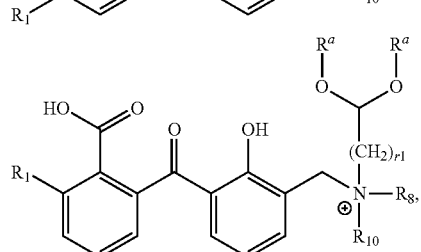

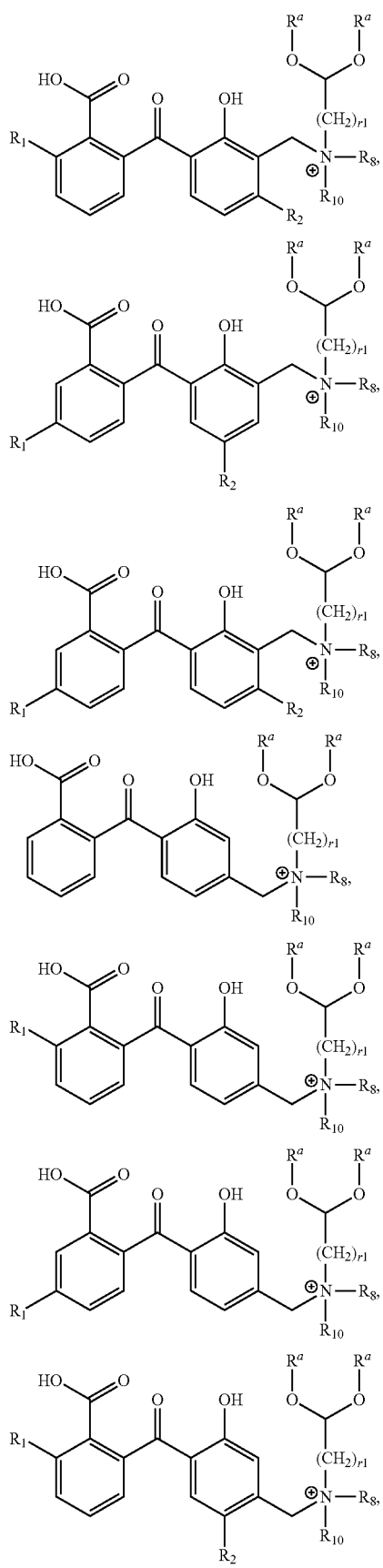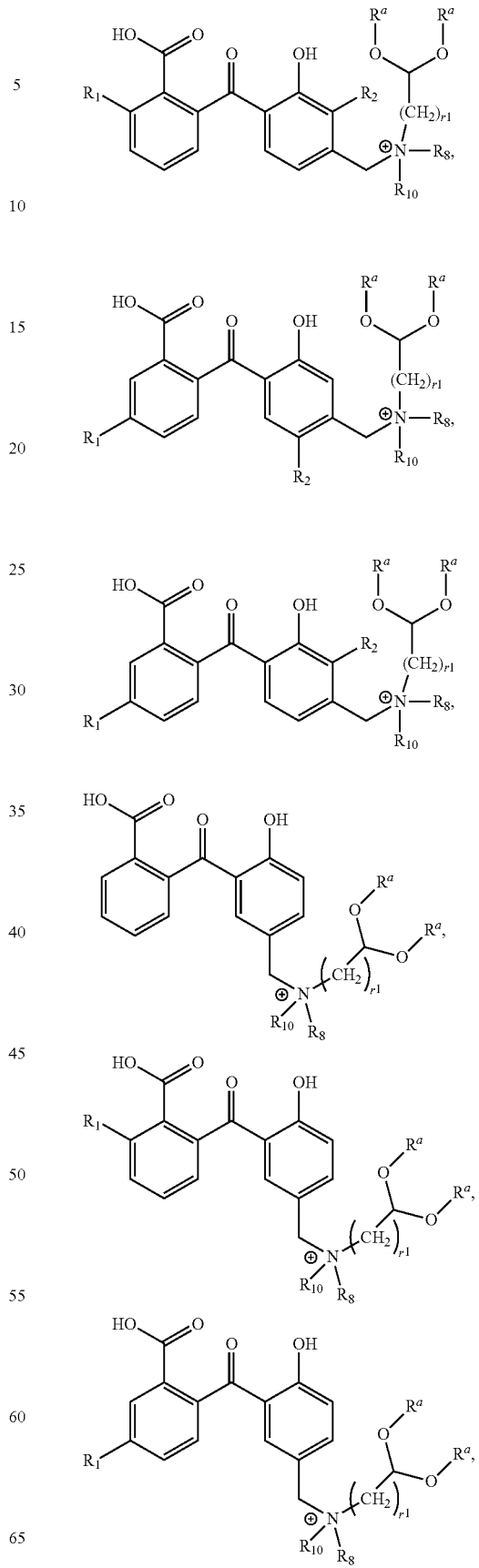

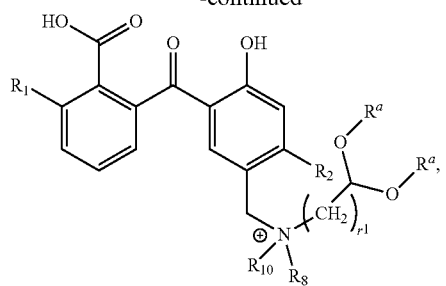
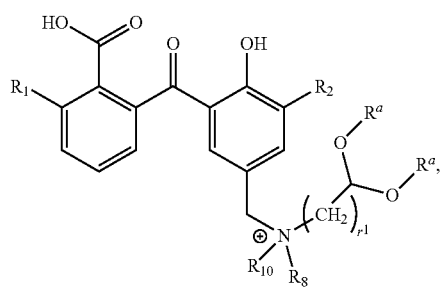
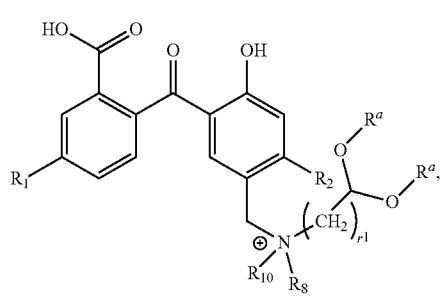
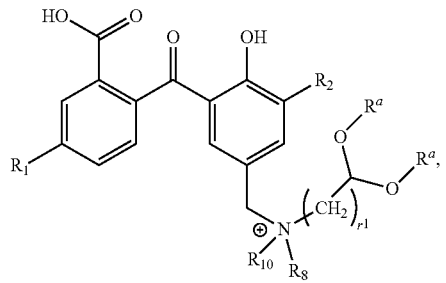
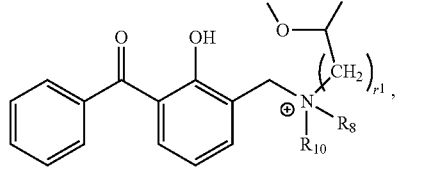
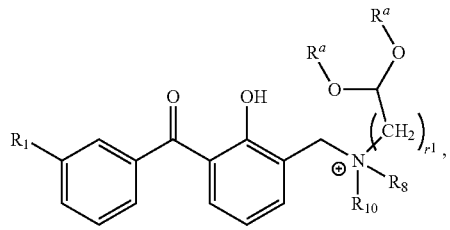
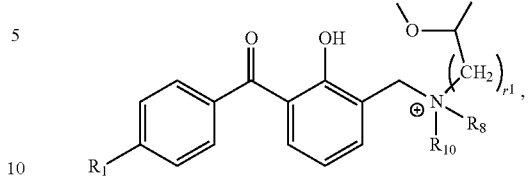
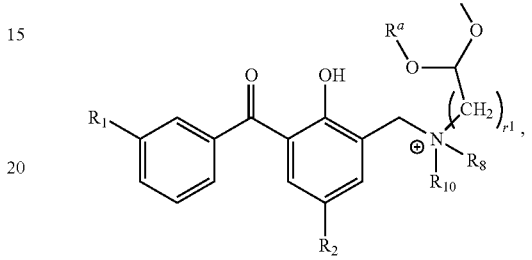
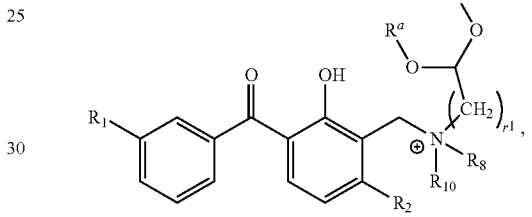
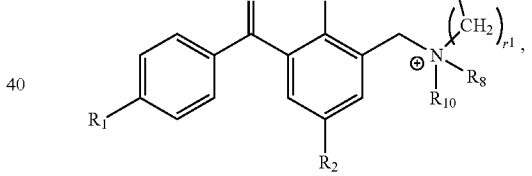
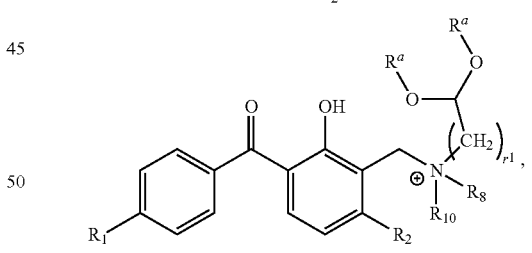
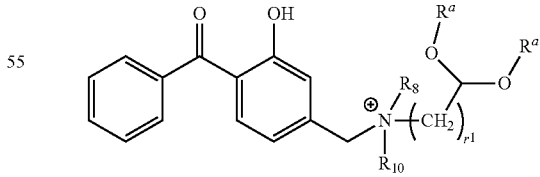
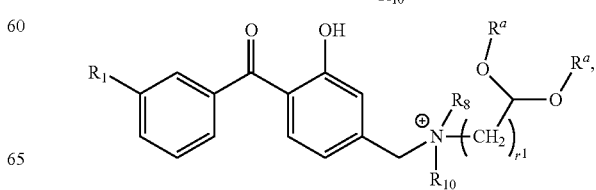
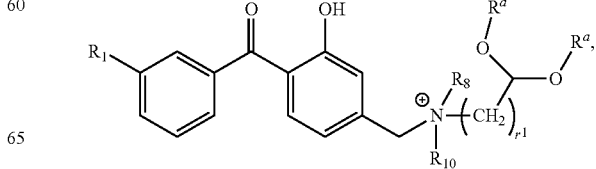

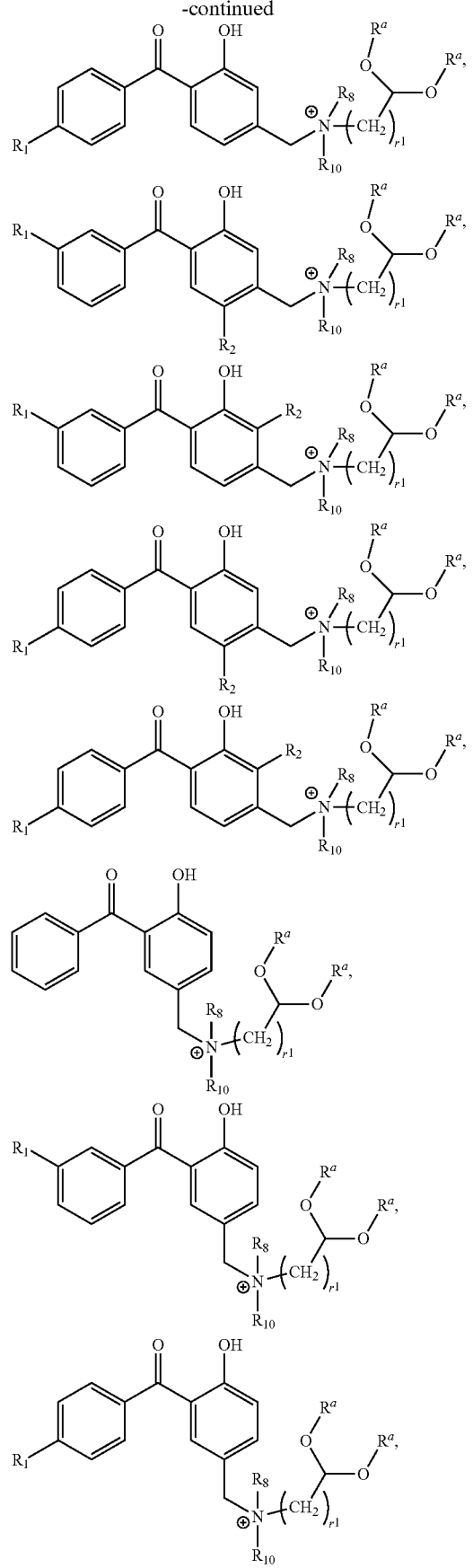
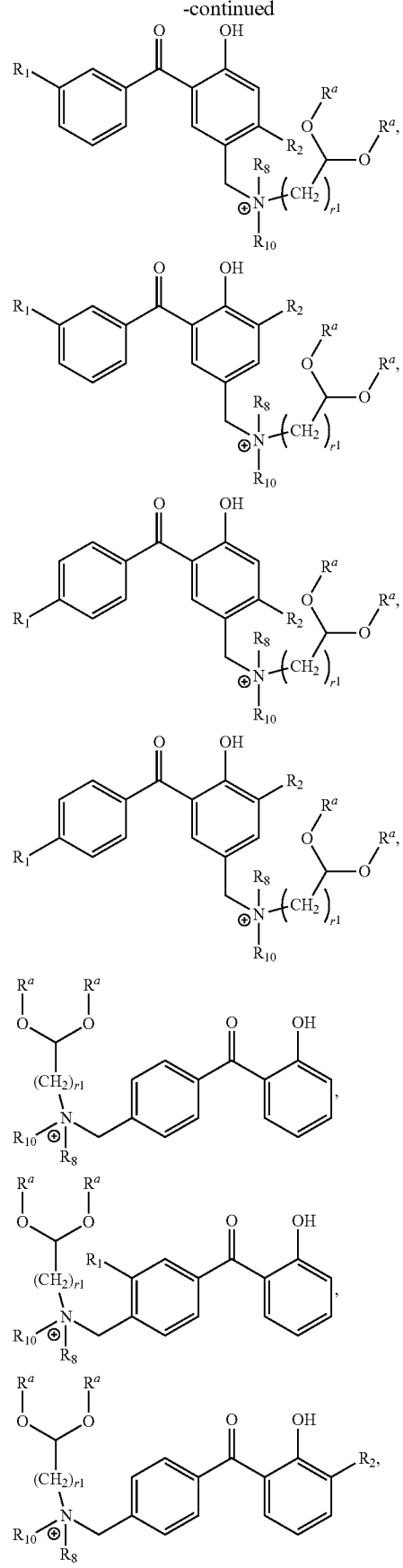

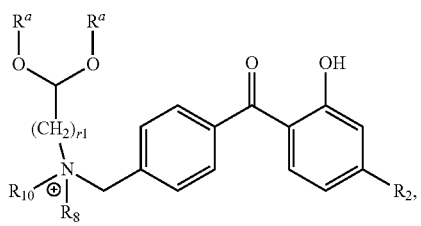
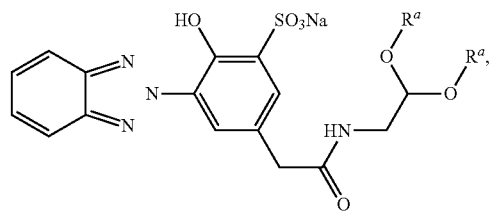
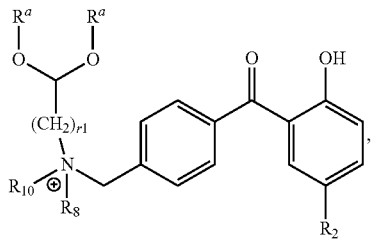
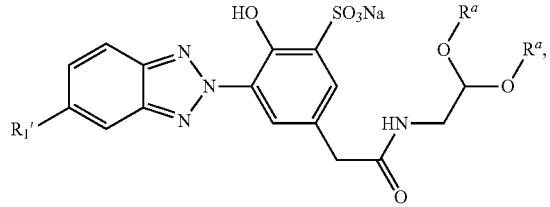
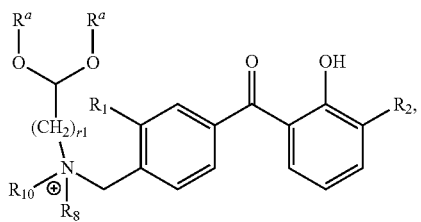
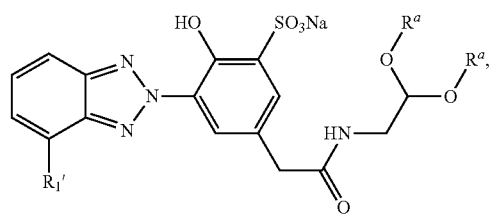
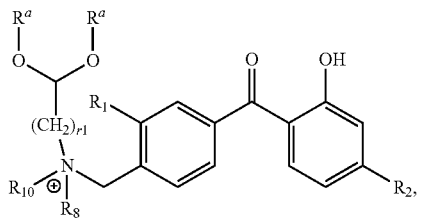
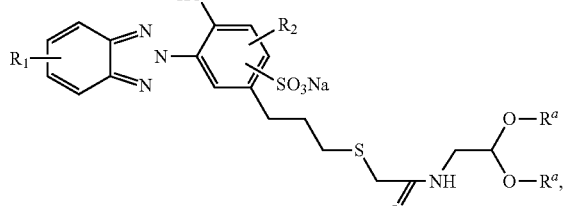
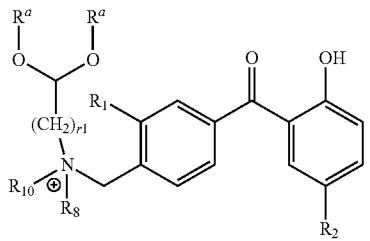
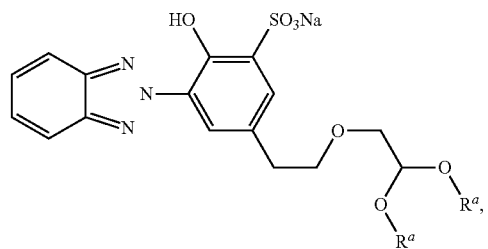
in which: $R^a$ is methyl or ethyl; $R_1$ and $R_2$ independent of each other are $CH_3$, $CCl_3$, $CF_3$, Cl, Br, NR'R" OH, or $OCH_3$; in which R' and R" independent of each other are H or $C_1$-$C_4$ alkyl; $R_8$ is $CH_3$, $C_2H_5$,
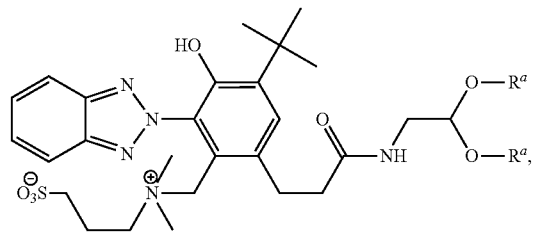
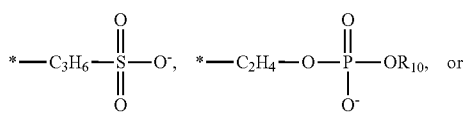
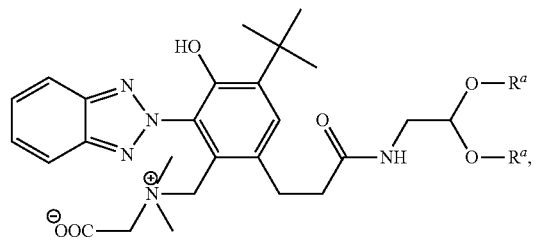
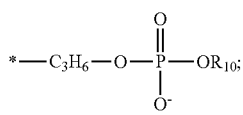
$R_{10}$ is methyl or ethyl; and r1 is an integer of 3 to 6.
Examples of preferred an acetal-containing, UV-absorbing compound of formula (IV) include without limitation:

-continued
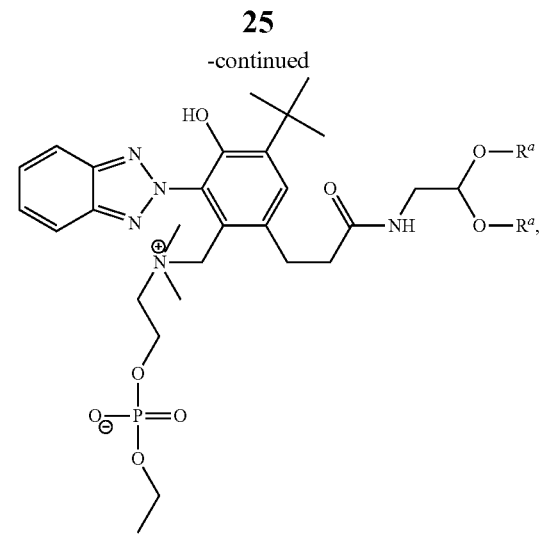
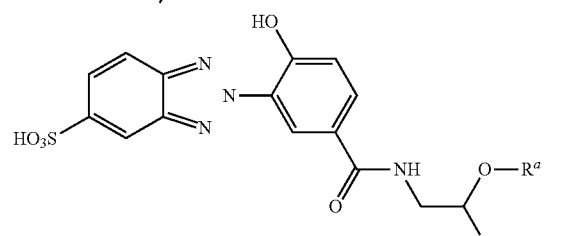
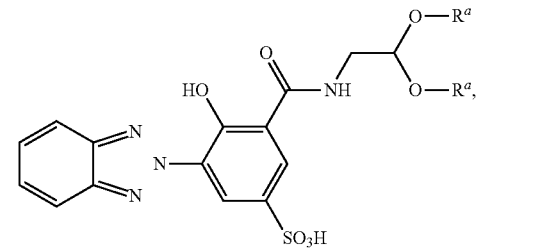
in which $R^a$ is methyl or ethyl; $R^o$ is H or $CH_3$; $R_1$ and $R_2$ independent of each other are H, $CH_3$, $CCl_3$, $CF_3$, Cl, Br, NR'R" in which R' and R" independent of each other are H or $C_1$-$C_4$ alkyl, OH, or $OCH_3$.
Examples of preferred an acetal-containing, UV-absorbing compound of formula (V) include without limitation:
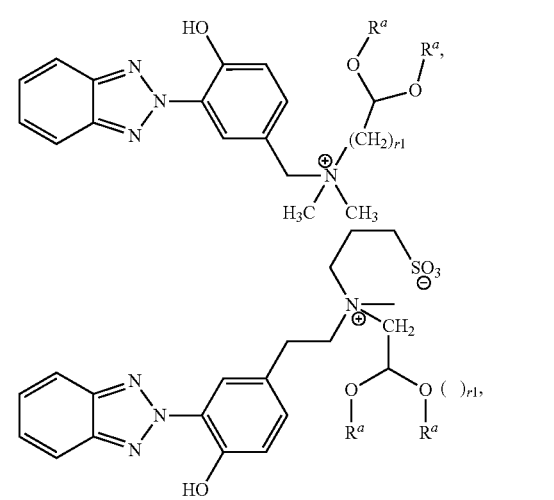
-continued
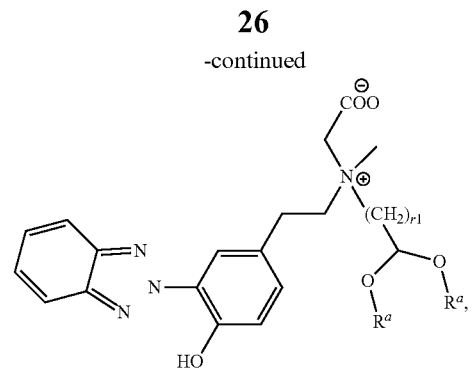
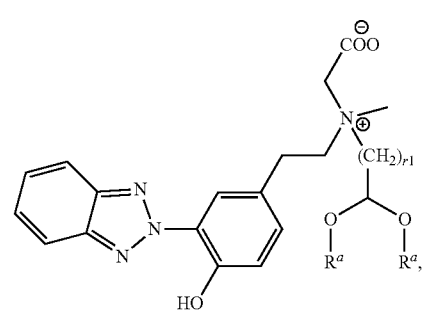
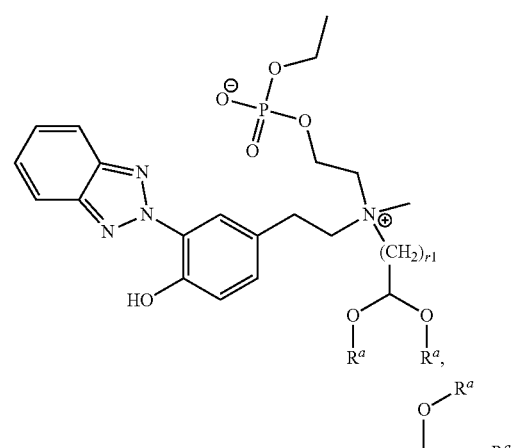
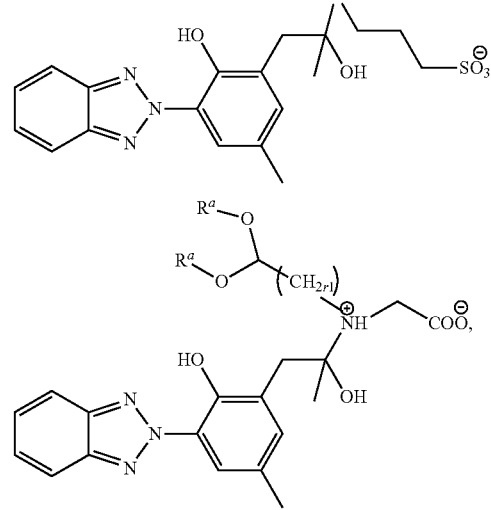

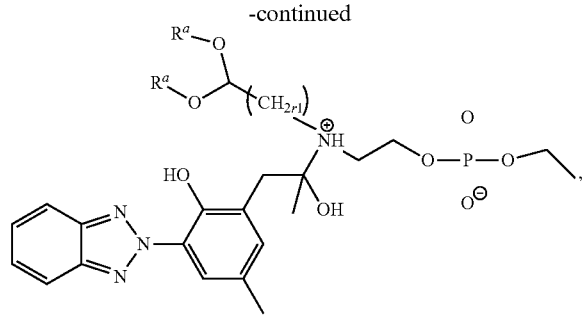
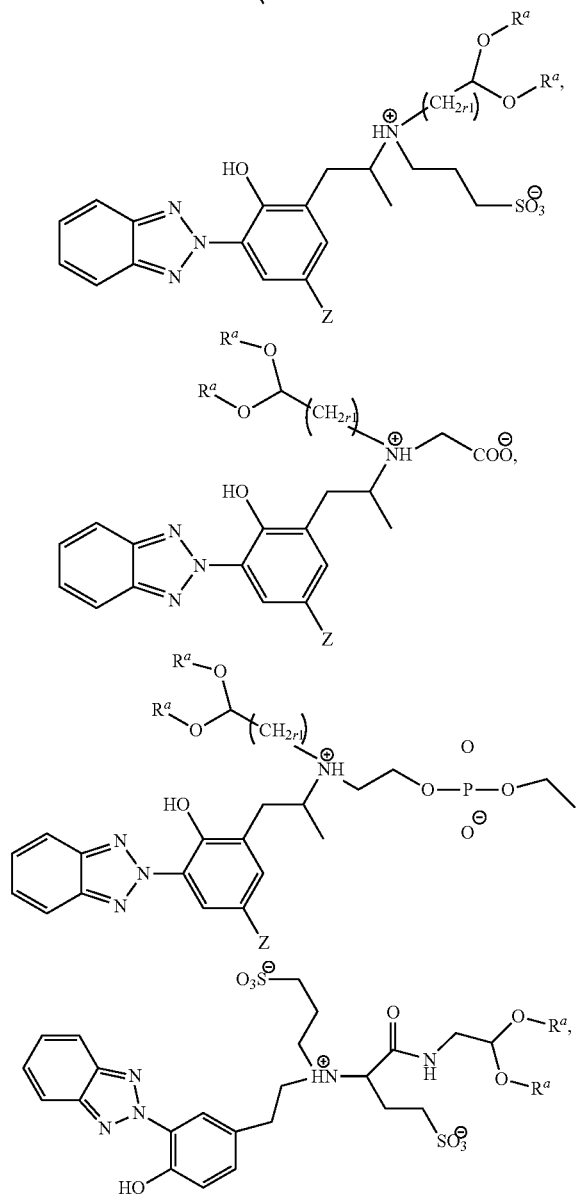
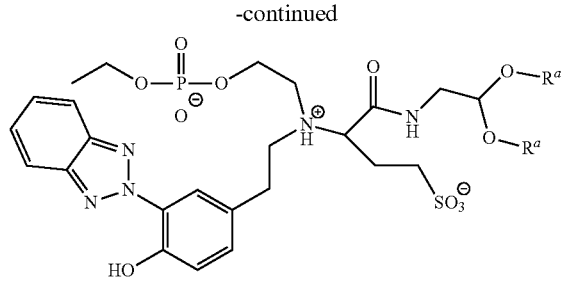
in which $R^a$ is methyl or ethyl, r1 is an integer of 3 to 6, and $Z=CH_3$ or COOH.
An acetal-containing UV-absorbing compound of formula (I) defined above can be prepared according to procedures illustrated in Scheme 1:
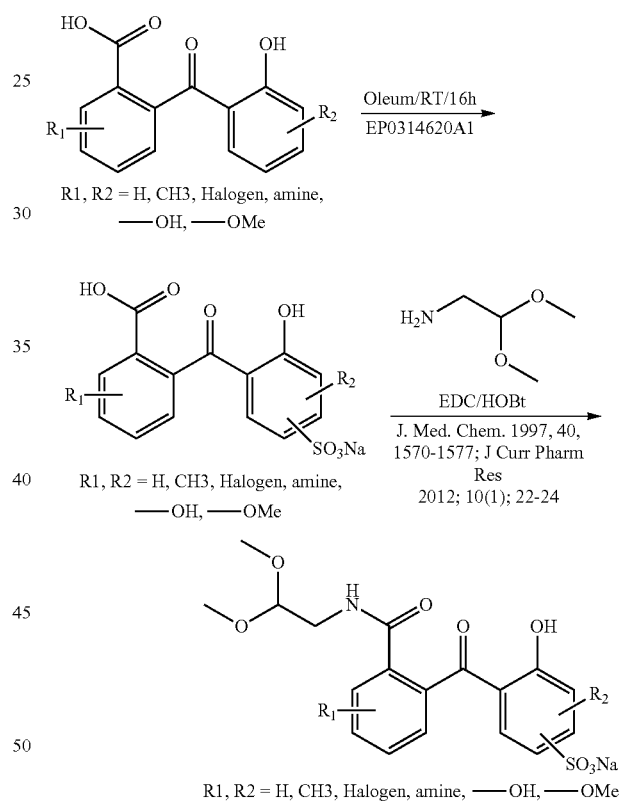
An acetal-containing UV-absorbing compound of formula (II) defined above can be prepared according to procedures illustrated in Scheme 2:

-continued

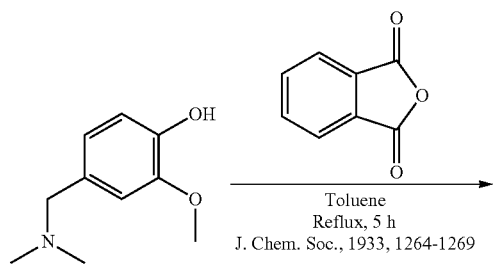

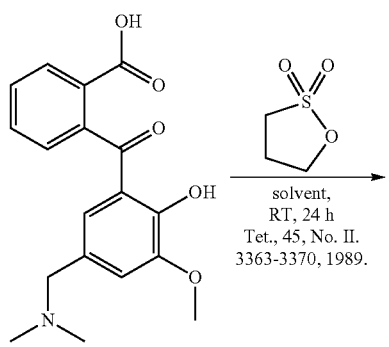

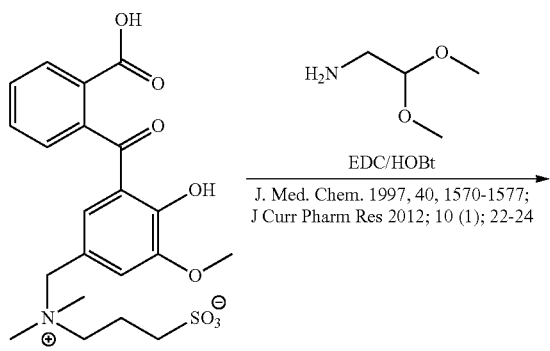

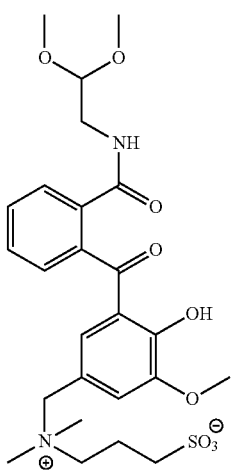

An acetal-containing UV-absorbing compound of formula (III) defined above can be prepared according to procedures illustrated in Scheme 3:

Scheme 3

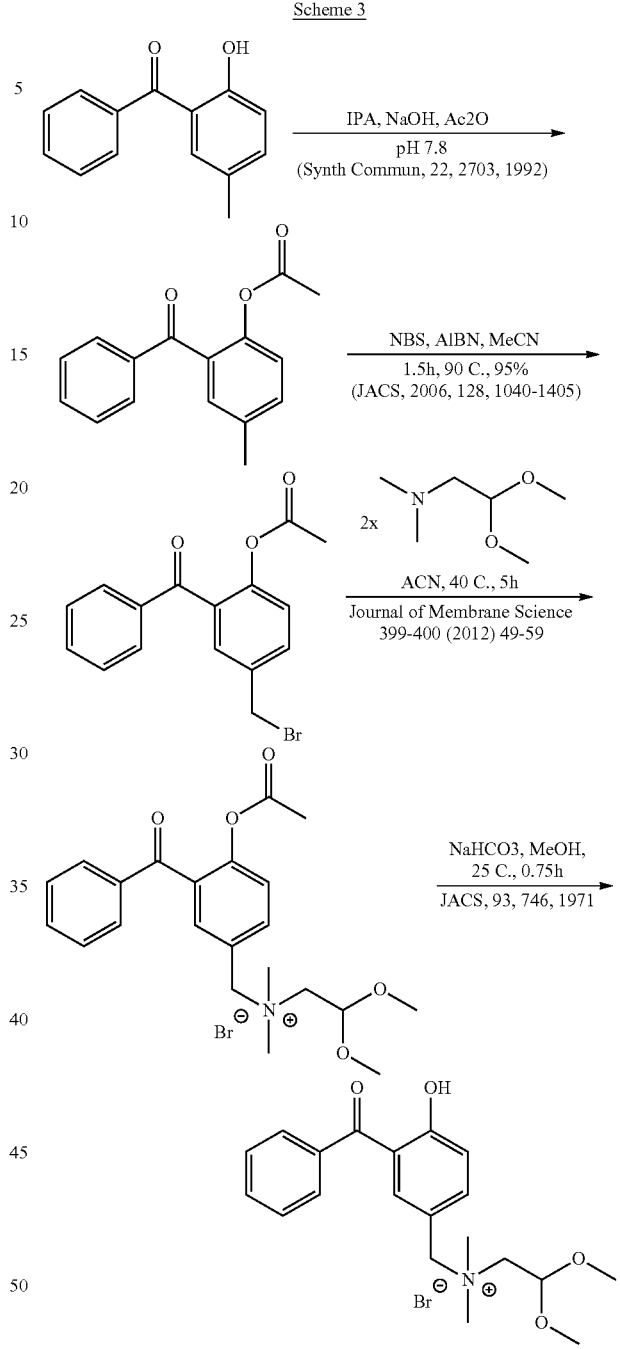

It is understood that in the $2^{nd}$ step of Scheme 1 or 2, 2,2-dimethoxyethanamine can be substituted with 1,1-dimethoxy-N-methylethanamine. The $3^{rd}$ step of Scheme 2 can be altered to form a phosphocholine group by reacting an alkyl alkylene phosphate (e.g., methyl ethylene phosphate, ethyl ethylene phosphate, methyl propylene phosphate, or ethyl propylene phosphate), instead of 1,3-propane sultone, under conditions known to a person skilled in the art (Makromol. Chem., Rapid Commun. 3, 457-459 (1982). It is also understood that Scheme 3 can be modified by replacing 1,1-dimethoxy-N,N-dimethylethanamine with 1,1-dimethoxy-N-methylethanamine and then by adding one step of reacting the product of the $3^{rd}$ step with 1,3-propane sultone or an alkyl alkylene phosphate (e.g., methyl ethylene phosphate, ethyl ethylene phosphate, methyl propylene phosphate, or ethyl propylene phosphate) under conditions known to a person skilled in the art to form a compound of formula (III) with $R_8$ is a radical other than methyl.

Any 2-hydroxy-2'-carboxy benzophenones with substituents on either or both benzene rings can be used in the preparation of a compound of formula (I), (II) or (III). A person knows how to prepare a 2-hydroxy-2'-carboxy benzophenones with substituents from a substituted or unsubstituted phthalic anhydride and a substituted or unsubstituted phenol (see, e.g., U.S. Pat. No. 5,925,787, herein incorporated in reference in its entirety).

It is understood that in the $2^{nd}$ step of Scheme 2 any 3- and 4-substituted phthalic anhydride can be used to react with any mono- or di-substituted phenol to obtain a compound of formula (I), (II) or (III). Various 3- and 4-substituted phthalic anhydrides are commercially available or can be prepared according to the procedures described in *J. Chem. Soc., Perkin Trans.* (1977), 1: 2030-2036 (herein incorporated by reference in its entirety).

An acetal-containing UV-absorbing compound of formula (IV) defined above can be prepared according to procedures illustrated in any one of Schemes 4 to 7:

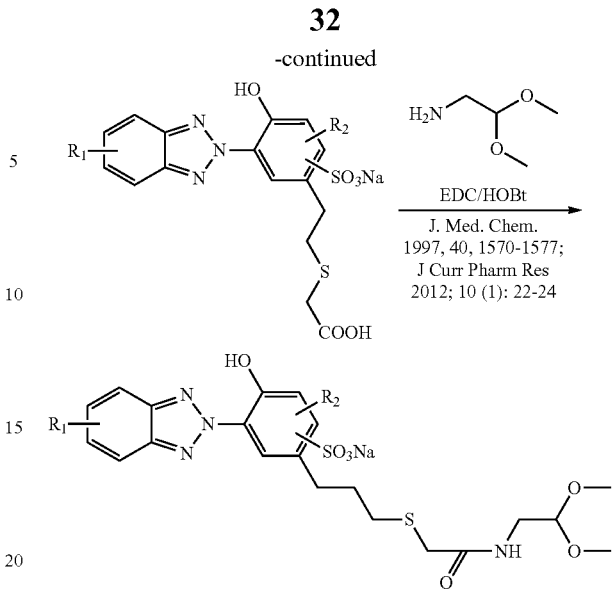

Scheme 4

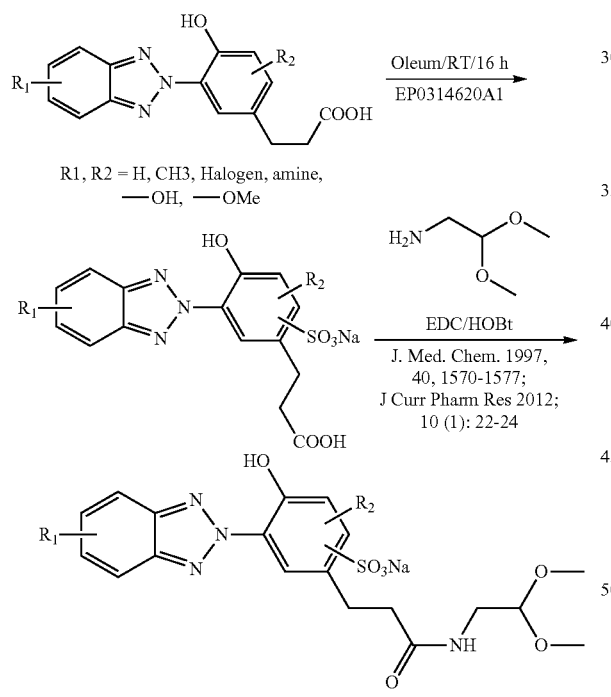

Scheme 6

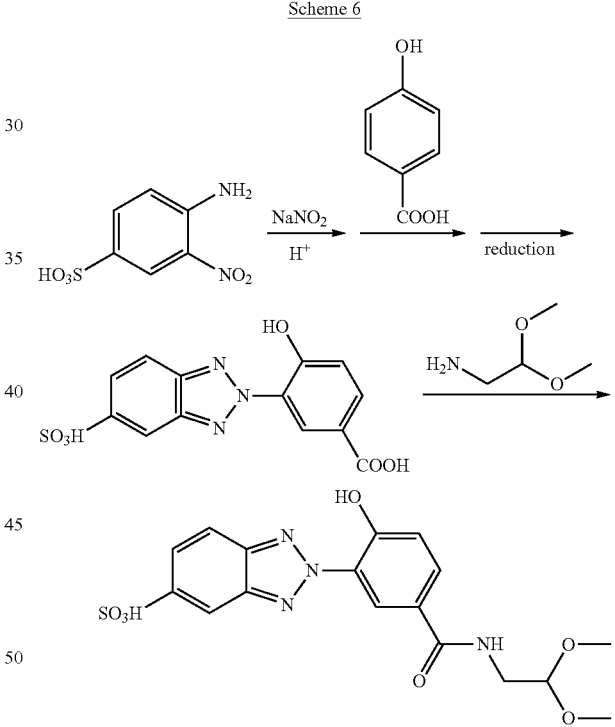

Scheme 5

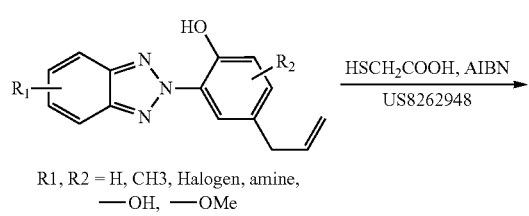

Scheme 7

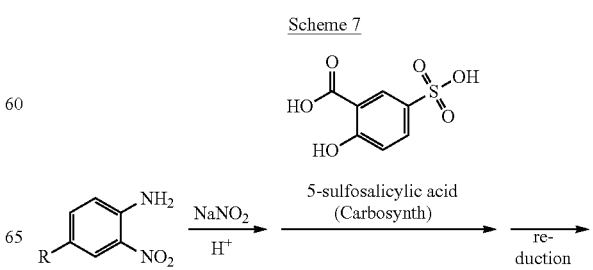

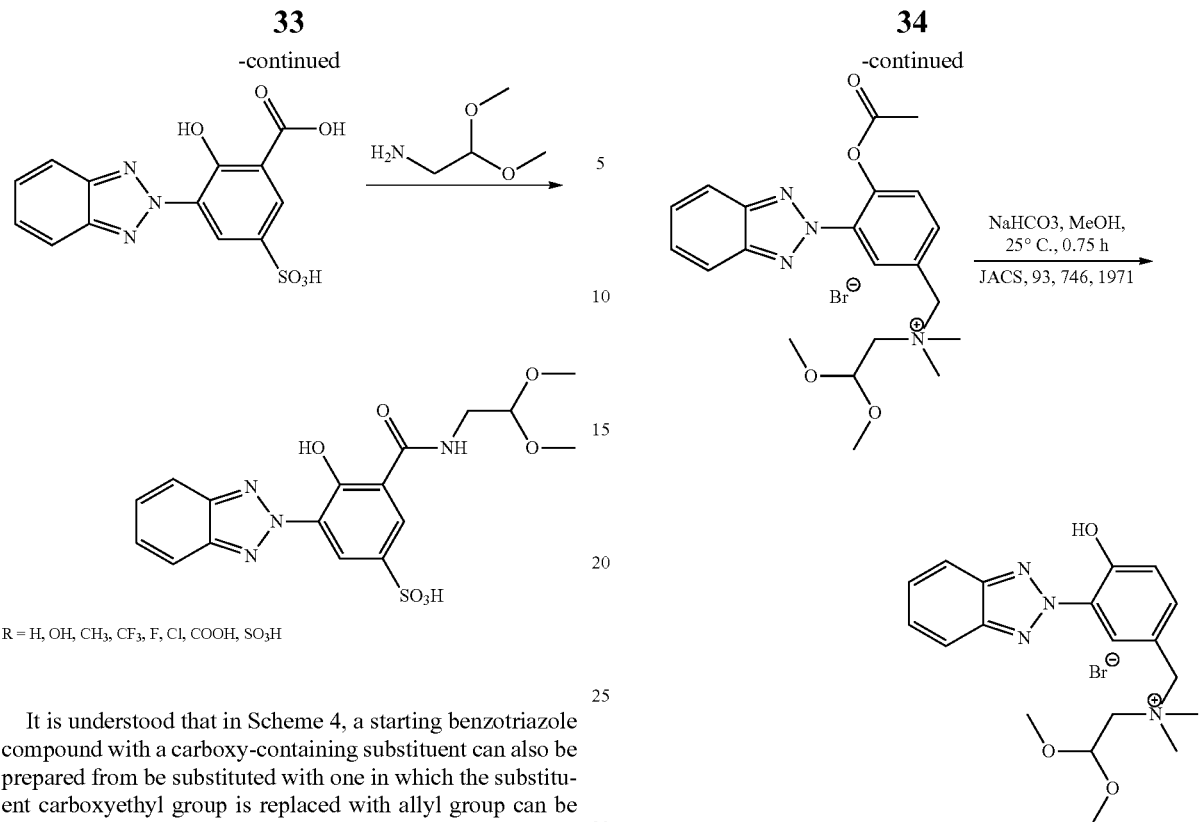

R = H, OH, CH3, CF3, F, Cl, COOH, SO3H

It is understood that in Scheme 4, a starting benzotriazole compound with a carboxy-containing substituent can also be prepared from be substituted with one in which the substituent carboxyethyl group is replaced with allyl group can be substit An acetal-containing UV-absorbing compound of formula (V) defined above can be prepared according to procedures illustrated in Scheme 8 or 9:

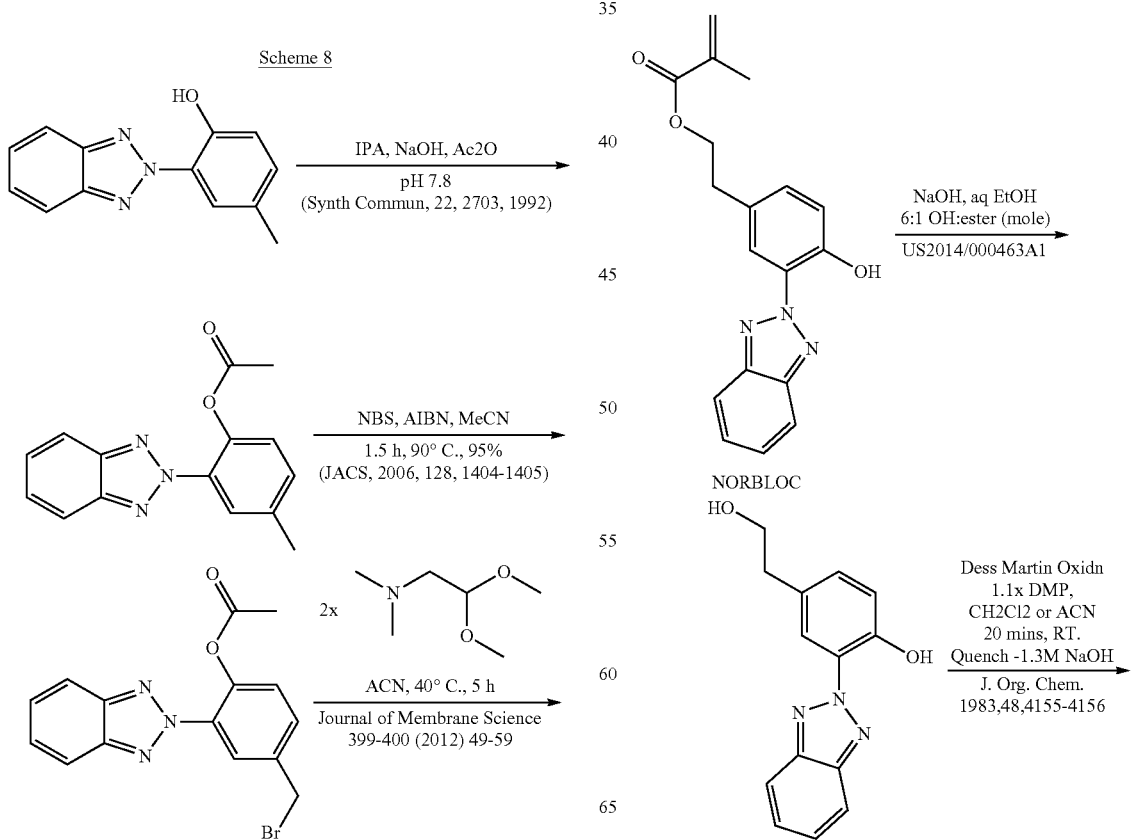

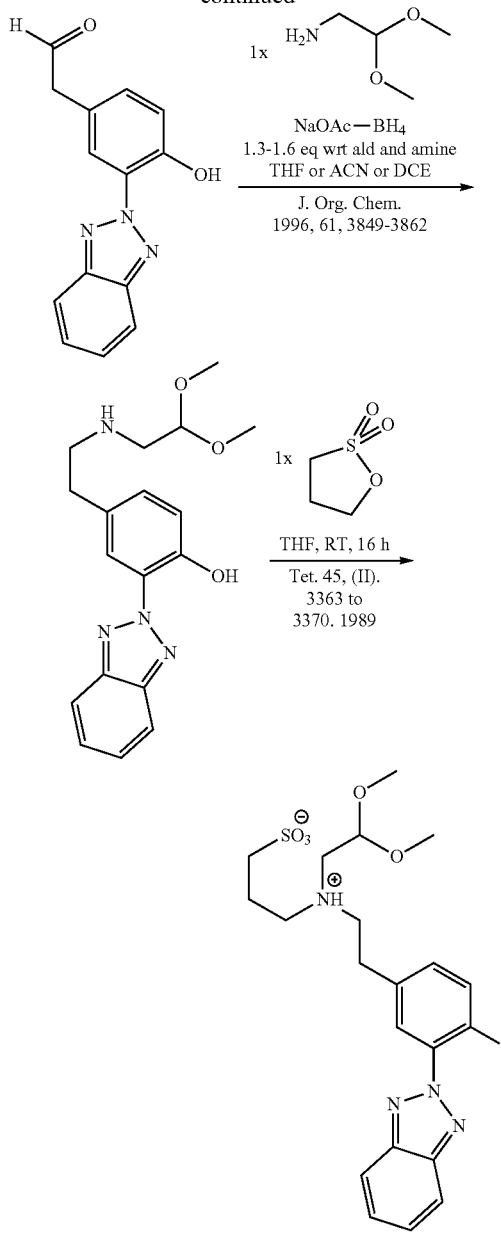

In another aspect, the invention provides a water-soluble, actinically-crosslinkable polyvinyl alcohol prepolymer, comprising:

repeating units of vinyl alcohol (i.e.,

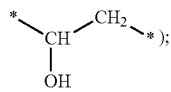

);

repeating crosslinking units of formula (VI); and

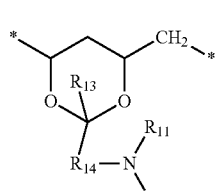

(VI)

repeating UV-absorbing units of formula (VII)

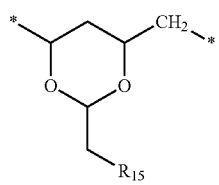

(VII)

in which:

$R_{11}$ is hydrogen or $C_1$-$C_6$ alkyl (preferably hydrogen or $C_1$-$C_4$ alkyl, more preferably hydrogen or methyl or ethyl, even more preferably hydrogen or methyl);

$R_{12}$ is an ethylenically unsaturated group of

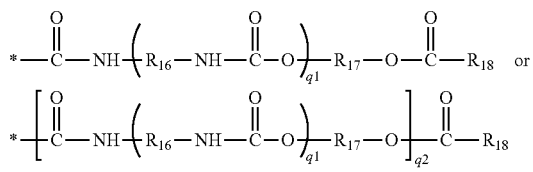

in which q1 and q2 independently of each another are zero or one, and $R_{16}$ and $R_{17}$ independently of one another are a $C_2$-$C_8$ alkylene divalent radical, $R_{18}$ is $C_2$-$C_8$ alkenyl;

$R_{13}$ can be hydrogen or a $C_1$-$C_6$ alkyl group (preferably hydrogen);

$R_{14}$ is a $C_1$-$C_6$ alkylene divalent radical (preferably a $C_1$-$C_4$ alkylene divalent radical, more preferably methylene or butylene divalent radical, even more preferably methylene divalent radical);

$R_{15}$ is a monovalent radical of any one of formula (VIII)-(XII)

Any benzotriazoles with substituents can be used in the preparation of a compound of formula (IV) or (V). A person knows how to prepare a benzotriazole with different substituents according to a known procedure (see, e.g., U.S. Pat. No. 8,262,948, herein incorporated in reference in its entirety).

An UV-absorbing compound can be used to react with a polyvinyl alcohol to form a water-soluble, actinically-crosslinkable polyvinyl alcohol prepolymer capable of absorbing UV radiation and optionally HEVL radiation, because its dimethyl acetal group can react with 1,3-diol basic units of the polyvinyl alcohol polymer to form 1,3-dioxane units in which the UV-absorbing compound is attached at the 2-position (see, e.g., U.S. Pat. Nos. 5,583,163 and 6,303,687, herein incorporated by references in their entireties). Such a water-soluble, actinically-crosslinkable polyvinyl alcohol polymer is provided in another aspect of the invention.

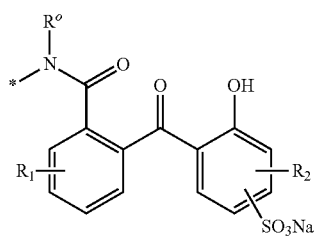
(VIII)

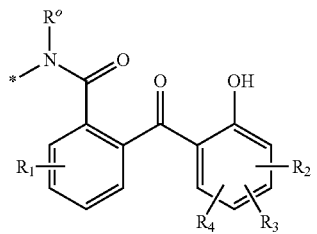
(IX)

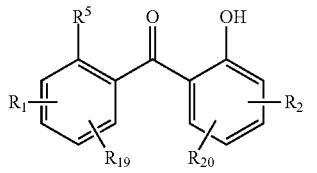
(X)

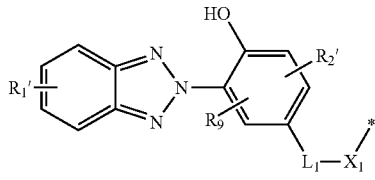
(XI)

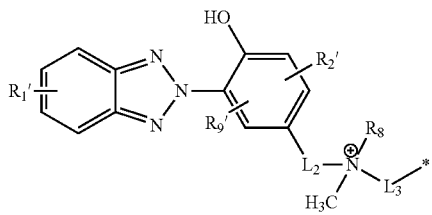
(XII)

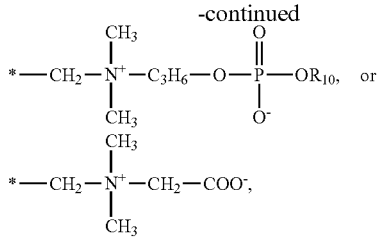

provided that at least one of $R_3$ and $R_4$ is the first hydrophilic group;
r1 is an integer of 1 to 8 (preferably 3 to 6);
n1 is an integer of 2 to 20 (preferably 3 to 15, more preferably 4 to 10);
$R_5$ is H, *—COOH, *—CONH—$C_2H_4$—$(OC_2H_4)_{n1}$—$OCH_3$, or *—CONH—$C_2H_4$—$(OC_2H_4)_{n1}$—OH;
$R_8$ is $CH_3$, $C_2H_5$,

*—$C_3H_6$—S(=O)(=O)—O⁻,   *—$C_2H_4$—O—P(=O)(OR_{10})—O⁻,   or

*—$C_3H_6$—O—P(=O)(OR_{10})—O⁻;

$R_9$ is $SO_3Na$,

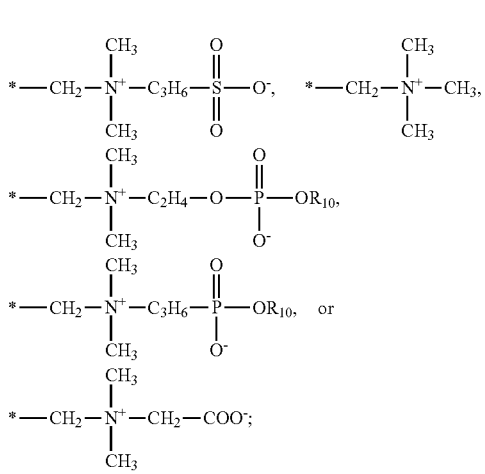

$R_9'$ is H, $SO_3Na$,

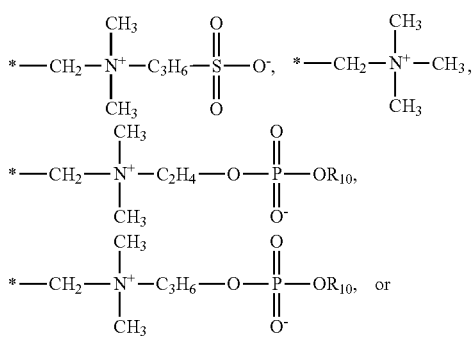

$R^o$ is H or $CH_3$;
$R_1$, $R_2$ and $R_2'$ independent of one other are H, $CH_3$, $CCl_3$, $CF_3$, Cl, Br, NR'R" in which R' and R" independent of each other are H or $C_1$-$C_4$ alkyl, OH, or $OCH_3$;
$R_1'$ independent of each other are H, $CH_3$, $CCl_3$, $CF_3$, Cl, Br, NR'R" in which R' and R" independent of each other are H or $C_1$-$C_4$ alkyl, OH, $OCH_3$, $SO_3H$, or $SO_3^-Na^+$;
$R_3$ and $R_4$ independent of each other are H or a first hydrophilic group which is

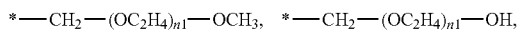

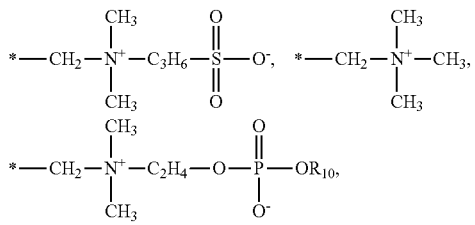

-continued

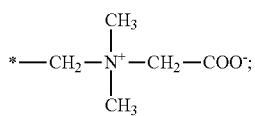

$R_{10}$ is methyl or ethyl;

L1 is a linkage of

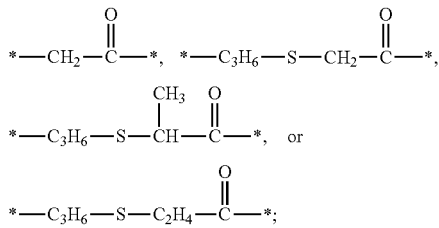

L2 is a linkage of

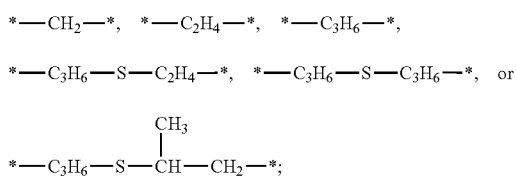

L3 is a linkage of

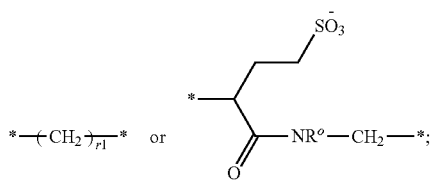

X1 is O or $NR^o$;

one of $R_{19}$ and $R_{20}$ is H or a second hydrophilic group which is

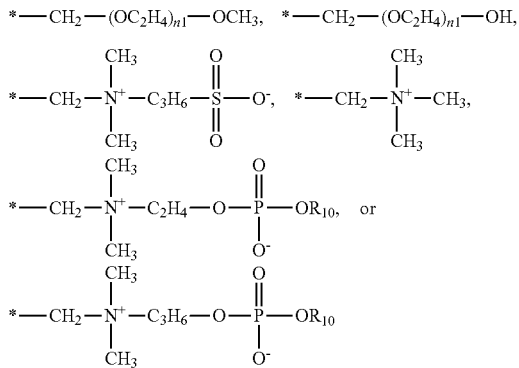

while the other of $R_{19}$ and $R_{20}$ is a divalent radical of

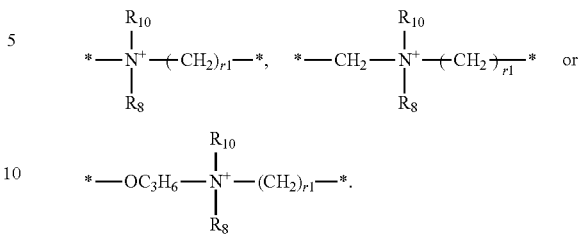

In a preferred embodiment, the prepolymer is a water-soluble crosslinkable poly(vinyl alcohol), has a weight average molecular weight of at least about 2,000 Daltons, and comprises from about 1% to about 25% by mole, preferably from about 2% to about 15% by mole of the repeating units of formula (VI).

In another preferred embodiment, wherein $R_{14}$ is methylene divalent radical, $R_{11}$ is hydrogen or $C_1$-$C_4$ alkyl, $R_{13}$ is hydrogen, and $R_{12}$ is a radical of

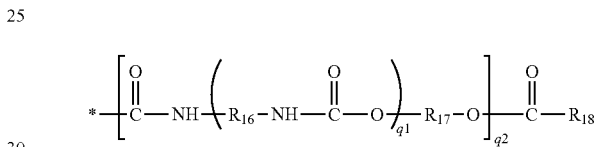

in which q2 is zero, $R_{18}$ is vinyl (*—CH=$CH_2$) or 1-methylethenyl (*—C($CH_3$)=$CH_2$).

A water-soluble, actinically-crosslinkable polyvinyl alcohol prepolymer of the invention can be prepared using techniques known in the art, e.g., those disclosed in U.S. Pat. Nos. 5,583,163 and 6,303,687 (herein incorporated by references in their entireties). Scheme 10 illustrates how to prepare a water-soluble, actinically-crosslinkable polyvinyl alcohol prepolymer of the invention according to a preferred embodiment.

Scheme 10

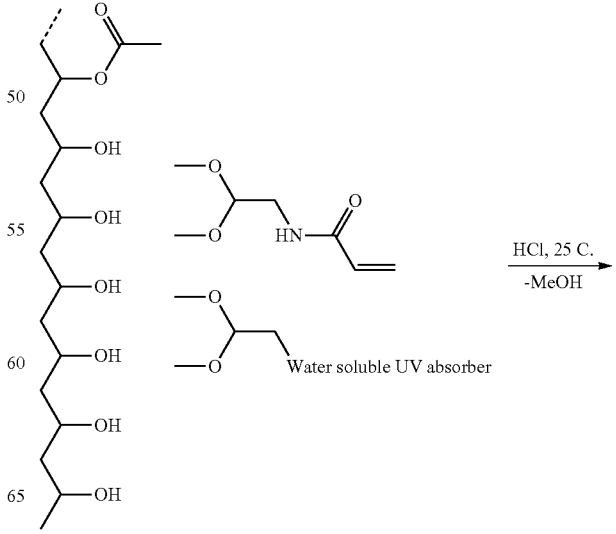

-continued

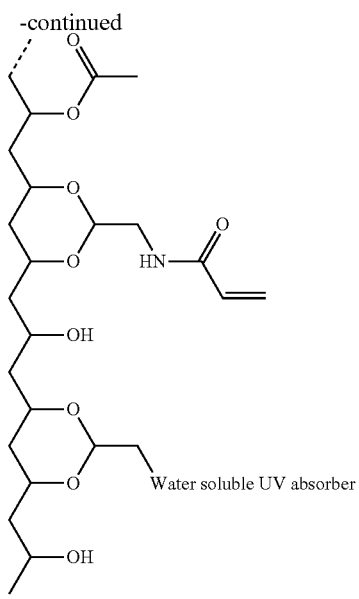

Water soluble UV absorber

Preferably, the prepolymers of the invention are purified in a manner known per se, for example by precipitation with organic solvents, such as acetone, filtration and washing, extraction in a suitable solvent, dialysis or ultrafiltration, ultrafiltration being especially preferred. By means of that purification process the prepolymers can be obtained in extremely pure form, for example in the form of concentrated aqueous solutions that are free, or at least substantially free, from reaction products, such as salts, and from starting materials, such as, for example, non-polymeric constituents.

The preferred purification process for the prepolymers used in the process according to the invention, ultrafiltration, can be carried out in a manner known per se. It is possible for the ultrafiltration to be carried out repeatedly, for example from two to ten times. Alternatively, the ultrafiltration can be carried out continuously until the selected degree of purity is attained. The selected degree of purity can in principle be as high as desired. A suitable measure for the degree of purity is, for example, the concentration of dissolved salts obtained as by-products, which can be determined simply in known manner.

It would be advantageous that the water-soluble actinically-crosslinkable polyvinyl alcohol prepolymers are in a substantially pure form (e.g., purified by ultrafiltration to remove most reactants for forming the prepolymer). Therefore, after crosslinking by actinic radiation, a contact lens may require practically no more subsequent purification, such as in particular complicated extraction of unpolymerized constituents. Furthermore, crosslinking may take place in aqueous solution, so that a subsequent solvent exchange or the hydration step is not necessary.

A water-soluble, actinically-crosslinkable polyvinyl alcohol prepolymer of the invention can find particular use for making hydrogel contact lenses.

In a further aspect, the invention provides a method for producing UV-absorbing contact lenses, comprising the steps of: (1) obtaining an aqueous lens formulation comprising (a) one or more water-soluble actinically-crosslinkable polyvinyl alcohol prepolymers as defined above and (b) (from about 0.1% to about 2.0% by weight of, preferably from about 0.25% to about 1.75% by weight of, more preferably from about 0.5% to about 1.5% by weight of, even more preferably from about 0.75% to about 1.25% by weight of) at least free-radical initiator; (2) introducing the aqueous lens formulation into a mold for making a soft contact lens, wherein the mold has a first mold half with a first molding surface defining the anterior surface of a contact lens and a second mold half with a second molding surface defining the posterior surface of the contact lens, wherein said first and second mold halves are configured to receive each other such that a cavity is formed between said first and second molding surfaces; and (3) curing thermally or actinically the aqueous lens formulation in the mold to crosslink the prepolymers and other polymerizable components in the aqueous lens formulation to form the UV-absorbing contact lens, wherein the formed UV-absorbing contact lens comprises an anterior surface defined by the first molding surface and an opposite posterior surface defined by the second molding surface and is characterized by having the UVB transmittance of about 10% or less (preferably about 5% or less, more preferably about 2.5% or less, even more preferably about 1% or less) between 280 and 315 nanometers and a UVA transmittance of about 30% or less (preferably about 20% or less, more preferably about 10% or less, even more preferably about 5% or less) between 315 and 380 nanometers and optionally (but preferably) a Violet transmittance of about 60% or less, preferably about 50% or less, more preferably about 40% or less, even more preferably about 30% or less) between 380 nm and 440 nm.

An "aqueous lens formulation" refers to a polymerizable composition which comprises water as solvent or a solvent mixture comprising at least about 60% (preferably at least about 80%, more preferably at least about 90%, even more preferably at least about 95%, most preferably at least about 98%) by weight of water relative to the total amount of the solvent mixture and polymerizable/crosslinkable components, and which can be cured (i.e., polymerized and/or crosslinked) thermally or actinically to obtain a crosslinked/polymerized polymeric material. Polymerizable components for making contact lenses are well known to a person skilled in the art, including, for example, such as, vinylic monomers, vinylic macromers, prepolymers, vinylic crosslinking agents, or combinations thereof, as known to a person skilled in the art. A lens formulation can further include other components, such as an initiator (e.g., a photoinitiator or a thermal initiator), a visibility tinting agent, photoinitiators, antimicrobial agents (e.g., Ag-nanoparticles), lubricant/wetting agents, and the like.

It is understood that the amount of UV-absorbing units present in the prepolymer in the aqueous lens formulation is sufficient to render a resultant contact lens, which is obtained from the curing of the lens formulation, ability of blocking or absorbing (i.e., the inverse of transmittance) at least 90% (preferably at least about 95%, more preferably at least about 97.5%, even more preferably at least about 99%) of UVB (between 280 and 315 nanometers), at least 70% (preferably at least about 80%, more preferably at least about 90%, even more preferably at least about 95%) of UVA transmittance (between 315 and 380 nanometers), and optionally (but preferably) at least 30% (preferably at least about 40%, more preferably at least about 50%, even more preferably at least about 60%) of violet light between 380 nm and 440 nm, which impinge on the lens.

In accordance with the invention, any thermal free-radical initiators can be used in the invention. Examples of suitable thermal initiators include, but are not limited to, 2,2'-azobis (2,4-dimethylpentanenitrile), 2,2'-azobis (2-methylpropanenitrile), 2,2'-azobis (2-methylbutanenitrile), peroxides such as benzoyl peroxide, and the like. Preferably, the thermal initiator is 2,2'-azobis(isobutyronitrile) (AIBN).

Any free-radical photoinitiators, which can absorb radiation in the range from 380 nm to 500 nm, can be used in the invention. Suitable photoinitiators are benzoin methyl ether, diethoxyacetophenone, a benzoylphosphine oxide, 1-hydroxycyclohexyl phenyl ketone and Darocur and Irgacur types, preferably Darocur 1173® and Darocur 2959®, Germanium-based Norrish Type I photoinitiators. Examples of benzoylphosphine initiators include 2,4,6-trimethylbenzoyl-diphenylophosphine oxide; bis-(2,6-dichlorobenzoyl)-4-N-propylphenylphosphine oxide; and bis-(2,6-dichlorobenzoyl)-4-N-butylphenylphosphine oxide. Reactive photoinitiators which can be incorporated, for example, into a macromer or can be used as a special monomer are also suitable. Examples of reactive photoinitiators are those disclosed in EP 632 329, herein incorporated by reference in its entirety. Most preferably, water-soluble Germanium-based Norrish Type I photoinitiators, which are disclosed in copending U.S. patent application Ser. No. _____ (herein incorporated by reference in its entirety), are used in the invention. The polymerization can then be triggered off by actinic radiation, for example, UV and/or visible light of a suitable wavelength. The spectral requirements can be controlled accordingly, if appropriate, by addition of suitable photosensitizers.

In accordance with the present invention, the aqueous lens formulation can also comprise a hydrophilic vinylic monomer. Nearly any hydrophilic vinylic monomer can be used in the invention. Suitable hydrophilic vinylic monomers are, without this being an exhaustive list, N,N-dimethylacrylamide (DMA), N,N-dimethylmethacrylamide (DMMA), 2-acrylamidoglycolic acid, N-hydroxypropylacrylamide, N-hydroxyethyl acrylamide, N-[tris(hydroxymethyl)methyl]-acrylamide, N-vinylpyrrolidone (NVP), N-vinyl formamide, N-vinyl acetamide, N-vinyl isopropylamide, N-vinyl-N-methyl acetamide (VMA), N-methyl-3-methylene-2-pyrrolidone, 1-methyl-5-methylene-2-pyrrolidone, 5-methyl-3-methylene-2-pyrrolidone, 2-hydroxyethylmethacrylate (HEMA), 2-hydroxyethyl acrylate (HEA), hydroxypropyl acrylate, hydroxypropyl methacrylate, methoxyethylmethacrylate (i.e., ethylene glycol methyl ether methacrylate, EGMA), trimethylammonium 2-hydroxy propylmethacrylate hydrochloride, aminopropyl methacrylate hydrochloride, dimethylaminoethyl methacrylate (DMAEMA), glycerol methacrylate (GMA), a $C_1$-$C_4$-alkoxy polyethylene glycol (meth)acrylate having a weight average molecular weight of up to 1500, polyethylene glycol (meth)acrylate having a weight average molecular weight of up to 1500, methacrylic acid, acrylic acid, and mixtures thereof.

An aqueous lens formulation of the invention can also comprise a non-silicone hydrophobic monomer (i.e., free of silicone). By incorporating a certain amount of non-silicone hydrophobic vinylic monomer in a lens formulation, the mechanical properties (e.g., modulus of elasticity) of the resultant polymer may be improved. Nearly any non-silicone hydrophobic vinylic monomer can be used in the actinically polymerizable composition for preparing the intermediary copolymer with pendant or terminal functional groups. Examples of preferred non-silicone hydrophobic vinylic monomers include methylacrylate, ethyl-acrylate, propylacrylate, isopropylacrylate, cyclohexylacrylate, 2-ethylhexylacrylate, methylmethacrylate, ethyl methacrylate, propylmethacrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyl toluene, vinyl ethyl ether, perfluorohexylethyl-thio-carbonyl-aminoethyl-methacrylate, isobornyl methacrylate, trifluoroethyl methacrylate, hexafluoro-isopropyl methacrylate, hexafluorobutyl methacrylate.

An aqueous lens formulation may further comprise a crosslinking agent, preferably selected from the group consisting of N,N'-methylene-bis-(meth)acrylamide, N,N'-ethylene-bis-(meth)acrylamide, N,N'-dihydroxyethylene-bis-(meth)acrylamide, 1,3-bis(methacrylamidopropyl)-1,1,3,3-tetramethyldisiloxane, ethylene glycol di(meth)acrylate, diethylene glycol di(meth)acrylate, triethylene glycol di(meth)acrylate, tetraethylene glycol di(meth)acrylate, glycerol di(meth)acrylate, triallyl isocyanurate, triallyl cyanurate, N-allyl-(meth)acrylamide, tetraethyleneglycol divinyl ether, triethyleneglycol divinyl ether, diethyleneglycol divinyl ether, ethyleneglycol divinyl ether, and combinations thereof.

It is understood that although the aqueous lens formulation can include one or more vinylic monomers, and/or one or more crosslinking agents. However, the amount of those components should be low such that the final contact lens does not contain unacceptable levels of unpolymerized monomers, macromers and/or crosslinking agents. The presence of unacceptable levels of unpolymerized monomers and/or crosslinking agents will require extraction to remove them, which requires additional steps that are costly and inefficient.

An aqueous lens formulation of the invention can further comprise visibility tinting agents (e.g., D&C Blue No. 6, D&C Green No. 6, D&C Violet No. 2, carbazole violet, certain copper complexes, certain chromium oxides, various iron oxides, phthalocyanine green, phthalocyanine blue, titanium dioxides, or mixtures thereof), antimicrobial agents (e.g., silver nanoparticles), a bioactive agent (e.g., a drug, an amino acid, a polypeptide, a protein, a nucleic acid, 2-pyrrolidone-5-carboxylic acid (PCA), an alpha hydroxyl acid, linoleic and gamma linoleic acids, vitamins, or any combination thereof), leachable lubricants (e.g., a non-crosslinkable hydrophilic polymer having an average molecular weight from 5,000 to 500,000, preferably from 10,000 to 300,000, more preferably from 20,000 to 100,000 Daltons), leachable tear-stabilizing agents (e.g., a phospholipid, a monoglyceride, a diglyceride, a triglyceride, a glycolipid, a glyceroglycolipid, a sphingolipid, a sphingo-glycolipid, a fatty acid having 8 to 36 carbon atoms, a fatty alcohol having 8 to 36 carbon atoms, or a mixture thereof), and the like, as known to a person skilled in the art.

An aqueous lens formulation can be prepared by dissolving all of the desirable components in water or a mixture of water and an organic solvent known to a person skilled in the art.

Lens molds for making contact lenses are well known to a person skilled in the art. Methods of manufacturing mold sections for cast-molding a contact lens are generally well known to those of ordinary skill in the art. The process of the present invention is not limited to any particular method of forming a mold. In fact, any method of forming a mold can be used in the present invention. The first and second mold halves can be formed through various techniques, such as injection molding or lathing. Examples of suitable processes for forming the mold halves are disclosed in U.S. Pat. No. 4,444,711 to Schad; U.S. Pat. No. 4,460,534 to Boehm et al.; U.S. Pat. No. 5,843,346 to Morrill; and U.S. Pat. No. 5,894,002 to Boneberger et al., which are also incorporated herein by reference. Virtually all materials known in the art for making molds can be used to make molds for making contact lenses. For example, polymeric materials, such as polyethylene, polypropylene, polystyrene, PMMA, Topas® COC grade 8007-S10 (clear amorphous copolymer of ethylene and norbornene, from Ticona GmbH of Frankfurt, Germany and Summit, N.J.), or the like can be used. Other materials that allow UV light transmission could be used, such as quartz glass and sapphire.

Preferably, a reusable mold suitable for spatial limitation of radiation is used in the invention, the projected beam of radiation (e.g., radiation from the light source including the light in the region of 360 nm to 550 nm) limits radiation (e.g., UV radiation) impinging on the mixture of the lens-forming materials located in the path of the projected beam from the first molding surface to the second molding surface of the reusable mold. The resultant contact lens comprises an anterior surface defined by the first molding surface, an opposite posterior surface defined by the second molding surface, and a lens edge (with sharp edge and high quality) defined by the sectional profile of the projected radiation beam (i.e., a spatial limitation of radiation). Examples of reusable molds suitable for spatial limitation of radiation include without limitation those disclosed in U.S. Pat. Nos. 6,627,124, 6,800,225, 7,384,590, and 7,387,759, which are incorporated by reference in their entireties.

For example, a preferred reusable mold comprises a first mold half having a first molding surface and a second mold half having a second molding surface. The two mold halves of the preferred reusable mold are not touching each other, but there is a thin gap of annular design arranged between the two mold halves. The gap is connected to the mold cavity formed between the first and second molding surfaces, so that excess mixture can flow into the gap. It is understood that gaps with any design can be used in the invention.

In a preferred embodiment, at least one of the first and second molding surfaces is permeable to a crosslinking radiation. More preferably, one of the first and second molding surfaces is permeable to a crosslinking radiation while the other molding surface is poorly permeable to the crosslinking radiation.

The reusable mold preferably comprises a mask which is fixed, constructed or arranged in, at or on the mold half having the radiation-permeable molding surface. The mask is impermeable or at least of poor permeability compared with the permeability of the radiation-permeable molding surface. The mask extends inwardly right up to the mold cavity and surrounds the mold cavity so as to screen all areas behind the mask with the exception of the mold cavity.

The mask may preferably be a thin chromium layer, which can be produced according to processes as known, for example, in photo and UV lithography. Other metals or metal oxides may also be suitable mask materials. The mask can also be coated with a protective layer, for example of silicon dioxide if the material used for the mold or mold half is quartz.

Alternatively, the mask can be a masking collar made of a material comprising a UV/visible light-absorber and substantially blocks curing energy therethrough as described in U.S. Pat. No. 7,387,759 (incorporated by reference in its entirety). In this preferred embodiment, the mold half with the mask comprises a generally circular disc-shaped transmissive portion and a masking collar having an inner diameter adapted to fit in close engagement with the transmissive portion, wherein said transmissive portion is made from an optically clear material and allows passage of curing energy therethrough, and wherein the masking collar is made from a material comprising a light-blocker and substantially blocks passage of curing energy therethrough, wherein the masking collar generally resembles a washer or a doughnut, with a center hole for receiving the transmissive portion, wherein the transmissive portion is pressed into the center opening of the masking collar and the masking collar is mounted within a bushing sleeve.

Reusable molds can be made of quartz, glass, sapphire, $CaF_2$, a cyclic olefin copolymer (such as for example, Topas® COC grade 8007-S10 (clear amorphous copolymer of ethylene and norbornene) from Ticona GmbH of Frankfurt, Germany and Summit, N.J., Zeonex® and Zeonor® from Zeon Chemicals LP, Louisville, Ky.), polymethylmethacrylate (PMMA), polyoxymethylene from DuPont (Delrin), Ultem® (polyetherimide) from G.E. Plastics, PrimoSpire®, etc. Because of the reusability of the mold halves, a relatively high outlay can be expended at the time of their production in order to obtain molds of extremely high precision and reproducibility. Since the mold halves do not touch each other in the region of the lens to be produced, i.e. the cavity or actual molding surfaces, damage as a result of contact is ruled out. This ensures a high service life of the molds, which, in particular, also ensures high reproducibility of the contact lenses to be produced and high fidelity to the lens design.

In accordance with the invention, the lens formulation can be introduced (dispensed) into a cavity formed by a mold according to any known methods.

After the lens formulation is dispensed into the mold, it is polymerized to produce a contact lens. Crosslinking may be initiated thermally or upon exposure to a light source including a light in a region between 390 nm to 500 nm, preferably under a spatial limitation of actinic radiation, to crosslink the polymerizable components in the mixture.

In accordance with the invention, light source can be any ones emitting light in the 390-500 nm range sufficient to activate Germane-based Norrish Type I photoinitiators. Blue-light sources are commercially available and include: the Palatray CU blue-light unit (available from Heraeus Kulzer, Inc., Irvine, Calif.), the Fusion F450 blue light system (available from TEAMCO, Richardson, Tex.), Dymax Blue Wave 200, LED light sources from Opsytec (385 nm, 395 nm, 405 nm, 435 nm, 445 nm, 460 nm), LED light sources from Hamamatsu (385 nm), and the GE 24" blue fluorescent lamp (available from General Electric Company, U.S.). A preferred blue-light source is the UV LED from Opsytec (those described above).

The intensity of the light source is preferably from about 4 to about 40 mW/cm$^2$, preferably from about 8 to about 16 mW/cm$^2$ in the 400 nm to 550 nm region is more preferred.

The photocrosslinking according to the invention may be effected in a very short time, e.g. in ≤ about 120 seconds, preferably in ≤ about 80 seconds, more preferably in ≤50 about seconds, even more preferably in about 30 seconds, and most preferably in 5 to 30 seconds.

Opening of the mold so that the molded lens can be removed from the mold may take place in a manner known per se.

The molded contact lens can be subject to lens extraction to remove unpolymerized vinylic monomers and macromers. The extraction solvent is preferably water or an aqueous solution. After extraction, lenses can be hydrated in water or an aqueous solution of a wetting agent (e.g., a hydrophilic polymer); packaged in lens packages with a packaging solution which can contain about 0.005% to about 5% by weight of a wetting agent (e.g., a hydrophilic polymer), a viscosity-enhancing agent (e.g., methyl cellulose (MC), ethyl cellulose, hydroxymethylcellulose, hydroxyethyl cellulose (HEC), hydroxypropylcellulose (HPC), hydroxypropylmethyl cellulose (HPMC), or a mixture thereof); sterilization such as autoclave at from 118 to 124° C. for at least about 30 minutes; and the like.

In still a further aspect, the invention provides a hydrogel contact lens comprising a crosslinked polymeric material which is a crosslinking product of at least one water-soluble actinically-crosslinkable polyvinyl alcohol prepolymer as defined above in the presence or absence of a vinylic monomer and/or vinylic crosslinking agent.

A contact lens of the invention preferably is characterized by having an UVB transmittance of about 10% or less (preferably about 5% or less, more preferably about 2.5% or less, even more preferably about 1% or less) between 280 and 315 nanometers and a UVA transmittance of about 30% or less (preferably about 20% or less, more preferably about 10% or less, even more preferably about 5% or less) between 315 and 380 nanometers and optionally (but preferably) a Violet transmittance of about 60% or less, preferably about 50% or less, more preferably about 40% or less, even more preferably about 30% or less) between 380 nm and 440 nm.

A contact lens of the invention further has a water content of preferably from about 15% to about 80%, more preferably from about 30% to about 70% by weight (at room temperature, about 22° C. to 28° C.) when fully hydrated.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part or can be combined in any manner and/or used together, as illustrated below:

1. An acetal-containing, UV-absorbing compound of any one of formula (I) to (V)

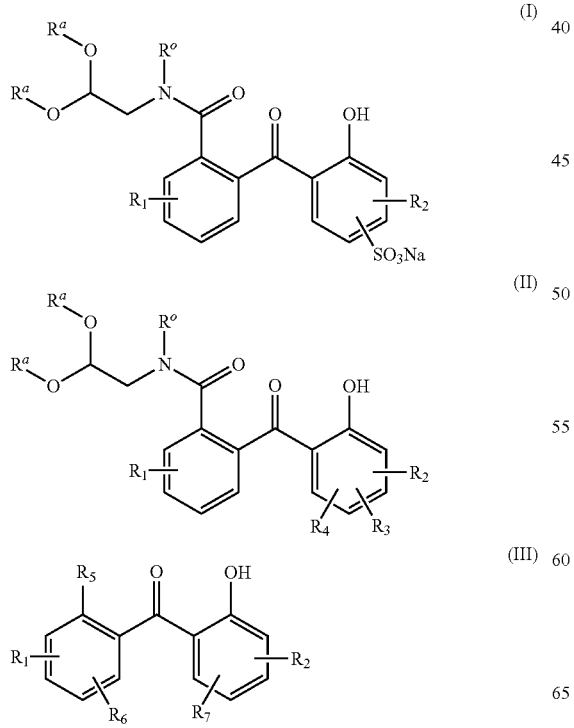

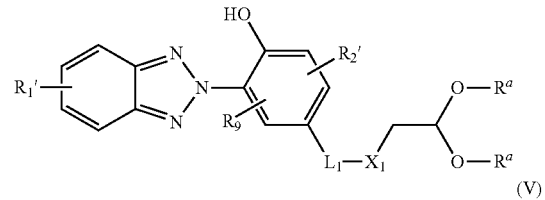

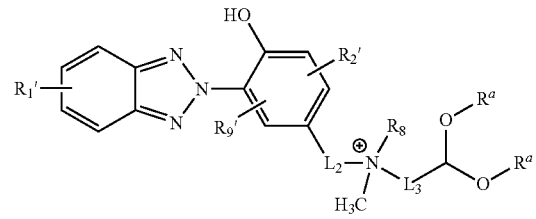

in which:
$R^a$ is $CH_3$ or $C_2H_5$;
$R^o$ is H or $CH_3$;
$R_1$, $R_2$ and $R_2'$ independent of one other are H, $CH_3$, $CCl_3$, $CF_3$, Cl, Br, NR'R" in which R' and R" independent of each other are H or $C_1$-$C_4$ alkyl, OH, or $OCH_3$;
$R_1'$ independent of each other are H, $CH_3$, $CCl_3$, $CF_3$, Cl, Br, NR'R" in which R' and R" independent of each other are H or $C_1$-$C_4$ alkyl, OH, $OCH_3$, $SO_3H$, or $SO_3^-Na^+$;
$R_3$ and $R_4$ independent of each other are H or a first hydrophilic group which is

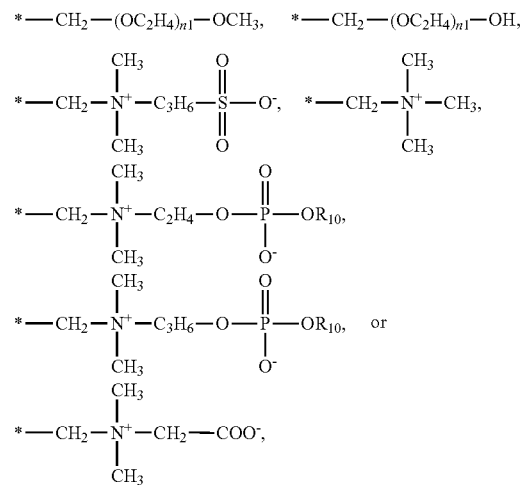

provided that at least one of $R_3$ and $R_4$ is the first hydrophilic group;
r1 is an integer of 1 to 8;
n1 is an integer of 2 to 20;
$R_5$ is H, *—COOH, *—CONH—$C_2H_4$—$(OC_2H_4)_{n1}$—$OCH_3$, or *—CONH—$C_2H_4$—$(OC_2H_4)_{n1}$—OH;
one of $R_6$ and $R_7$ is H or a second hydrophilic group which is

*—$CH_2$—$(OC_2H_4)_{n1}$—$OCH_3$, *—$CH_2$—$(OC_2H_4)_{n1}$—OH,

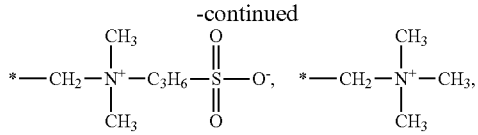
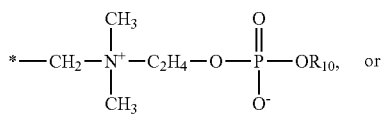
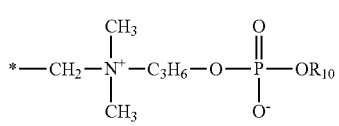
while the other of $R_6$ and $R_7$ is
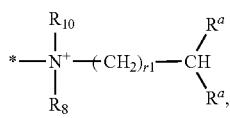
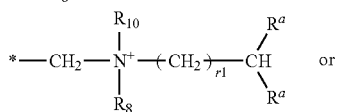
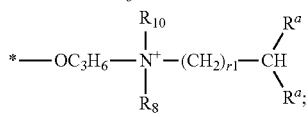
$R_8$ is $CH_3$, $C_2H_5$,
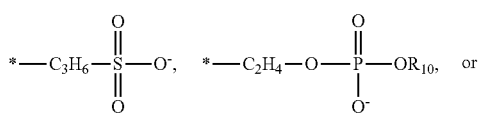
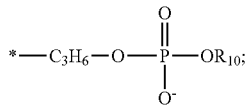
$R_9$ is $SO_3Na$,
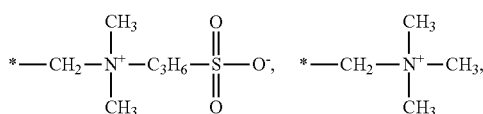
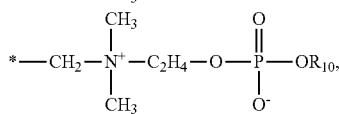
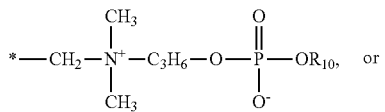
$R_9'$ is H, $SO_3Na$,
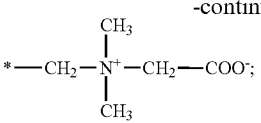
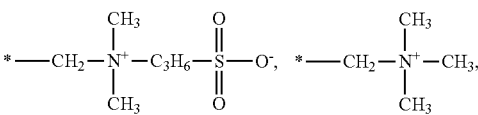
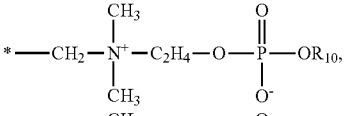
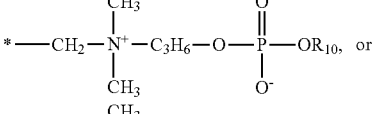
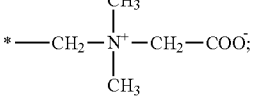
$R_{10}$ is methyl or ethyl;
L1 is a linkage of
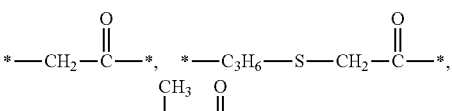
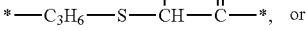
L2 is a linkage of
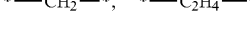
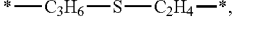
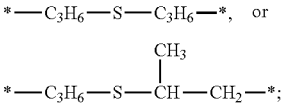
L3 is a linkage of
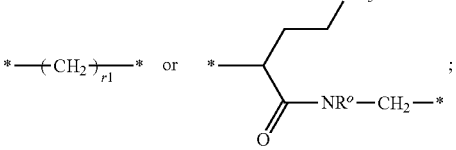
and
X1 is O or $NR^o$.
2. The acetal-containing, UV-absorbing compound of invention 1, wherein r1 is an integer of 3 to 6.

3. The acetal-containing, UV-absorbing compound of invention 1 or 2, wherein n1 is an integer of 3 to 15 (preferably 4 to 10).

4. The acetal-containing, UV-absorbing compound according to any one of inventions 1 to 3, wherein the acetal-containing, UV-absorbing compound is defined by formula (I).

5. The acetal-containing, UV-absorbing compound of invention 4, wherein the acetal-containing, UV-absorbing compound is further defined by

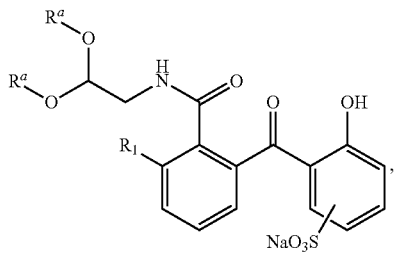

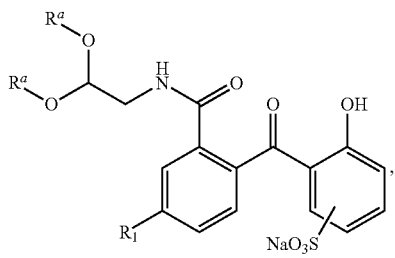

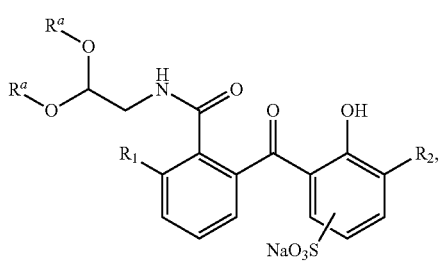

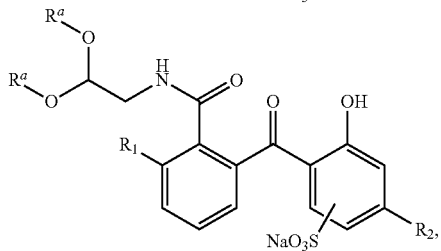

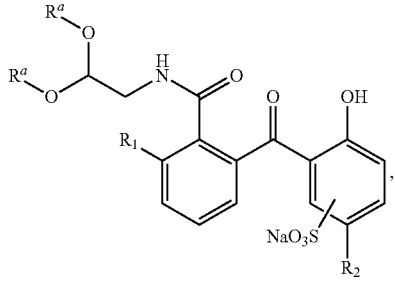

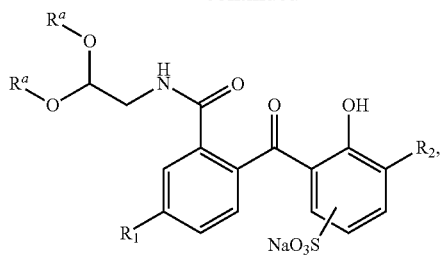

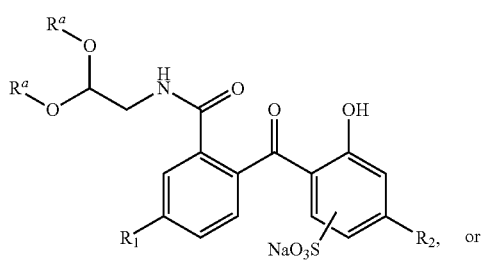

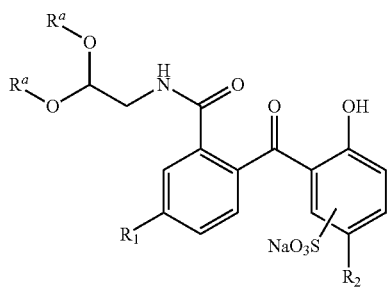

in which $R^a$ is methyl or ethyl, $R_1$ and $R_2$ independent of each other are H, $CH_3$, $CCl_3$, $CF_3$, Cl, Br, NR'R", OH, or $OCH_3$, in which R' and R" independent of each other are H, methyl or ethyl.

6. The acetal-containing, UV-absorbing compound according to any one of inventions 1 to 3, wherein the acetal-containing, UV-absorbing compound is defined by formula (II).

7. The acetal-containing, UV-absorbing compound of invention 6, wherein the acetal-containing, UV-absorbing compound is further defined by

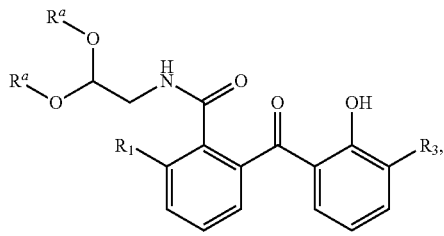

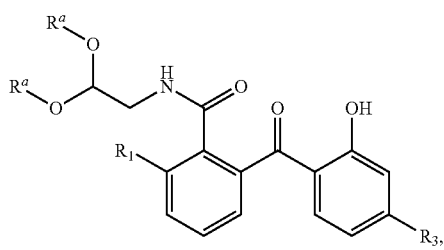

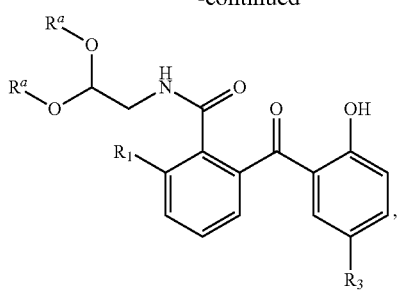
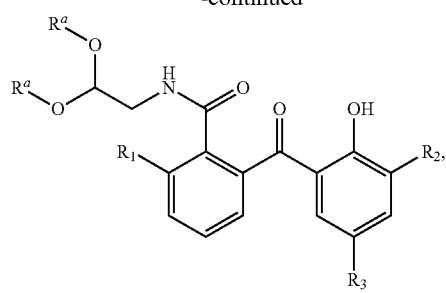
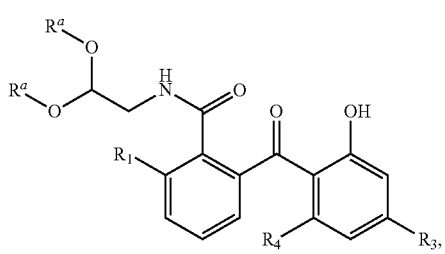
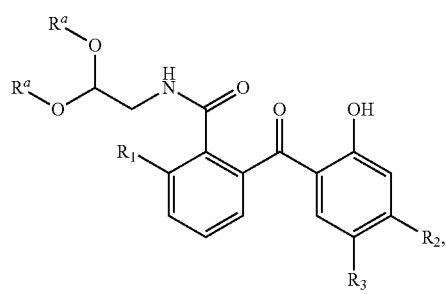
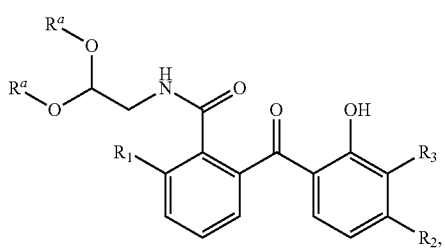
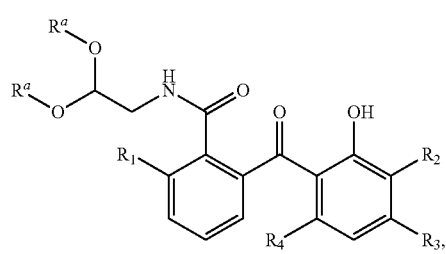
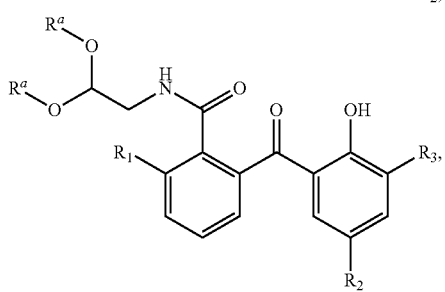
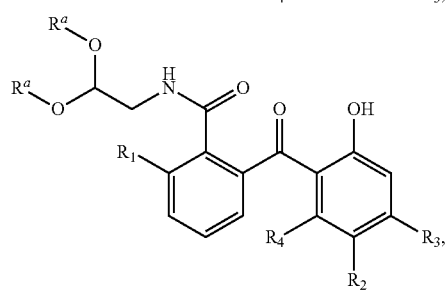
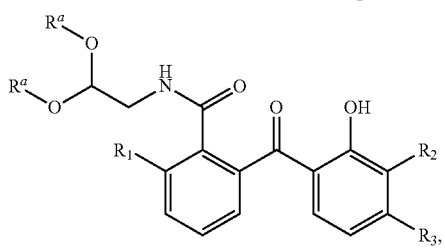
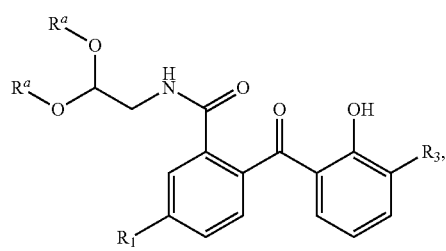
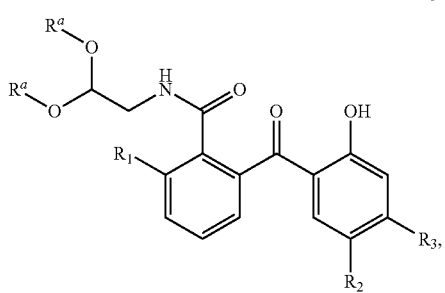
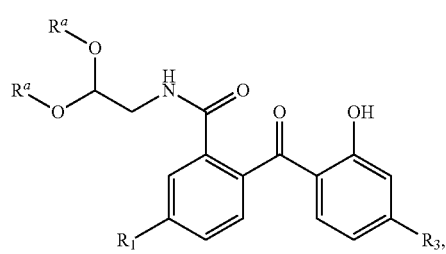

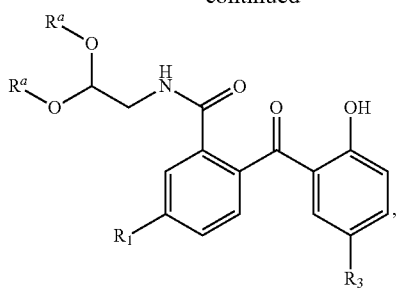
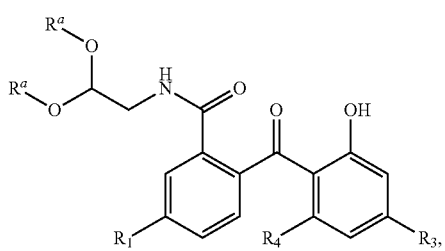
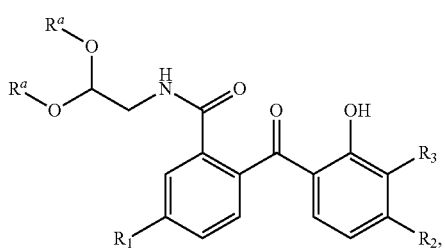
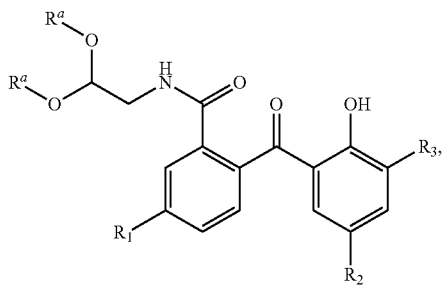
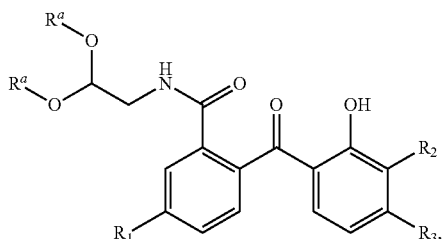
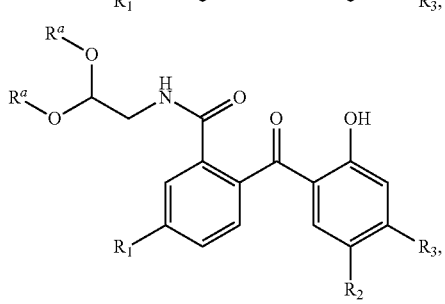
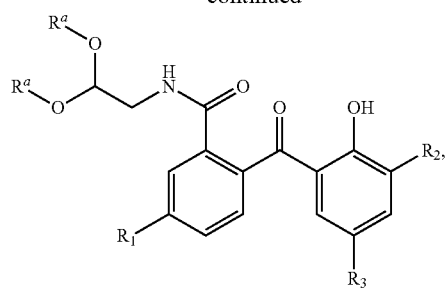
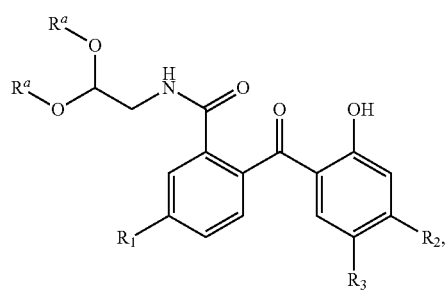
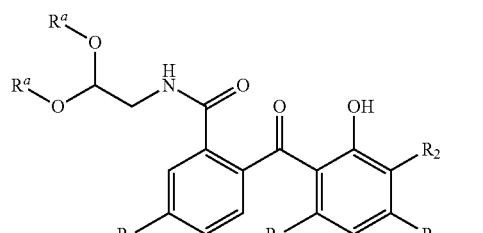
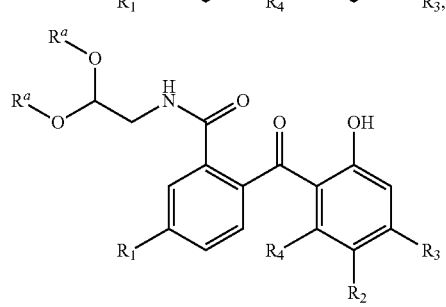
in which: $R^a$ is methyl or ethyl; $R_1$ and $R_2$ independent of each other are $CH_3$, $CCl_3$, $CF_3$, Cl, Br, NR'R", OH, or $OCH_3$; R' and R" independent of each other are H, methyl or ethyl; $R_3$ and $R_4$ independent of each other are
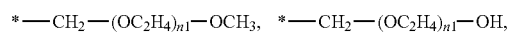
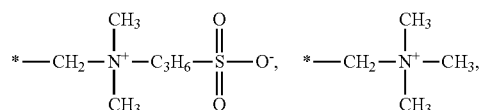
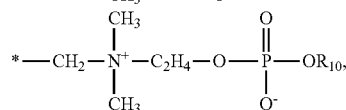
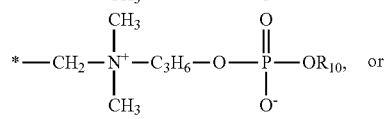

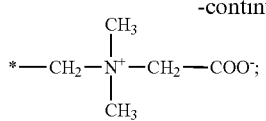
$R_{10}$ is methyl or ethyl.
8. The acetal-containing, UV-absorbing compound according to any one of inventions 1 to 3, wherein the acetal-containing, UV-absorbing compound is defined by formula (III).
9. The acetal-containing, UV-absorbing compound of invention 8, wherein the acetal-containing, UV-absorbing compound is further defined by
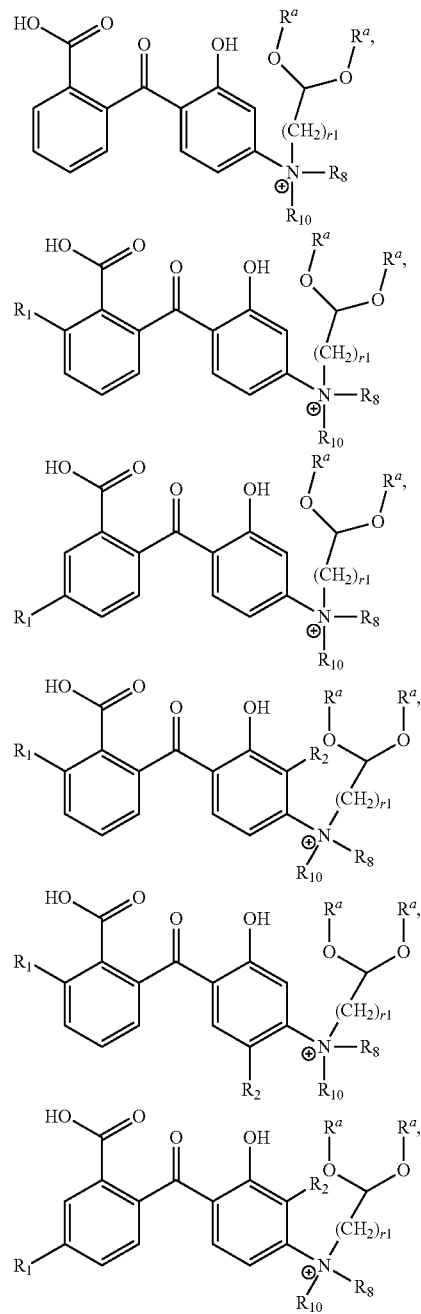
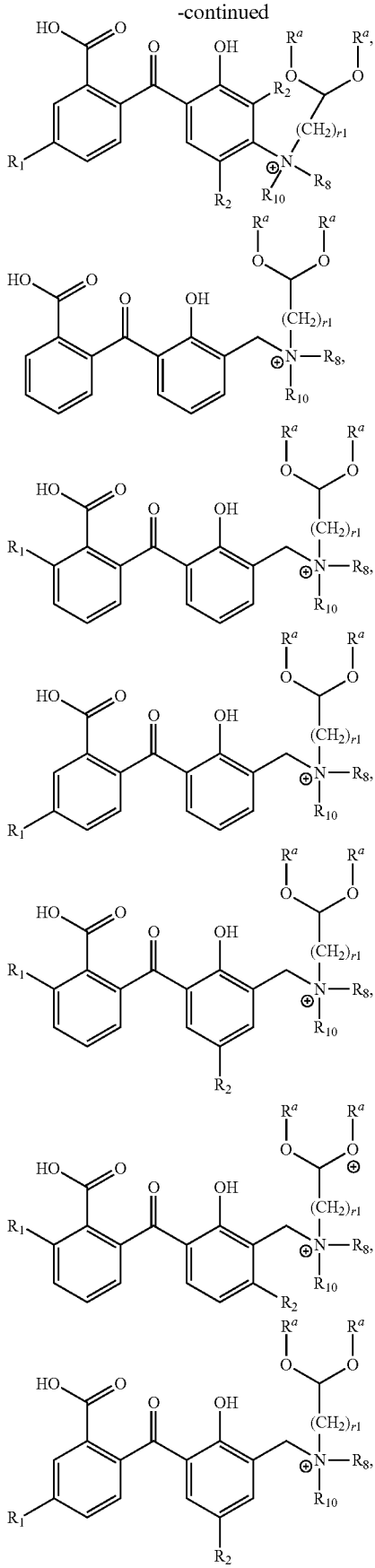

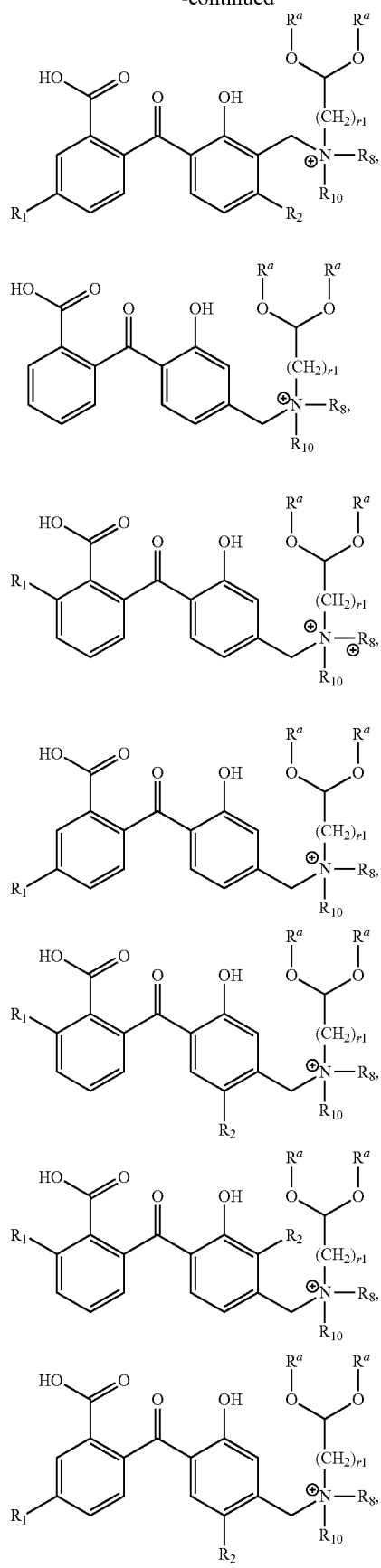
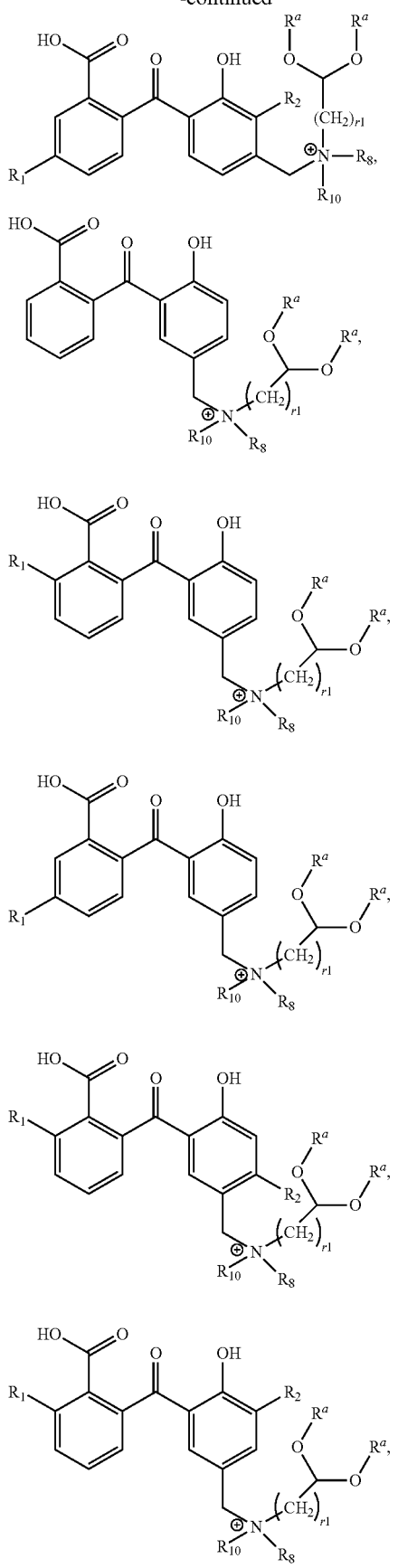

61
-continued
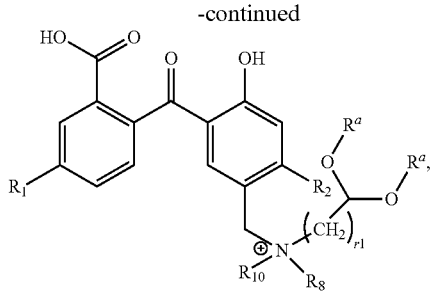
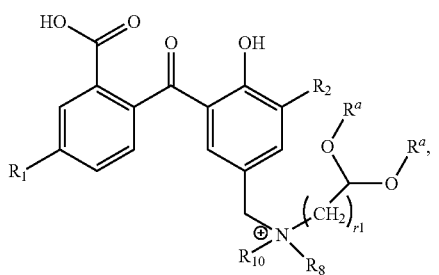
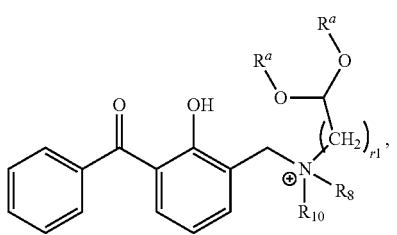
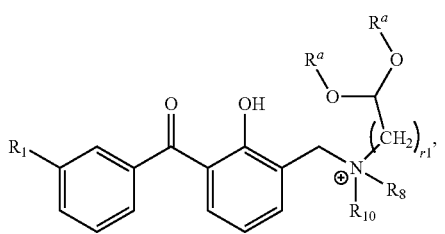
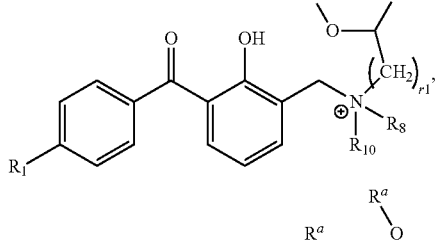
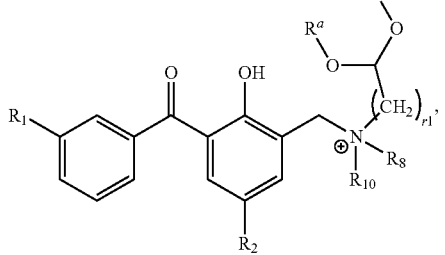
62
-continued
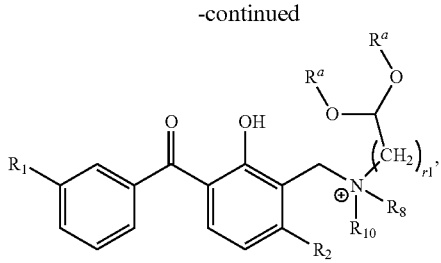
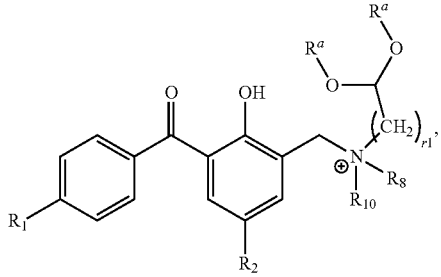
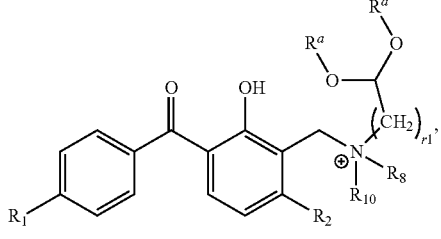
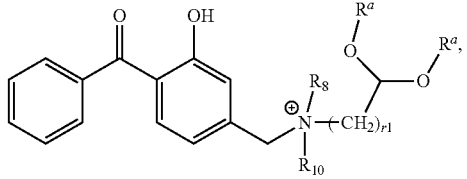
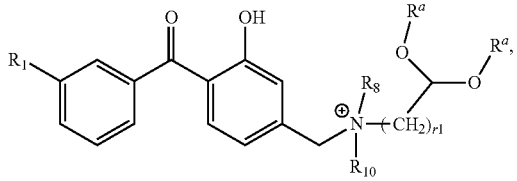
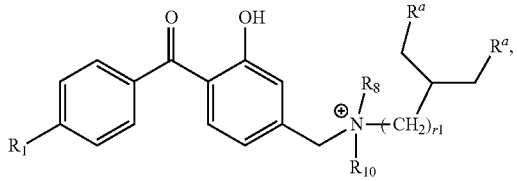
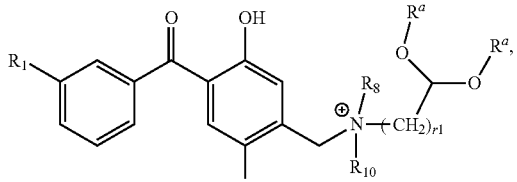
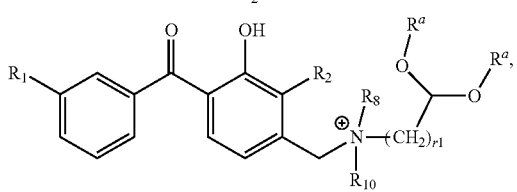

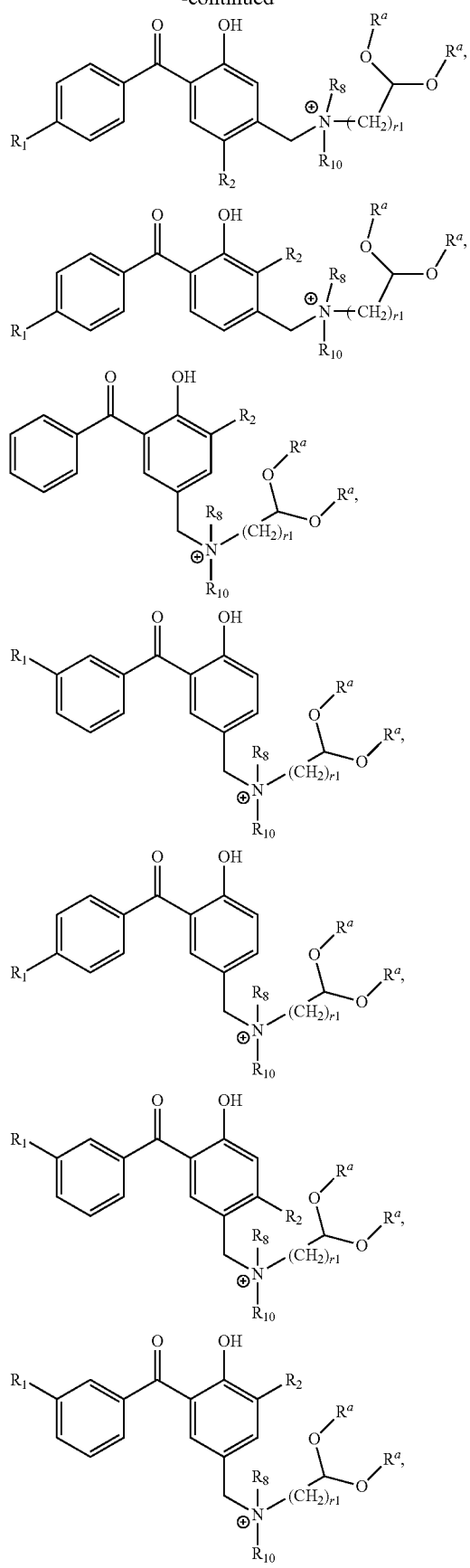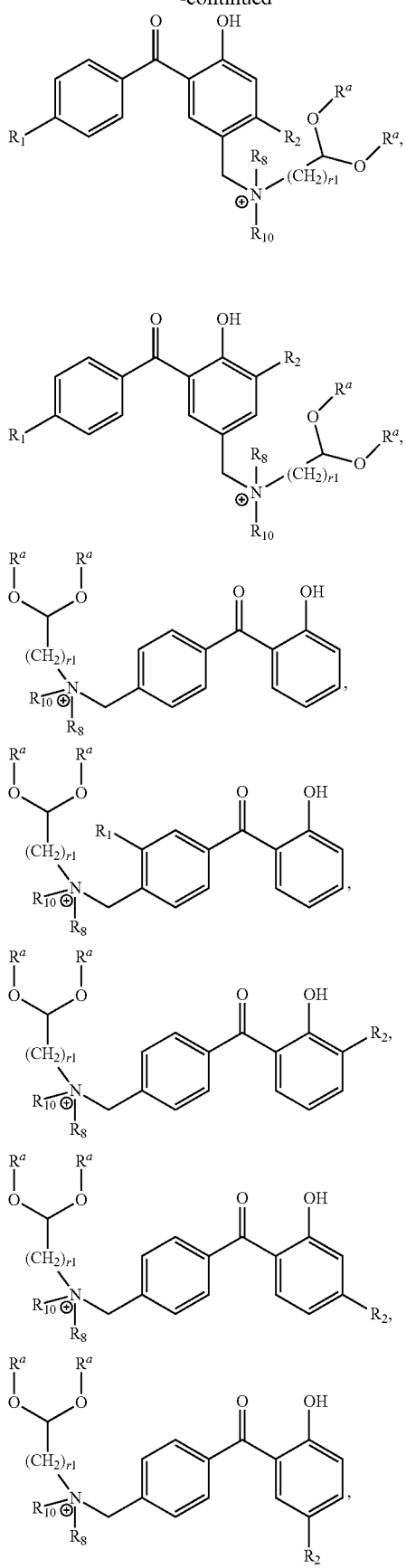

-continued

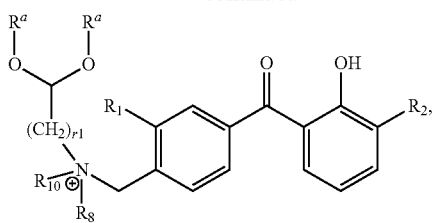

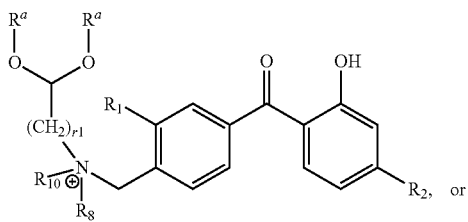

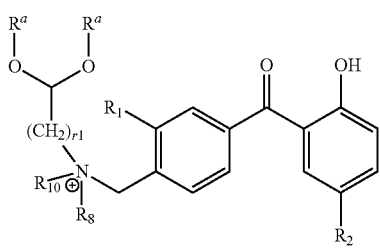

in which: $R^a$ is methyl or ethyl; $R_1$ and $R_2$ independent of each other are $CH_3$, $CCl_3$, $CF_3$, Cl, Br, NR'R" OH, or $OCH_3$; in which R' and R" independent of each other are H or $C_1$-$C_4$ alkyl; $R_8$ is $CH_3$, $C_2H_5$,

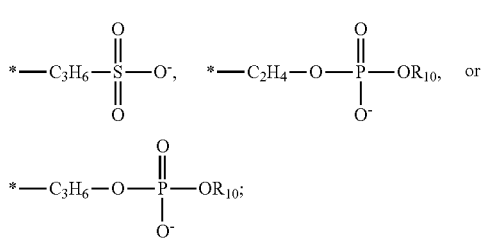

$R_{10}$ is methyl or ethyl; and r1 is an integer of 3 to 6.

10. The acetal-containing, UV-absorbing compound according to any one of inventions 1 to 3, wherein the acetal-containing, UV-absorbing compound is defined by formula (IV).

11. The acetal-containing, UV-absorbing compound of invention 10, wherein the acetal-containing, UV-absorbing compound is further defined by

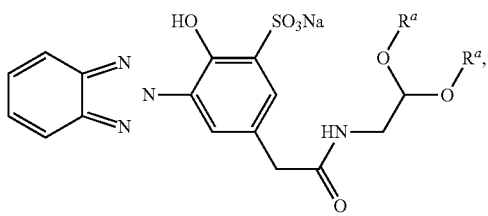

-continued

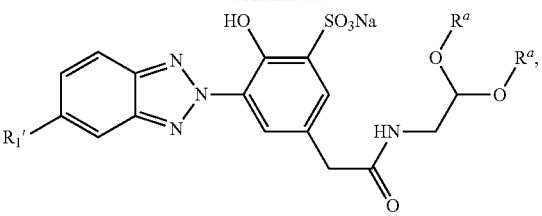

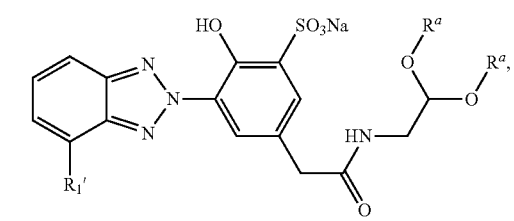

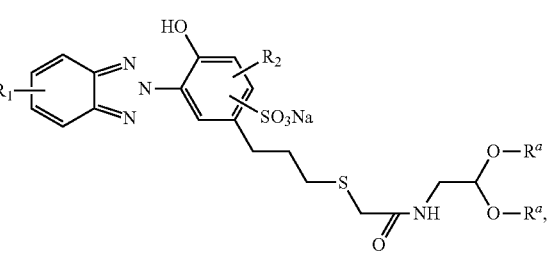

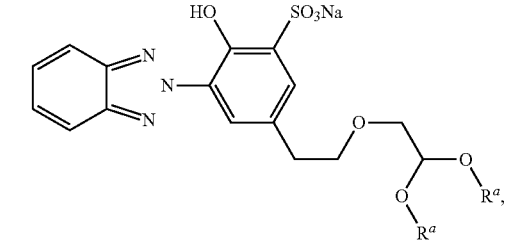

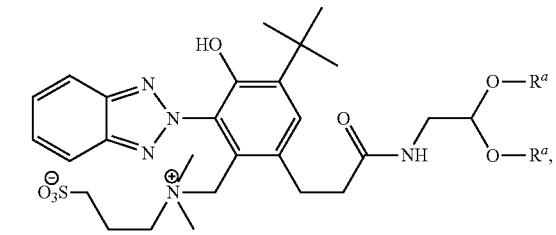

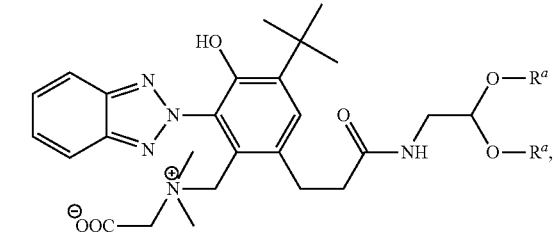

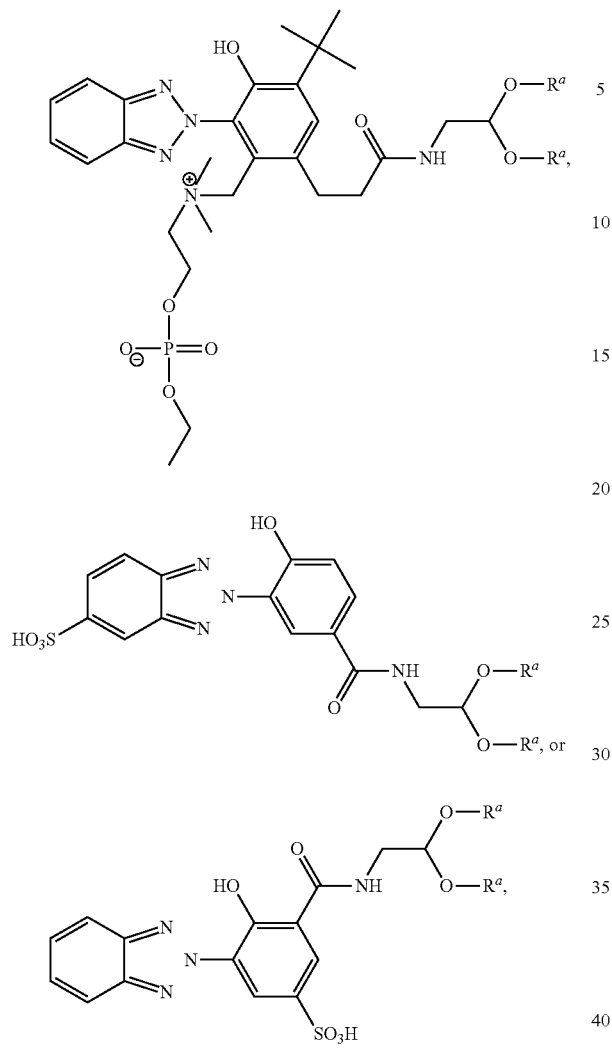

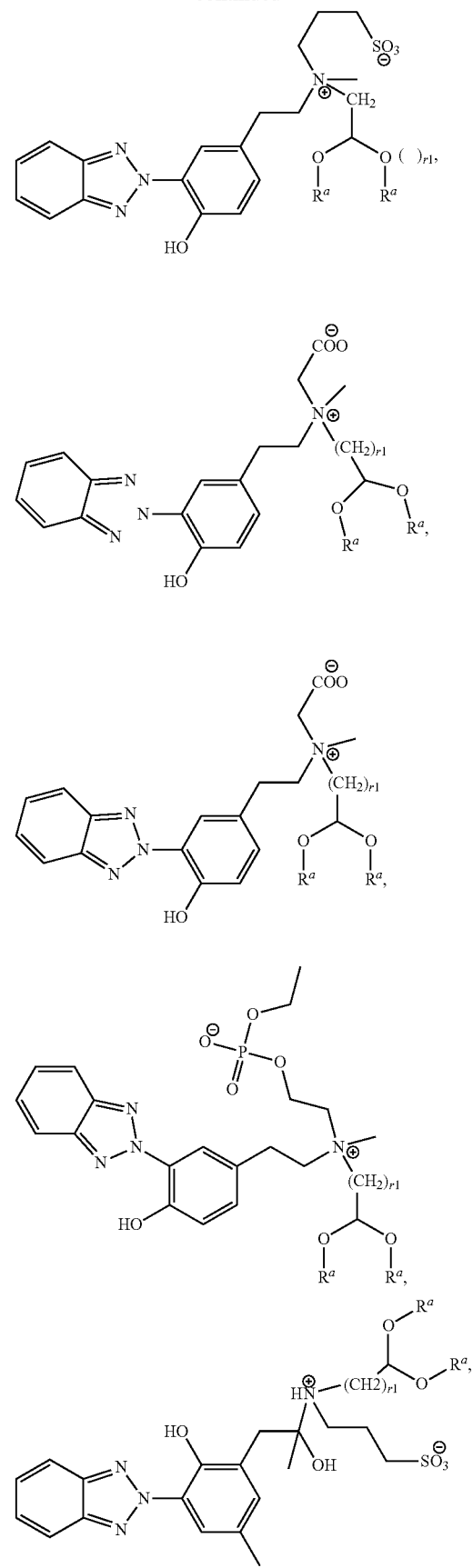

in which $R^a$ is methyl or ethyl; $R^o$ is H or $CH_3$; $R_1$ and $R_2$ independent of each other are H, $CH_3$, $CCl_3$, $CF_3$, Cl, Br, NR'R" in which R' and R" independent of each other are H or $C_1$-$C_4$ alkyl, OH, or $OCH_3$.

12. The acetal-containing, UV-absorbing compound according to any one of inventions 1 to 3, wherein the acetal-containing, UV-absorbing compound is defined by formula (V).

13. The acetal-containing, UV-absorbing compound of invention 12, wherein the acetal-containing, UV-absorbing compound is further defined by

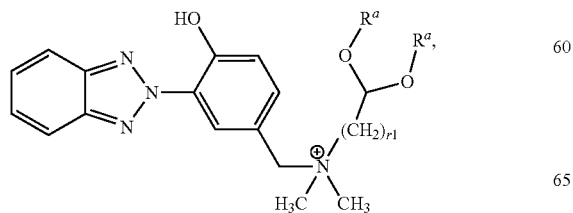

-continued
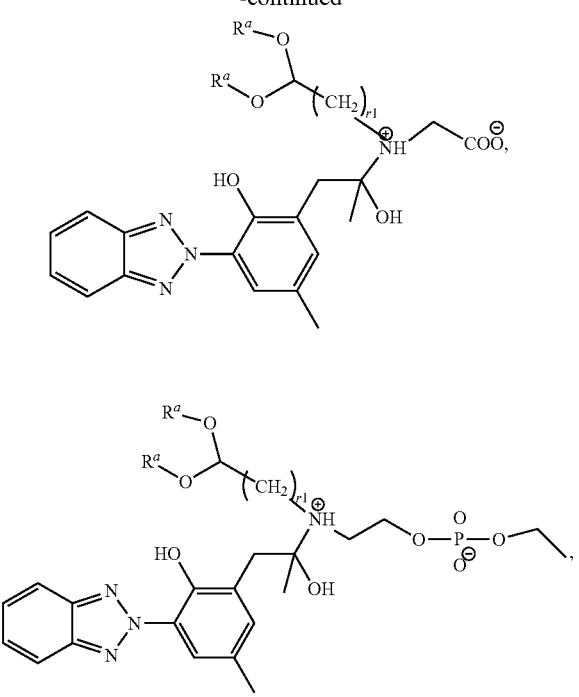
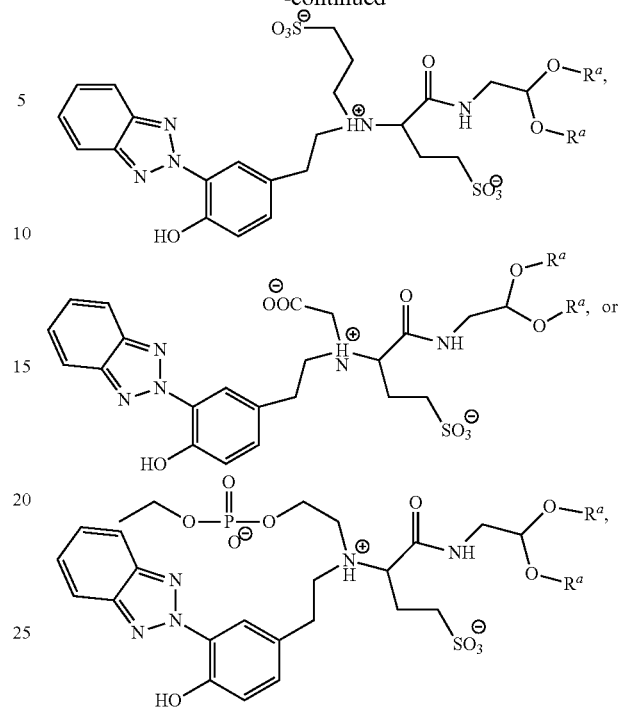
in which $R^a$ is methyl or ethyl, r1 is an integer of 3 to 6, and $Z=CH_3$ or COOH.
14. A water-soluble, actinically-crosslinkable polyvinyl alcohol prepolymer, comprising: repeating units of vinyl alcohol (i.e.,
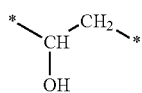
);
repeating crosslinking units of formula (VI); and
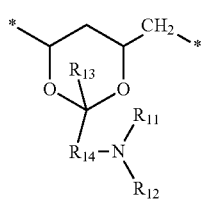  (VI)
repeating UV-absorbing units of formula (VII)
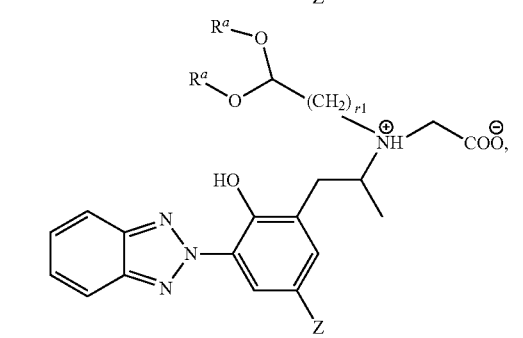
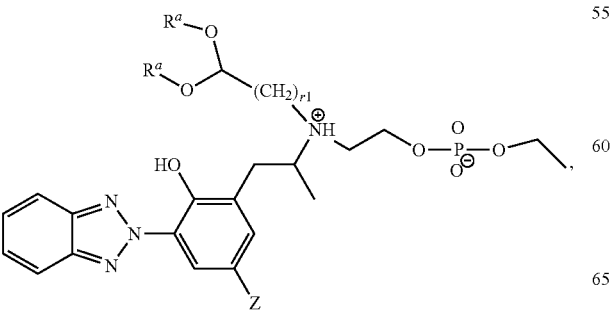
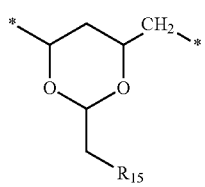  (VII)

in which:

$R_{11}$ is hydrogen or $C_1$-$C_6$ alkyl;

$R_{12}$ is an ethylenically unsaturated group of

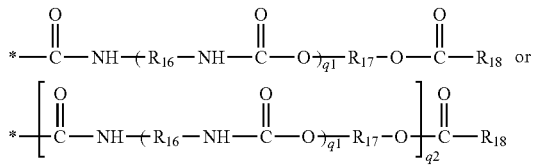

in which q1 and q2 independently of each another are zero or one, and $R_{16}$ and $R_{17}$ independently of one another are a $C_2$-$C_8$ alkylene divalent radical, $R_{18}$ is $C_2$-$C_8$ alkenyl;

$R_{13}$ can be hydrogen or a $C_1$-$C_6$ alkyl group;

$R_{14}$ is a $C_1$-$C_6$ alkylene divalent radical;

$R_{15}$ is a monovalent radical of any one of formula (VIII)-(XII)

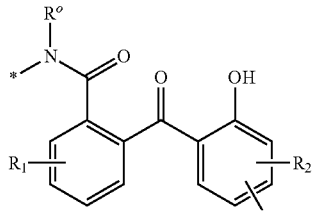
(VIII)

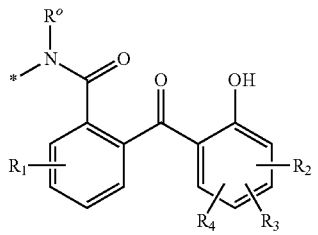
(IX)

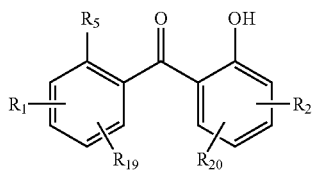
(X)

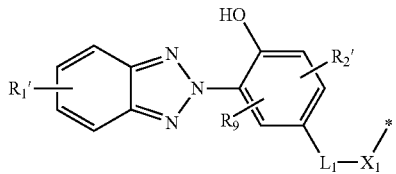
(XI)

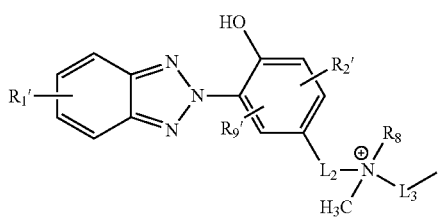
(XII)

$R^o$ is H or $CH_3$;

$R_1$, $R_2$ and $R_2'$ independent of one other are H, $CH_3$, $CCl_3$, $CF_3$, Cl, Br, NR'R" in which R' and R" independent of each other are H or $C_1$-$C_4$ alkyl, OH, or $OCH_3$;

$R_1'$ independent of each other are H, $CH_3$, $CCl_3$, $CF_3$, Cl, Br, NR'R" in which R' and R" independent of each other are H or $C_1$-$C_4$ alkyl, OH, $OCH_3$, $SO_3H$, or $SO_3^-Na^+$;

$R_3$ and $R_4$ independent of each other are H or a first hydrophilic group which is

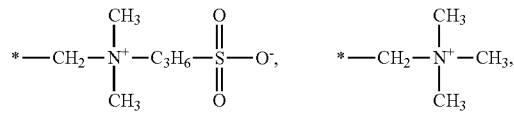

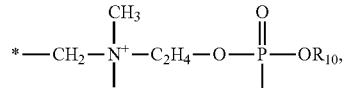

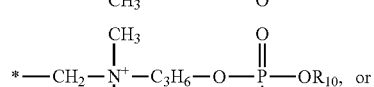

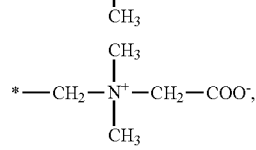

provided that at least one of $R_3$ and $R_4$ is the first hydrophilic group;

r1 is an integer of 1 to 8;

n1 is an integer of 2 to 20;

$R_5$ is H, *—COOH, *—CONH—$C_2H_4$—$(OC_2H_4)_{n1}$—$OCH_3$, or *—CONH—$C_2H_4$—$(OC_2H_4)_{n1}$—OH;

$R_8$ is $CH_3$, $C_2H_5$,

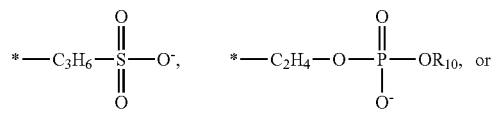

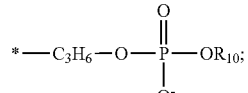

$R_9$ is $SO_3Na$,

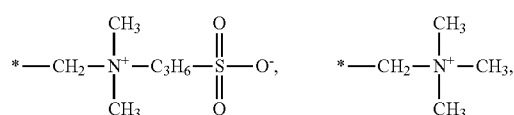

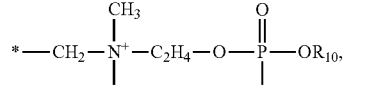

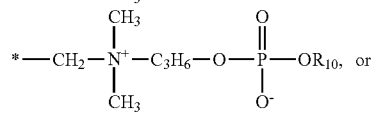

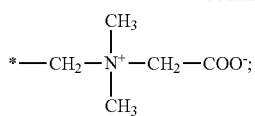

$R_9'$ is H, $SO_3Na$,

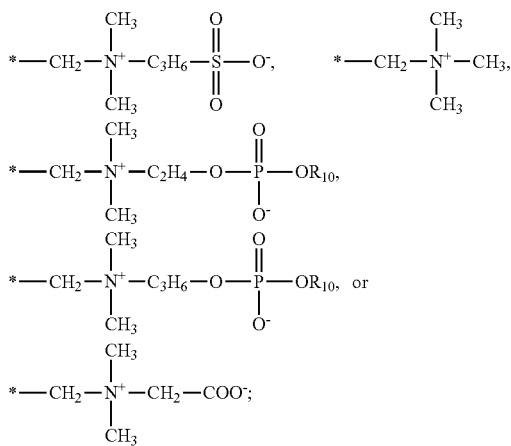

$R_{10}$ is methyl or ethyl;

L1 is a linkage of

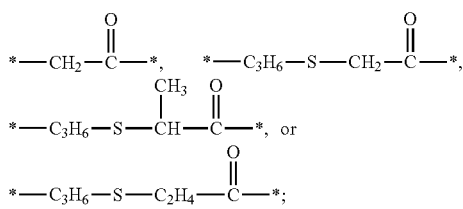

L2 is a linkage of

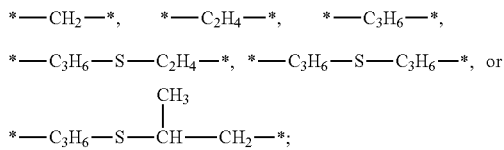

L3 is a linkage of

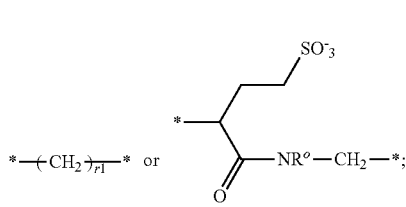

X1 is O or $NR^o$;

one of $R_{19}$ and $R_{20}$ is H or a second hydrophilic group which is

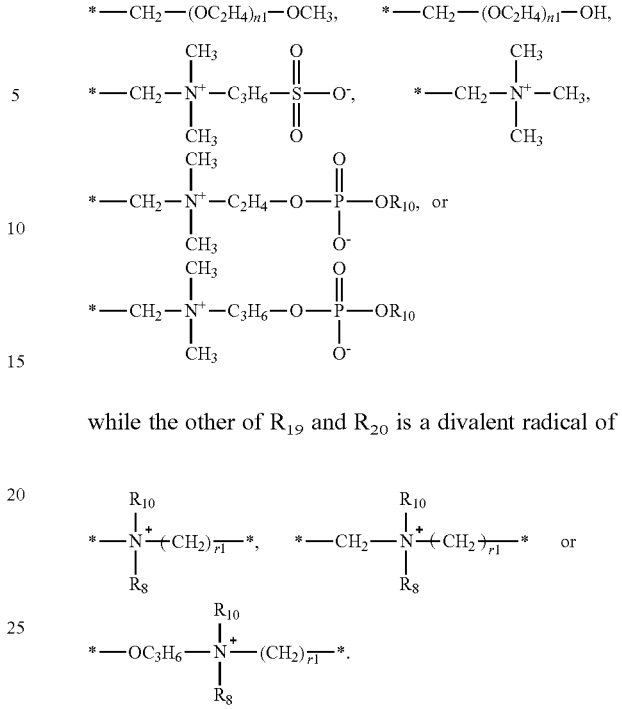

while the other of $R_{19}$ and $R_{20}$ is a divalent radical of

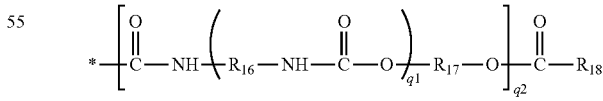

15. The prepolymer of invention 14, wherein $R_{11}$ is hydrogen or $C_1$-$C_4$ alkyl (preferably hydrogen or methyl or ethyl, more preferably hydrogen or methyl).

16. The prepolymer of invention 14 or 15, wherein $R_{13}$ is hydrogen.

17. The prepolymer of invention 14, 15 or 16, wherein $R_{14}$ is a $C_1$-$C_4$ alkylene divalent radical (preferably methylene or butylene divalent radical, more preferably methylene divalent radical).

18. The prepolymer of any one of inventions 14 to 17, wherein r1 is an integer of 3 to 6.

19. The prepolymer of any one of inventions 14 to 18, wherein n1 is an integer of 3 to 15 (preferably 4 to 10).

20. The prepolymer of any one of inventions 14 to 19, having a weight average molecular weight of at least about 2,000 Daltons, and comprising from about 1% to about 25% by mole (preferably from about 2% to about 15% by mole) of the repeating units of formula (VI).

21. The prepolymer of any one of inventions 14 to 20, wherein $R_{14}$ is methylene divalent radical, $R_{11}$ is hydrogen or $C_1$-$C_4$ alkyl, $R_{13}$ is hydrogen, and $R_{12}$ is a radical of in which q2 is zero, $R_{18}$ is vinyl (*—CH=$CH_2$) or 1-methylethenyl (*—C($CH_3$)=$CH_2$).

22. The prepolymer of any one of inventions 14 to 21, wherein $R_{15}$ is a monovalent radical of formula (VIII).

23. The prepolymer of any one of inventions 14 to 21, wherein $R_{15}$ is a monovalent radical of formula (IX).

24. The prepolymer of any one of inventions 7 to 9, wherein $R_{15}$ is a monovalent radical of formula (X).

25. The prepolymer of any one of inventions 14 to 21, wherein $R_{15}$ is a monovalent radical of formula (XI).
26. The prepolymer of any one of inventions 14 to 21, wherein $R_{15}$ is a monovalent radical of formula (XII).
27. A method for producing UV-absorbing contact lenses, comprising the steps of:
   (1) obtaining an aqueous lens formulation comprising
      (a) one or more water-soluble actinically-crosslinkable polyvinyl alcohol prepolymers of any one of inventions 14 to 26, and
      (b) at least free-radical initiator;
   (2) introducing the aqueous lens formulation into a mold for making a soft contact lens, wherein the mold has a first mold half with a first molding surface defining the anterior surface of a contact lens and a second mold half with a second molding surface defining the posterior surface of the contact lens, wherein said first and second mold halves are configured to receive each other such that a cavity is formed between said first and second molding surfaces; and
   (3) curing thermally or actinically the aqueous lens formulation in the mold to crosslink the prepolymers and other polymerizable components in the aqueous lens formulation to form the UV-absorbing contact lens,
   wherein the formed UV-absorbing contact lens comprises an anterior surface defined by the first molding surface and an opposite posterior surface defined by the second molding surface and is characterized by having an UVB transmittance of about 10% or less between 280 and 315 nanometers and a UVA transmittance of about 30% or less between 315 and 380 nanometers and and optionally a Violet transmittance of about 60% or less between 380 nm and 440 nm.
28. The method of invention 27, wherein the formed UV-absorbing contact lens has a Violet transmittance of about 60% or less (preferably about 50% or less, more preferably about 40% or less, even more preferably about 30% or less) between 380 nm and 440 nm.
29. The method of invention 27 or 28, wherein the free-radical initiator is a thermal initiator, wherein the step of curing is carried out thermally.
30. The method of invention 27 or 28, wherein the free-radical initiator is a photoinitiator, wherein the step of curing is carried out by irradiation with a light having a wavelength within the range from 380 nm to 500 nm.
31. The method of invention 30, wherein the mold is a reusable mold, wherein the step of curing is carried out under a spatial limitation of radiation.
32. A hydrogel contact lens comprising a crosslinked polymeric material which is a crosslinking and polymerizing product of at least one water-soluble actinically-crosslinkable polyvinyl alcohol prepolymer of any one of claims 14 to 26 in the presence or absence of a vinylic monomer and/or a vinylic crosslinking agent.
33. The hydrogel contact lens of invention 32, wherein the hydrogel contact lens has: an UVB transmittance of about 10% or less between 280 and 315 nanometers; a UVA transmittance of about 30% or less between 315 and 380 nanometers; optionally a Violet transmittance of about 60% or less between 380 nm and 440 nm; and a water content of from about 15% to about 80% when fully hydrated.
34. The hydrogel contact lens of invention 33, wherein the hydrogel contact lens has an UVB transmittance of about 5% or less between 280 and 315 nanometers.
35. The hydrogel contact lens of invention 33, wherein the hydrogel contact lens has an UVB transmittance of about 2.5% or less between 280 and 315 nanometers.
36. The hydrogel contact lens of invention 33, wherein the hydrogel contact lens has an UVB transmittance of about 1% or less between 280 and 315 nanometers.
37. The hydrogel contact lens according to any one of inventions 32 to 36, wherein the hydrogel contact lens has a UVA transmittance of about 20% or less between 315 and 380 nanometers.
38. The hydrogel contact lens according to any one of inventions 32 to 36, wherein the hydrogel contact lens has a UVA transmittance of about 10% or less between 315 and 380 nanometers.
39. The hydrogel contact lens according to any one of inventions 32 to 36, wherein the hydrogel contact lens has a UVA transmittance of about 5% or less between 315 and 380 nanometers.
40. The hydrogel contact lens according to any one of inventions 32 to 39, wherein the hydrogel contact lens has a Violet transmittance of about 60% or less between 380 nm and 440 nm.
41. The hydrogel contact lens according to any one of inventions 32 to 39, wherein the hydrogel contact lens has a Violet transmittance of about 50% or less between 380 nm and 440 nm.
42. The hydrogel contact lens according to any one of inventions 32 to 39, wherein the hydrogel contact lens has a Violet transmittance of about 40% or less between 380 nm and 440 nm.
43. The hydrogel contact lens according to any one of inventions 32 to 39, wherein the hydrogel contact lens has a Violet transmittance of about 30% or less between 380 nm and 440 nm.
44. The hydrogel contact lens according to any one of inventions 32 to 43, wherein the hydrogel contact lens has a water content of from about 30% to about 75% by weight (at room temperature, about 22° C. to 28° C.) when fully hydrated.

The previous disclosure will enable one having ordinary skill in the art to practice the invention. Various modifications, variations, and combinations can be made to the various embodiment described herein. In order to better enable the reader to understand specific embodiments and the advantages thereof, reference to the following examples is suggested. It is intended that the specification and examples be considered as exemplary.

Example 1

Transmittance.

Contact lenses are manually placed into a specially fabricated sample holder or the like which can maintain the shape of the lens as it would be when placing onto eye. This holder is then submerged into a 1 cm path-length quartz cell containing phosphate buffered saline (PBS, pH~7.0-7.4) as the reference. A UV/visible spectrophotometer, such as, Varian Cary 3E UV-Visible Spectrophotometer with a LabSphere DRA-CA-302 beam splitter or the like, can be used in this measurement. Percent transmission spectra are collected at a wavelength range of 250-800 nm with % T values collected at 0.5 nm intervals. This data is transposed onto an Excel spreadsheet and used to determine if the lenses conform to Class 1 UV absorbance. Transmittance is calculated using the following equations:

$$UVA \% \ T = \frac{\text{Average } \% \ T \text{ between } 380 - 316 \text{ nm}}{\text{Luminescence } \% \ T} \times 100$$

$$UVB \% \ T = \frac{\text{Average } \% \ T \text{ between } 280 - 315 \text{ nm}}{\text{Luminescence } \% \ T} \times 100$$

$$\text{Violet } \% \ T = \frac{\text{Average } \% \ T \text{ between } 440 - 380 \text{ nm}}{\text{Luminescence } \% \ T} \times 100$$

in which Luminescence % T is the average % transmission between 380 and 780.

Photo-Rheology:

The photo-rheology experiment measures the elastic (G') and viscous modulus (G") as a function of time during curing. The experiment is conducted by using an appropriate light source, optionally cutoff filters to select wavelengths of interest, and a rheometer. The light source is a Mercury bulb in a Hamamatsu light source. The intensity of light source is set by adjusting the shutter opening to get an appropriate intensity measured by a radiometer. The sample is placed between a quartz plate that allows UV light to pass through and the rheometer. The cure time is determined when the elastic modulus (G') reaches a plateau.

Example 2

Synthesis of (5-chloro-2-((3-chloro-2-hydroxypropyl)amino)phenyl)(phenyl) methanone In a 500 mL erlenmyer flask equipped with a magnetic stirrer and air inlet is added 20.0 g (86.3 mmol) of (2-amino-5-chlorophenyl)(phenyl)methanone (Alfa Aesar), 70 g (750 mmol) epichlorohydrin (Acros Organics), and 5.0 grams Montmorillonite K10, powder (Aldrich). The reaction mixture is heated at 70° C. for 48 hours. Acetone (300 mL) is added and the reaction mixture is filtered using Celite as a filtering aid, concentrated under reduced pressure, and then recrystallized from diethyl ether to yield a yellow solid (30% yield). $^1$H NMR (CDCl$_3$) delta: 8.61 (1H, NH), 7.26-7.61 (7H, Ar—H), 6.80 (1H, Ar—H), 4.13 (1H, C$\underline{\text{H}}$—OH), 3.70 (2H, C$\underline{\text{H}}_2$—Cl), 3.46 (2H, C$\underline{\text{H}}_2$—N), 2.55 (1H, OH).

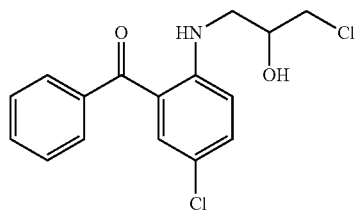 [SMILES: O=C(c1ccccc1)c1cc(Cl)ccc1NCC(O)CCl]

Example 3

Synthesis of 3-((2-benzoyl-4-chlorophenyl)amino)-N-(2,2-dimethoxyethyl)-2-hydroxy-N,N-dimethyl-propan-1-aminium chloride In a 250 mL 3-neck round bottom flask equipped with a magnetic stirrer and nitrogen inlet is added 6.10 g (18.8 mmol) (5-chloro-2-((3-chloro-2-hydroxypropyl)amino)phenyl)(phenyl)methanone, 22.6 g (170 mmol) 2,2-dimethoxy-N,N-dimethylethanamine (TCI), and 100 ml 1-propanol. The reaction mixture is heated to reflux for 15 h. The solvent is removed under reduced pressure to isolate the crude product.

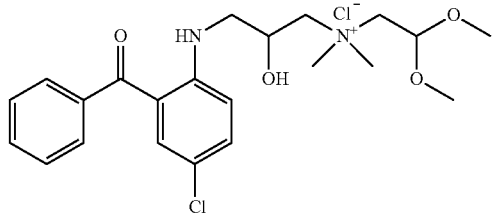 [SMILES: [Cl-] ; COC(C[N+](C)(C)CC(O)CNc1ccc(Cl)cc1C(=O)c1ccccc1)OC]

Example 4

Synthesis of 2-(2H-benzo[d][1,2,3]triazol-2-yl)-4-(2-hydroxyethyl)phenol

In a 4 L beaker equipped with a magnetic stirrer is added 234 g (725 mmol) 3-(2H-benzo[d][1,2,3]triazol-2-yl)-4-hydroxyphenethyl methacrylate, 87.0 g (217 mmol) sodium hydroxide and 1.5 mL DI water. The reaction mixture is stirred for 20 hours at room temperature and then diluted to 3.5 L with DI water. The solution is acidified with concentrated HCl (37%) and the resultant solid is filtered and washed with water and then dried. $^1$H NMR (CDCl$_3$) delta: 11.17 (1H, Ar—OH), 8.28 (1H, Ar—H), 7.93 (2H, Ar—H), 7.47 (2H, Ar—H), 7.23 (1H, Ar—H), 7.13 (1H, Ar—H), 3.92 (2H, C$\underline{\text{H}}_2$—OH), 2.92 (2H, Ar—C$\underline{\text{H}}_2$), 1.56 (1H, OH).

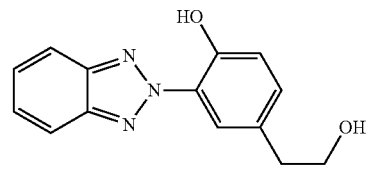 [SMILES: OCCc1ccc(O)c(-n2nc3ccccc3n2)c1]

Example 5

Synthesis of 2-(2H-benzo[d][1,2,3]triazol-2-yl)-4-(2-chloroethyl)phenol

In a 1 L Erlenmyer flask equipped with a magnetic stirrer is added 25.0 g (97.9 mmol) 2-(2H-benzo[d][1,2,3]triazol-2-yl)-4-(2-hydroxyethyl)phenol and 38.8 g (148 mmol) triphenylphosphine (Aldrich). 700 mL dichloromethane and 100 mL chloroform are added to the reaction mixture. Trichloroacetonitrile (31.5 g, 218 mmol) (Alfa Aesar) is added dropwise and the reaction mixture is stirred for 1.5 h at ambient temperature. The reaction mixture is washed with 1N HCl (4×1 L) and 1N NaCl (1×1 L). The organic layer is dried over sodium sulfate and concentrated under reduced pressure. The crude product is recrystallized from 2-propanol to give 22.4 g (84%) of a white solid. $^1$H NMR (CDCl$_3$) delta: 11.23 (1H, Ar—OH), 8.27 (1H, Ar—H), 7.93 (2H, Ar—H), 7.48 (2H, Ar—H), 7.23 (1H, Ar—H), 7.17 (1H, Ar—H), 3.77 (2H, C$\underline{\text{H}}_2$—Cl), 3.12 (2H, Ar—C$\underline{\text{H}}_2$).

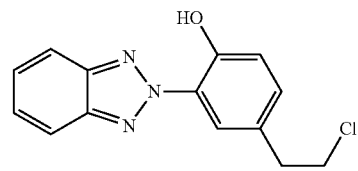 [SMILES: Oc1ccc(CCCl)cc1-n1nc2ccccc2n1]

Example 6

Synthesis of N-(3-(2H-benzo[d][1,2,3]triazol-2-yl)-4-hydroxyphenethyl)-2,2-dimethoxy-N,N-dimethylethanaminium chloride In a 500 mL flask equipped with a magnetic stirrer is added 5.2 g (19 mmol) of 2-(2H-benzo[d][1,2,3]triazol-2-yl)-4-(2-chloroethyl)phenol, 22.6 g (170 mmol) 2,2-dimethoxy-N,N-dimethylethanamine (TCI), and 150 ml DMF. The reaction mixture is heated to 110° C. for 15 h. The solvent is removed under reduced pressure to give the desired crude product.

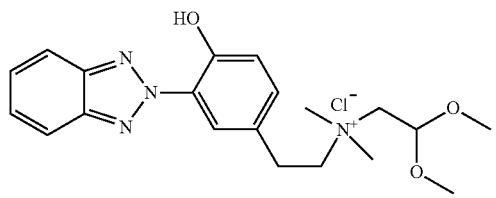 [SMILES: COC(C[N+](C)(C)CCc1ccc(O)c(-n2nc3ccccc3n2)c1)OC ; [Cl-]]

Example 7

Synthesis of 2-Acetyloxy-4-methoxy-4'-methylbenzophonone (AcO-Bzp-OMe-Me)

In a round bottom (rb) flask fitted with a stir bar and purged with dry nitrogen (dN2) is added 80 g anhydrous tetrahydrofuran (THF), 10 g (41.29 mmol, 1 eq) 2-hydroxy-4-methoxy-4'-methylbenzophonone (from Alfa Aesar, 41.29 mmol), and 0.25 g (5 mol % wrt Benzophenone) N,N-dimethyamino pyridine (4-DMAP, from Alfa Aesar). About 5 mL dry THF is used to rinse the DMAP vial and then this is added to the reaction flask. The flask is evacuated and purged with dried $N_2$ twice. The mixture is stirred at room temperature (RT) to dissolve over 15 mins. After 15 minutes of stirring, 26 g (6 eq.) of triethylamine (TEA) is added to the reaction solution, via a syringe. The solution is stirred at RT for 15 minutes. After 15 minutes, 13.17 g (3.1 eq) of acetic anhydride is added slowly to the reaction mixture in the flask over 5 minutes, followed by adding 15 ml of anhydrous THF. The reaction solution is stirred under $N_2$ at RT, overnight.

The reaction solution is concentrated under reduced pressure to remove about 80% of the volatiles. To the flask is added THF to dilute the concentrate to make a solution which is about 30% in benzophenone. This solution is stirred at RT for 5 mins. The product is precipitated by slow addition of 150 g of a mixture of 1:1 ice:water (5× by wt of reaction solution) with stirring. The flask is placed in ice water bath and stirred for 3 hours. After 3 hours, the pH of the solution phase is measured (observed pH: 3.86) and the mixture is filtered through a Whatman#4 (25 μm) filter paper under vacuum of 940 mbar.

The precipitate obtained is washed with about 1500 g of ice cold water until the filtrate washings are clear colorless and the conductivity of the filtrate is <10 uS/cm. The obtained precipitate obtained is suspended in 100 mL cold DI Water and swirled for 15 mins at RT. The sample is then frozen and lyophilized to give a white powder (11.45 g) which is confirmed by NMR to have the structure of AcO-Bzp-OMe-Me.

Synthesis of 2-Acetyloxy-4-Methoxy-4'-Bromomethylbenzophonone (AcO-Bzp-OMe-CH2-Br)

In a 500 mL 3-neck flask fitted with condenser, a $N_2$ purge set up, a thermocouple, an oil-bubbler air trap and a stir bar is added 8.85 g (0.031 mol) of AcO-Bzp-OMe-Me prepared above and stirred under $N_2$ for 30 minutes. The condenser is set to 9° C. and 220 mL anhydrous acetonitrile (ACN) is added to the reaction flask. The mixture is stirred at RT to effect a solution. Once the condenser reaches around 9° C., the reaction solution is gently purged with dry $N_2$ for 30 mins and the condenser is set to 4° C. After condenser reaches 4° C. or 30 mins of $N_2$ purge (whichever is later), the reaction solution is quickly raised to reflux with stirring and with a mildly positive $N_2$ flow. The reaction solution came to reflux at ~80-82° C.

6.11 g N-Bromosuccinimide (NBS) (1.1 eq) and 0.52 g Aza-bis-isobutyronitrile (AIBN) (0.1 eq) are weighed out and added to the reaction flask under positive $N_2$ flow. The reaction is continued, at reflux for 2 h with mildly positive nitrogen flow. After two hours the reaction is stopped by allowing to cool to RT under dry $N_2$. The reaction solution is cooled to RT and filtered through a cotton plug. The solution is then concentrated to about 50 wt % under reduced pressure. About 150 g-200 g of 1:1 ice-water mixture (about 3× the solution wt.) is prepared. This ice water mixture is slowly added to the stirred solution in the flask to effect precipitation. The mixture is then stirred in an ice bath for 3 hours. After three hours the obtained precipitate is filtered through a Whatman#4 (25 um) filter paper under 950 mbar. The precipitate is washed 5× with 200 mL cold DI Water. The final conductivity of the filtrate is less than 10 uS/cm and neutral pH. The obtained solid sample is mixed well with 100 mL cold DI Water and the mixture is then frozen and then lyophilized to yield a powdery off white solid which is confirmed by NMR to have the structure of 2-Acetyloxy-4-Methoxy-4'-Bromomethyl benzophonone (AcO-Bzp-OMe-CH2-Br).

Synthesis of N-(4-(2-acetoxy-4-methoxybenzoyl) benzyl)-2,2-dimethoxy-N,N-dimethylethan-1-aminium bromide In a $N_2$ purged 20 mL weighed glass vial with stir bar is added 1.5 g (0.004 mol, 1.0 eq) of AcO-Bzp-OMe-CH2-Br prepared above and 8 mL ethyl acetate to give a clear solution on stirring for 20 mins at RT. 1.88 g N,N-dimethylaminodimethylacetal (NNDMAADMA) (0.014 mol, 3.35 eq) is slowly added to the reaction solution with stirring. A precipitate soon is formed and gradually thickened with stirring over 30-60 minutes. The reaction mixture is stirred at RT overnight. To the reaction mixture is added 1 mL of hexane and the turbid mixture is stirred for an hour at RT and then stand for an hour. The clear supernatant is discarded. The residue is dissolved in 0.50 mL acetonitrile and mixture stirred for 30 mins to completely dissolve the residue, followed by addition of 0.5 mL to 1 mL of ethyl acetate. The product in the solution is purified by precipitation of the acetonitrile solution using excess 1:1 Ethyl acetate:hexane mixture. The process is repeated 4 times. To the solid obtained is added 5 mL DI Water and the mixture is allowed to dissolve the solid. The residual volatile organics are removed under reduced pressure to obtain a clear solution having neutral pH. The solution is frozen and lyophilized to give an off white solid which is confirmed by NMR to have the structure of N-(4-(2-acetoxy-4-methoxybenzoyl)benzyl)-2,2-dimethoxy-N,N-dimethylethan-1-aminium bromide. The product is slowly deliquescent and is flushed with dry $N_2$ and stored in a desiccator.

Synthesis of N-(4-(2-hydroxy-4-methoxybenzoyl)benzyl)-2,2-dimethoxy-N,N-dimethylethan-1-aminium bromide

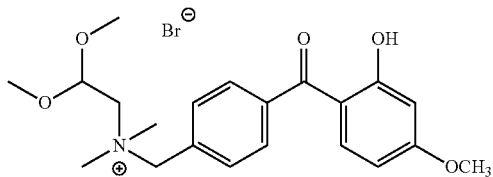 [SMILES: COc1ccc(C(=O)c2ccc(C[N+](C)(C)CC(OC)OC)cc2)c(O)c1 ; [Br-]]

A 5.0 mL solution of N-(4-(2-acetoxy-4-methoxybenzoyl)benzyl)-2,2-dimethoxy-N,N-dimethylethan-1-aminium bromide in DI Water at 1000 mg/L is prepared. This solution is diluted to 20 mg/L with pH7 buffer (12.5 mM phosphate in 1:1 DIWater:n-propanol). The UV-Vis spectrum of this solution is collected and is shown in FIG. 1 (curve 1). Solid potassium carbonate ($K_2CO_3$) is added to the 1000 mg/L solution to make a 1 w/v % solution in $K_2CO_3$. The solution is mixed to dissolve the $K_2CO_3$ and the solution is allowed to stand overnight at RT. This solution is diluted to 20 mg/L in UVBlocker with pH7 buffer (12.5 mM phosphate in DIWater:n-propanol). The UV-Vis spectrum of this solution is collected and is shown in FIG. 1 (Curve 2).

Example 8

A UV-absorbing polyvinylalcohol prepolymer is prepared according to the following scheme.

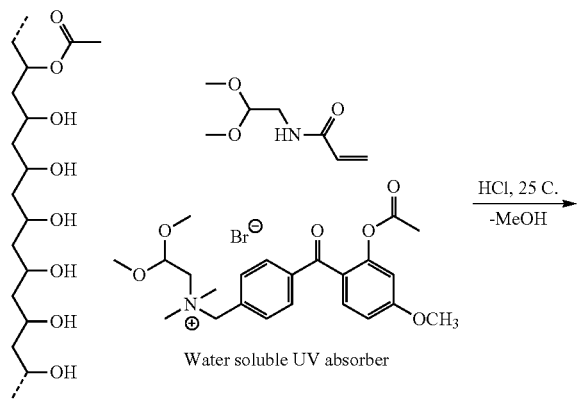

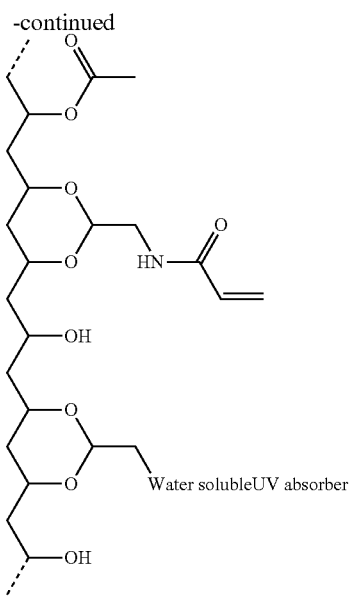

5 g of a 82% hydrolyzed polyvinylalcohol (PVA) is dissolved in 16 g of water by heating to 90° C. with rapid stirring for an hour and then cooled to room temperature. To this is added 0.2485 g of water soluble acetal based Benzophenone N-(4-(2-acetoxy-4-methoxybenzoyl)benzyl)-2,2-dimethoxy-N,N-dimethylethan-1-aminium bromide prepared in Example 7 as a 5 wt % aqueous solution and 0.3652 g of acrylamidoacetaldehyde dimethylacetal (NAAADA). Another 0.5 mL of water is used to rinse the vials and is added to the reaction mixture. The reaction mixture is made acidic down to pH~0 by addition of concentrated HCl solution. The reaction mixture is then stirred at RT for 11.5 h at 25° C. in a water bath. After the desired reaction time the reaction is neutralized with 7.5 wt % aq NaOH solution at 10-15° C. to pH 6.0-6.2. The reaction mixture is purified by dialysis with DI Water through a 1 KD regenerated cellulose membrane over two days and followed by UV-Vis and conductivity of permeate. The dialysis is stopped after the conductivity of the permeate reaches less than 10 uS/cm. The dialyzed UV-absorbing PVA prepolymer is concentrated to 30% solids under reduced pressure.

A formulation is made from this UV-absorbing PVA prepolymer (UV-mPVA) by adding 1 wt % Lithium salt of 2,4,6-trimethylbenzoyl-diphenylphosphine oxide (Li-TPO) photoinitiator (from TCI-America).

A control formulation is prepared from a PVA-prepolymer (i.e., a NAAADA-modified PVA according to the procedures above except without any water-soluble UV-absorber) and 1 wt % Li-TPO photoinitiator is added.

Lenses are then fabricated from this formulation using photocuring with 405 nm LED at 30 mW/cm² for about 26 seconds. The lenses are autoclaved (AC) and then reanalyzed by UV-Vis spectroscopy. Table 1 shows the % Transmission of prepared lenses.

TABLE 1

| | % T | |
| --- | --- | --- |
| | UVA | UVB |
| Control (no UV absorber) | 96.5 | 84.91 |
| UV-absorbing PVA prepolymer | 95.2 | 82.25 |

The results indicate that the attachment of the water-soluble UV-absorbing benzophenone of Example 7 to PVA may not be efficient. It is believed that the presence of the positively charged quaternary ammonium nitrogen vicinal to the acetal group on the UV blocker molecule may electronically hinder the reaction between acetal and 1,3-diol.

Example 9

Synthesis of N-(4-(2-acetoxy-4-methoxybenzoyl) benzyl)-4,4-diethoxy-N,N-dimethylbutan-1-aminium bromide In a N$_2$ purged 20 mL weighed glass vial with stir bar is added 1.5 g (0.004 mol, 1.0 eq) of AcO-Bzp-OMe-CH2-Br prepared in Example 7 and 8 mL ethyl acetate to give a clear solution on stirring for 20 mins at RT. 2.06 g 4,4-Diethoxy-N,N-dimethyl-1-butanamine (NNDMABADEA, from TCI-America) (0.01 mol, 2.5 eq) is slowly added to the reaction solution with stirring. A precipitate is soon formed and gradually thickens with stirring over 30-60 minutes. The reaction mixture is stirred at RT overnight. The stirring is stopped and the mixture is allowed to stand for an hour. The mixture is filtered through a coarse filter frit at around 850 mbar. The precipitate is washed five times with 10 mL ethyl acetate. The precipitate is transferred into a 100 mL rb flask with about 18 ml of DI Water. The residual organics are removed under reduced pressure to give a clear solution. The solution is filtered through a Whatman#1 (11 um) filter paper to give a clear solution with neutral pH, that is frozen and lyophilized to give a off white solid which is confirmed to be N-(4-(2-acetoxy-4-methoxybenzoyl)benzyl)-4,4-diethoxy-N,N-dimethylbutan-1-aminium bromide and is stored under dry N$_2$ in desiccator.

Synthesis of 4,4-diethoxy-N-(4-(2-hydroxy-4-methoxybenzoyl)benzyl)-N,N-dimethylbutan-1-aminium bromide

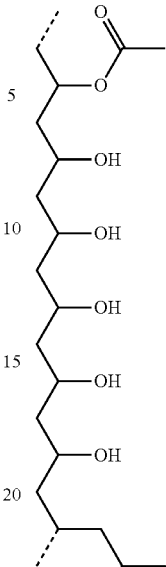

Figure 2:
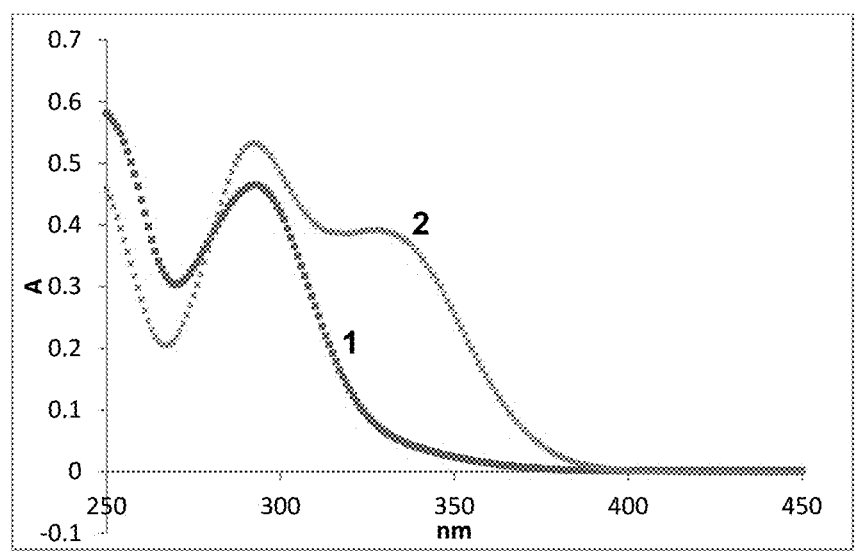
FIG. 2 shows the UV spectrum of another preferred water-soluble UV absorber of the invention in phosphate buffer (pH~7, 12.5 mM phosphate in 1:1 Water:n-propanol).

A 5.0 mL solution of N-(4-(2-acetoxy-4-methoxybenzoyl) benzyl)-4,4-diethoxy-N,N-dimethylbutan-1-aminium bromide in DI Water at 1000 mg/L is prepared. This solution is diluted to 20 mg/L with pH7 buffer (12.5 mM phosphate in 1:1 DIWater:n-propanol). The UV-Vis spectrum of this solution is collected and is shown in FIG. 2 (curve 1). Solid potassium carbonate (K$_2$CO$_3$) is added to the 1000 mg/L solution to make a 1 w/v % solution in K$_2$CO$_3$. The solution is mixed to dissolve the K$_2$CO$_3$ and the solution is allowed to stand overnight at RT. This solution is diluted to 20 mg/L in UVBlocker with pH7 buffer (12.5 mM phosphate in DIWater:n-propanol). The UV-Vis spectrum of this solution is collected and is shown in FIG. 2 (Curve 2).

Example 10

A UV-absorbing polyvinylalcohol prepolymer is prepared from G-Polymer (Nippon Gohsei) according to the following scheme.

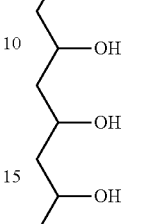

5 g of glycerol modified PVA (G-Polymer OKS-8049 from Nippon Gohsei) is dissolved in 17 g of water by heating to 70° C. with rapid stirring for an hour and then cooled to room temperature. To this is added 0.2485 g of water soluble acetal based Benzophenone UVBlocker N-(4-(2-acetoxy-4-methoxybenzoyl)benzyl)-4,4-diethoxy-N,N-dimethylbutan-1-aminium bromide prepared in Example 9 as a 5 wt % aqueous solution and 0.3652 g of acrylamido-acetaldehyde dimethylacetal (NAAADA). Another 0.5 mL of water is used to rinse the vials and is added to the reaction mixture. The reaction mixture is made acidic down to pH~0 by addition of concentrated HCl solution. The reaction mixture is then stirred at RT for 11.5 h at 25° C. in a water bath. After the desired reaction time the reaction is neutralized with 7.5 wt % aq NaOH solution at 10-15° C. to pH 6.0-6.2. The reaction mixture is purified by dialysis with DI Water through a 1 KD regenerated cellulose membrane over two days and followed by UV-Vis and conductivity of permeate. The dialysis is stopped after the conductivity of the permeate reaches less than 10 uS/cm. The dialyzed UV-absorbing PVA prepolymer (i.e., UV-absorbing G-prepolymer) is concentrated to 30% solids under reduced pressure.

A formulation is made from this UV-absorbing G-prepolymer (UV-mPVA) by adding 1 wt % Lithium salt of 2,4,6-trimethylbenzoyl-diphenylphosphine oxide (Li-TPO) photoinitiator (from TCI-America).

A control formulation is prepared from a G-prepolymer (i.e., a NAAADA-modified Glycerol-PVA according to the procedures above except without any water-soluble UV-absorber) and 1 wt % Li-TPO photoinitiator is added.

Lenses are then fabricated from this formulation using photocuring with 405 nm LED at 30 mW/cm$^2$ for about 26 seconds. The lenses are packaged and autoclaved (AC) in packages containing phosphate buffered saline and then reanalyzed by UV-Vis spectroscopy. Table 2 shows the % Transmission of resultant lenses.

TABLE 2

| | % T | |
|---|---|---|
| | UVA | UVB |
| Control (no UV absorber) | 96.55 | 86.0 |
| UV-Absorbing G-prepolymer | 20.85 | 2.05 |

The results indicate that, when a three carbon spacer group is inserted between the acetal group and the positively charged quaternary ammonium nitrogen, the reactivity of the acetal moiety with 1,3-diol can be enhanced (compared to Example 8).

Example 11

Synthesis of
2-(2-acetyloxy-5-methylphenyl)benzotriazole
(AcO-Me-Bzt)

In a weighed 2 L rb flask fitted with a magnetic stir bar and purged with N$_2$ is added 340 g anhydrous THF. The flask is purged with N$_2$ for a minute while stirring and then capped. 40 g (177.4 mmol, 1.0 eq) of 2-(2-Hydroxy-5-methylphenyl)benzotriazole (Me-Bzt-OH, from TCI-America) is weighed and added to the flask. The reaction flask is quickly purged with N$_2$ and then capped and stirred for 15 minutes to allow the solid to dissolve. To this solution is added 1.09 g (8.87 mmol) of 4-dimethylaminopyridine (4-DMAP) (5 mol % wrt benotriazole). The flask is quickly purged with N$_2$, capped and the reaction mixture is allowed to stir for 15 minutes to allow the solid to dissolve. 108.96 g (6 eq) of Triethyl amine (Et$_3$N) is weighed out and slowly added to the reaction flask with stirring. The flask is quickly purged with N$_2$, capped and the reaction mixture is allowed to stir for 15 minutes. 54.58 g (3 eq) of Ac$_2$O is weighed out and then slowly added to the reaction solution. 20 g of THF is added to the reaction. The flask is purged with N$_2$, capped tightly and the reaction solution is allowed stir under N$_2$ overnight.

The reaction solution is concentrated under reduced pressure, to remove ~65-70% of the volatiles or until precipitation is observed, whichever is earlier. If precipitation is seen, just enough THF is added to just dissolve the precipitate. The solution is stirred at RT for 30 mins. The product is precipitated by addition of a mixture of 250 g ice and 250 g DI Water with stirring. The obtained mixture had a pH of 4.75. The flask is place in an ice bath and stirred for 3 hours. The mixture is filtered through a Whatman#4 (25 um) filter paper under vacuum of 950 mbar. The precipitate is washed five times with 1 Kg of ice-water until the washings are clear colorless and the conductivity of the filtrate is <10 uS/cm. The precipitate is collected and mixed with 500 mL cold DI water. The mixture is frozen and then lyophilized to give a white powder (47.22 g) whose structure is confirmed by NMR to be AcO-Me-Bzt.

Synthesis of
2-(2-acetyloxy-5-bromomethylphenyl)benzotriazole
(AcO-Bzt-CH$_2$Br)

In a weighed 1 L 3 neck flask fitted with condenser, a N$_2$ purge set up, a thermocouple and an oil-bubbler air trap, is added 20 g (0.074 mmol, 1.0 eq) of AcO-Me-Bzt (II) prepared above. This solid is stirred under N$_2$ for at least 45 mins. To this is added 480 mL anhydrous acetonitrile. The mixture is stirred at RT. The condenser is set to 9° C. The reaction solution is gently bubbled with dry N$_2$ for 30 mins and the condenser reset to 4 C. After condenser reaches 4° C. or 30 mins of N$_2$ purge (whichever is later), the reaction mixture is quickly raised to reflux, stirred at 400 rpm with a slightly positive N$_2$ flow. The reaction solution comes to reflux at ~81-82° C. and a clear solution is observed. Then NBS (1.1 eq/14.71 g); and AlBN (0.1 eq./1.25 g) are added to the reaction flask under positive N$_2$ flow. The reaction is continued at 500 prm, reflux and positive N$_2$ flow. After 2 h 15 m the reaction is stopped by allowing to cool to RT under N$_2$. The solution is filtered through a cotton plug. The solution is then concentrated under reduced pressure to yield a solid material. To the sample is added 75 mL of 6.67% acetonitrile (ACN) in THF to dissolve the solid. About 250 g of 1:1 ice-water by weight is prepared (~2.5× the total solution volume). The product is precipitated by slow addition of the ice-water mixture with stirring. The flask is then placed in an ice bath and stirred for 3 hours. The precipitate is filtered through a Whatman#4 (25 um) filter paper under 950 mbar. The precipitate is washed 5× with 500 mL cold DI Water. (~10× volume of ice-water used for pptn) until the conductivity of the filtrate is <10 uS/cm and neutral pH. The solid precipitate is mixed with 100 mL cold DI Water. The mixture is then frozen and then lyophilized. An off-white solid powder (26.08 g) is obtained and confirmed by NMR to be AcO-Bzt-CH$_2$Br.

Synthesis of N-(4-acetoxy-3-(2H-benzo[d][1,2,3]
triazol-2-yl)benzyl)-2,2-dimethoxy-N,N-dimethyl-
ethan-1-aminium bromide (AcO-Bzt-CH$_2$-q-acetal)

In a weighed N2 purged 1 L flask with stir bar is added 22 g (0.058 mol, 1.0 eq) of AcO-Bzt-CH$_2$Br prepared above. To this is added 350 mL ethylacetate (EtAc) to give a clear solution on stirring. The solution is stirred at RT for an hour. During this time, 24 g (0.176 mol, 3.0 eq.) of N,N-dimethylaminodimethylacetal (NNDMAADMA, from TCI-America) is measured out in a 50 mL dropping funnel. The NNDMAADMA is slowly added to the reaction solution dropwise over 3 minutes at RT with stirring. The flask is stirred at RT. After stirring for about two additional minutes the solution slowly turns hazy. The precipitate gradually is thickened with stirring over 30-60 minutes. The reaction is stirred at RT overnight. This reaction mixture is filtered through a Filter Frit (16-40 um) lined with Whatman#4 (20-25 μm) filter paper, under 940-950 mbar pressure over 30-40 minutes. The residue is washed 6 times with 50 mL Ethylacetate. The residue is transferred to a weighed 1 L rb flask and then residual ethyl acetate and organic volatiles are removed under reduced pressure to give a solid material. This solid is dissolved in 200 mL DI Water and the obtained solution is gravity filtered through a Whatman#1 (11.0 um) filter paper over a couple of hours to give a clear solution with neutral pH. This is frozen and lyophilized to give an off-white solid that is slowly deliquescent. It is confirmed by NMR to be AcO-Bzt-CH$_2$-q-acetal. The obtained product is stored in a desiccator.

Synthesis of N-(3-(2H-benzo[d][1,2,3]triazol-2-yl)-4-hydroxybenzyl)-2,2-dimethoxy-N,N-dimethyl-ethan-1-aminium bromide

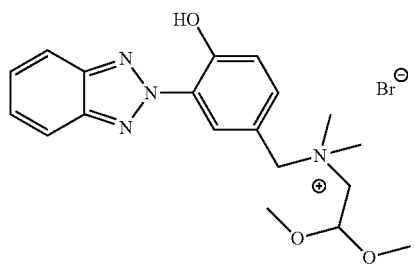

Figure 3:
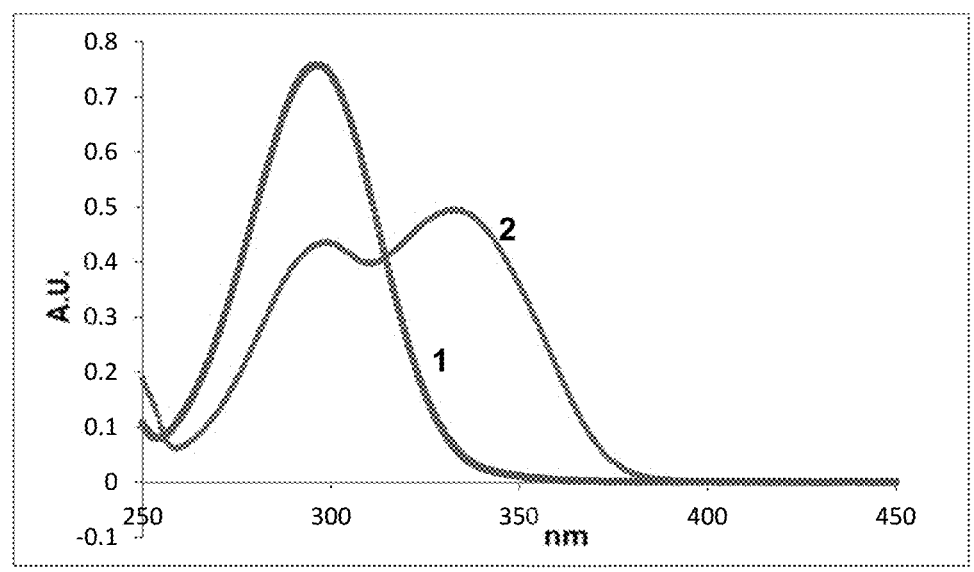
FIG. 3 shows the UV spectrum of a further preferred water-soluble UV absorber of the invention in phosphate buffer (pH~7, 12.5 mM phosphate in 1:1 Water:n-propanol).

A 5.0 mL solution of AcO-Bzt-CH$_2$-q-acetal (prepared above) in DI Water at 1000 mg/L is prepared. This solution is diluted to 20 mg/L with pH7 buffer (12.5 mM phosphate in 1:1 DIWater:n-propanol). The UV-Vis spectrum of this solution is collected (FIG. 3, Curve 1).
Solid potassium carbonate (K$_2$CO$_3$) is added to the 1000 mg/L solution of AcO-Bzt-CH$_2$-q-acetal to make a 1 w/v % solution in K$_2$CO$_3$. The solution is mixed to dissolve the K$_2$CO$_3$ and the solution is allowed to stand overnight at RT. This solution is diluted to 20 mg/L of UVBlocker with pH7 buffer (12.5 mM phosphate in DIWater:n-propanol). The UV-Vis spectrum of this solution is collected and is shown in FIG. 3 (Curve 2).

Example 12

A UV-absorbing polyvinylalcohol prepolymer is prepared according to the following scheme.

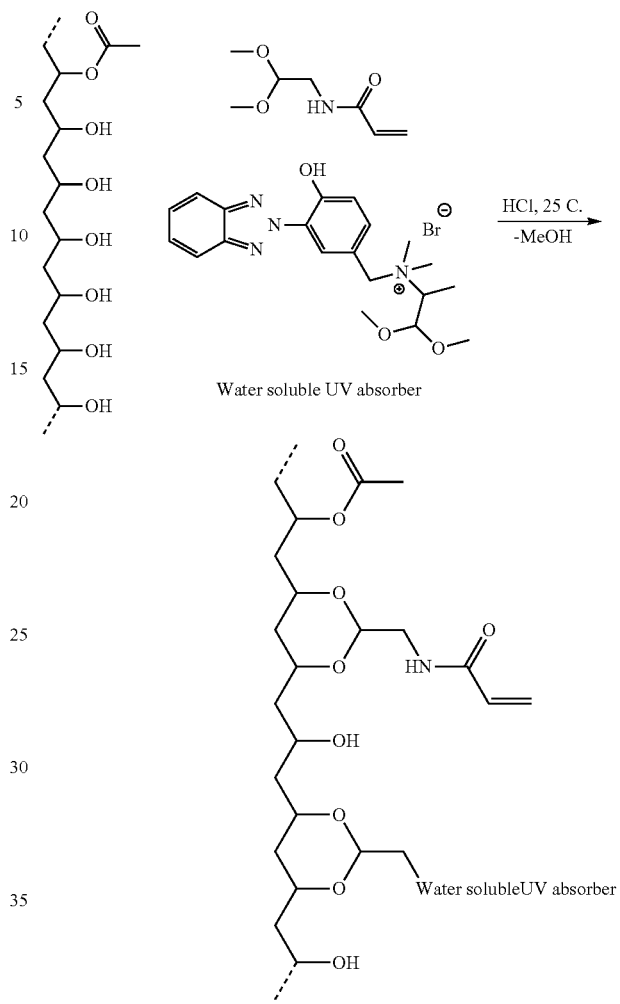

5 g of a 82% hydrolyzed polyvinylalcohol (PVA) is dissolved in 16 g of water by heating to 90° C. with rapid stirring for an hour and then cooled to room temperature. To this is added 0.2485 g of water soluble acetal based Benzophenone UVBlocker (2-(2-hydroxy-5-(2,2-dimethoxy-ethyl-N,N-dimethylaminomethylphenyl) benzotriazole) prepared in Example 11 as a 5 wt % aqueous solution and 0.3652 g of acrylamidoacetaldehyde dimethylacetal (NAAADA). Another 0.5 mL of water is used to rinse the vials and is added to the reaction mixture. The reaction mixture is made acidic down to pH~0 by addition of concentrated HCl solution. The reaction mixture is then stirred at RT for 11.5 h at 25 C in a water bath. After the desired reaction time the reaction is neutralized with 7.5 wt % aq NaOH solution at 10-15° C. to pH 6.0-6.2. The reaction mixture is purified by dialysis with DI Water through a 1 KD regenerated cellulose membrane over two days and followed by UV-Vis and conductivity of permeate. The dialysis is stopped after the conductivity of the permeate reaches less than 10 uS/cm. The dialyzed UV-absorbing PVA prepolymer is concentrated to 30% solids under reduced pressure.
A formulation is made from this UV-absorbing PVA prepolymer (UV-mPVA) by adding 1 wt % Lithium salt of 2,4,6-trimethylbenzoyl-diphenylphosphine oxide (Li-TPO) photoinitiator (from TCI-America).

Lenses are then fabricated from this formulation using photocuring with 405 nm LED at 30 mW/cm² for about 26 seconds. The lenses are autoclaved (AC) and then reanalyzed by UV-Vis spectroscopy. Table 3 shows the % Transmission of prepared lenses.

TABLE 3

| | % T | |
|---|---|---|
| | UVA | UVB |
| UV-absorbing PVA prepolymer | 65.7 | 55.85 |

The results indicate that the attachment of the water-soluble UV-absorbing benzotriazole of Example 11 to PVA may not be efficient. It is believed that the presence of the positively charged quaternary ammonium nitrogen vicinal to the acetal group on the UV blocker molecule may electronically hinder the reaction between acetal and 1,3-diol.

What is claimed is:

1. An acetal-containing, UV-absorbing compound of any one of formula (I) to (V)

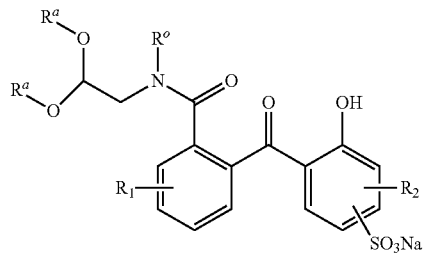
(I)

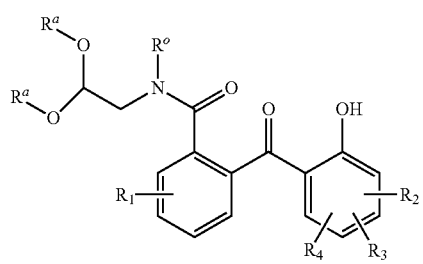
(II)

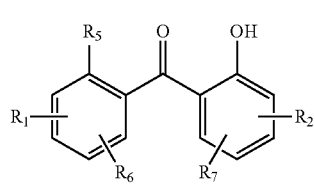
(III)

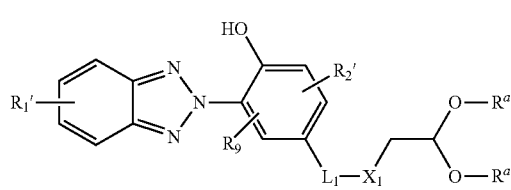
(IV)

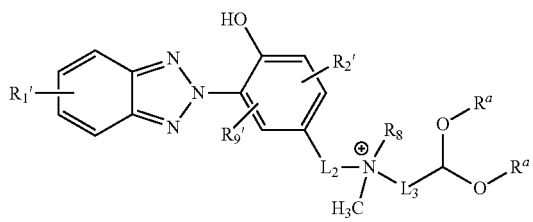
(V)

in which:
$R^a$ is $CH_3$ or $C_2H_5$;
$R^o$ is H or $CH_3$;
$R_1$, $R_2$ and $R_2'$ independent of one other are H, $CH_3$, $CCl_3$, $CF_3$, Cl, Br, NR'R" in which R' and R" independent of each other are H or $C_1$-$C_4$ alkyl, OH, or $OCH_3$;
$R_1'$ independent of each other are H, $CH_3$, $CCl_3$, $CF_3$, Cl, Br, NR'R" in which R' and R" independent of each other are H or $C_1$-$C_4$ alkyl, OH, $OCH_3$, $SO_3H$, or $SO_3^-Na^+$;
$R_3$ and $R_4$ independent of each other are H or a first hydrophilic group which is

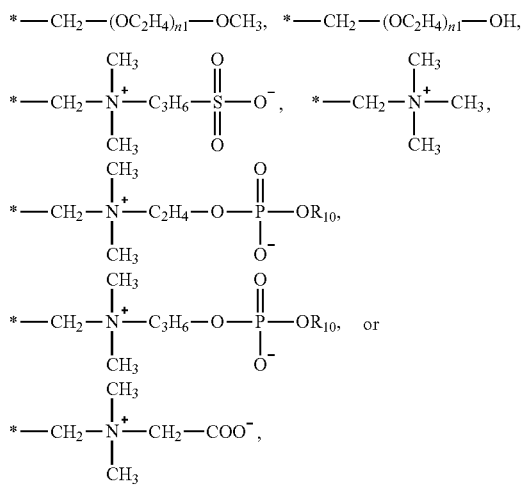

provided that at least one of $R_3$ and $R_4$ is the first hydrophilic group;
r1 is an integer of 1 to 8;
n1 is an integer of 2 to 20;
$R_5$ is H, *—COOH, *CONH—$C_2H_4$($OC_2H_4$)$_{n1}$—$OCH_3$, or —CONH—$C_2H_4$—($OC_2H_4$)$_{n1}$—OH; one of $R_6$ and $R_7$ is H or a second hydrophilic group which is

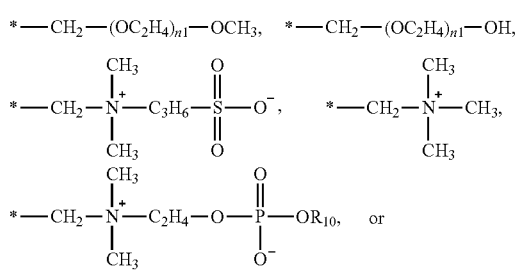

-continued

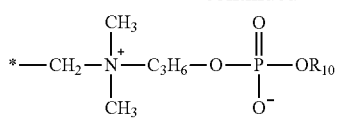

while the other of $R_6$ and $R_7$ is

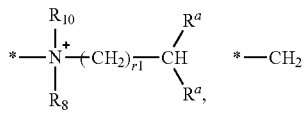

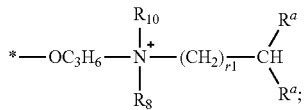

$R_8$ is $CH_3$, $C_2H_5$,

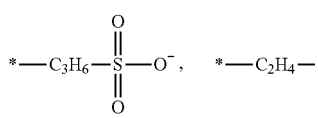

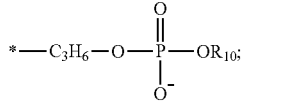

$R_9$ is $SO_3Na$,

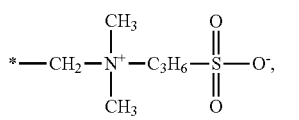

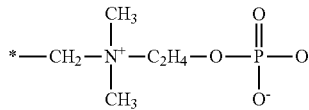

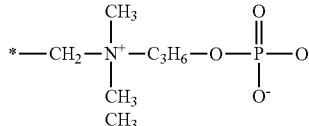

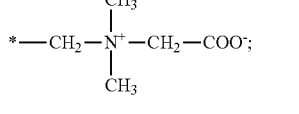

$R_9'$ is H, $SO_3Na$,

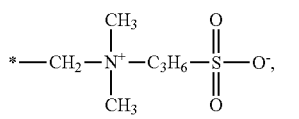

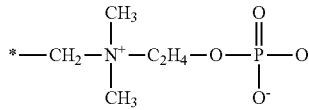

-continued

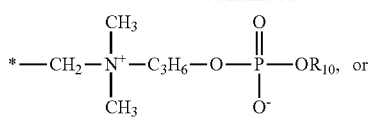

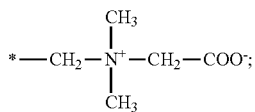

$R_{10}$ is methyl or ethyl;

L1 is a linkage of

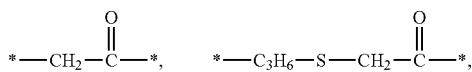

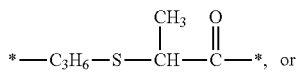

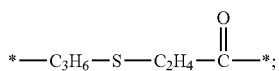

L2 is a linkage of

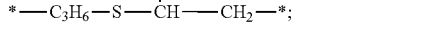

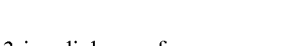

L3 is a linkage of

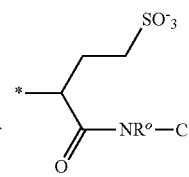

and

X1 is O or $NR^o$.

2. The acetal-containing, UV-absorbing compound of claim 1, being defined by formula (I).

3. The acetal-containing, UV-absorbing compound of claim 1, being defined by formula (II).

4. The acetal-containing, UV-absorbing compound of claim 1, being defined by formula (III).

5. The acetal-containing, UV-absorbing compound of claim 1, being defined by formula (IV).

6. The acetal-containing, UV-absorbing compound of claim 1, being defined by formula (V).

7. The acetal-containing, UV-absorbing compound of claim 2, wherein the acetal-containing, UV-absorbing compound is further defined by

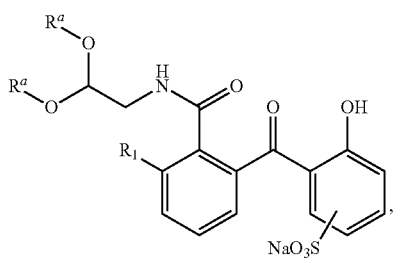
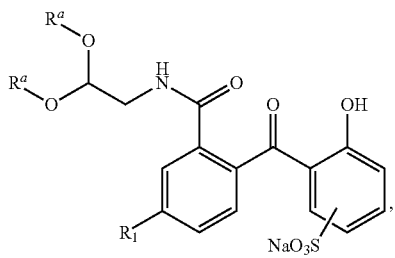
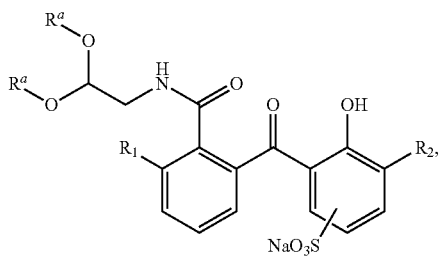
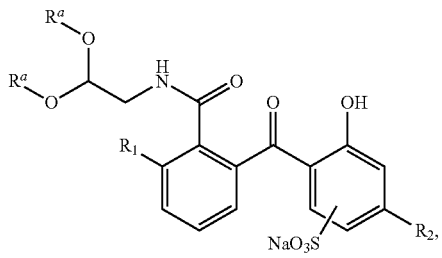
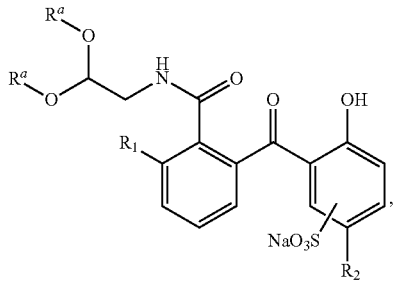
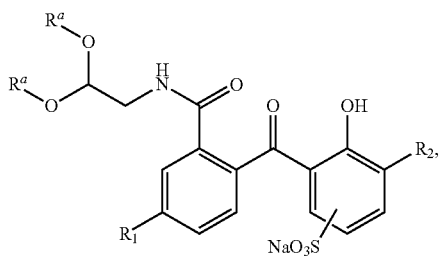
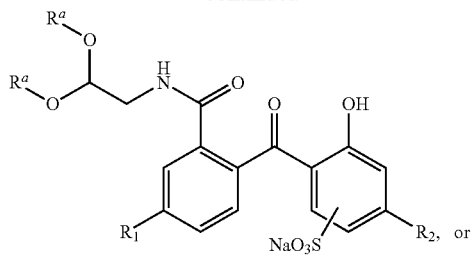
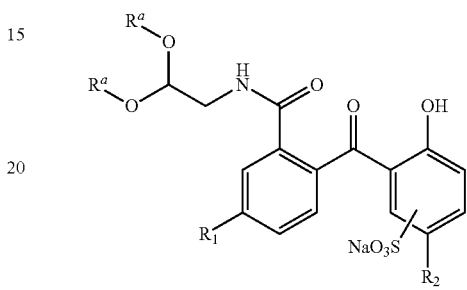
in which $R^a$ is methyl or ethyl, $R_1$ and R2 independent of each other are H, $CH_3$, $CCl_3$, $CF_3$, Cl, Br, NR'R", OH, or $OCH_3$, in which R' and R" independent of each other are H, methyl or ethyl.
8. The acetal-containing, UV-absorbing compound of claim 3, wherein the acetal-containing, UV-absorbing compound is further defined by
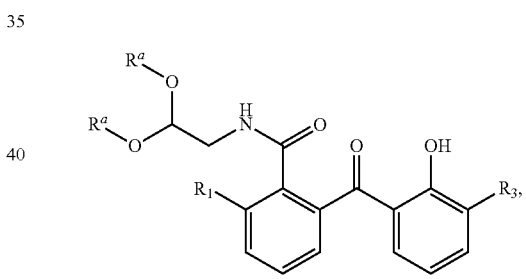
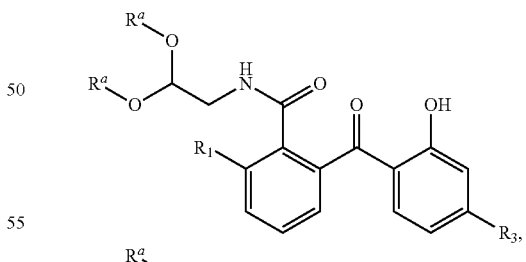
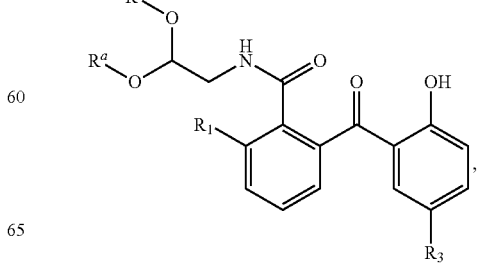

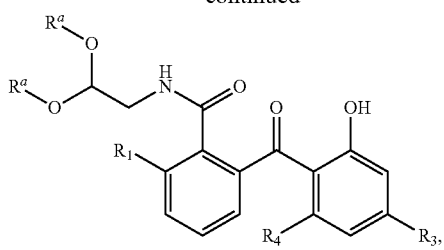
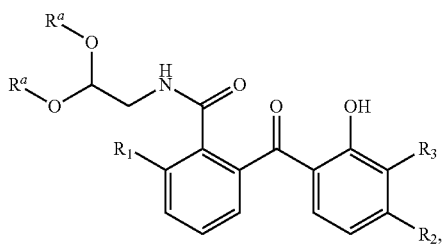
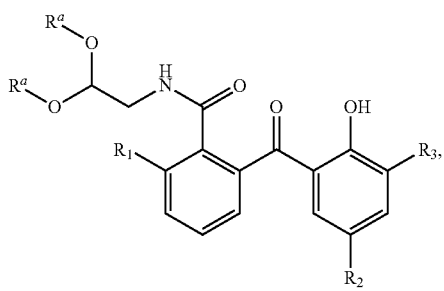
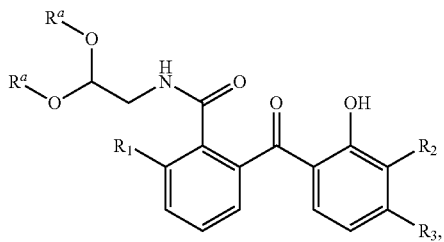
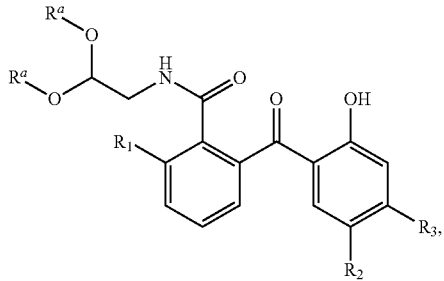
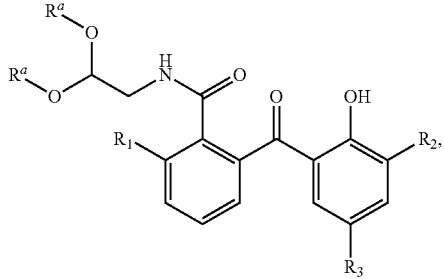
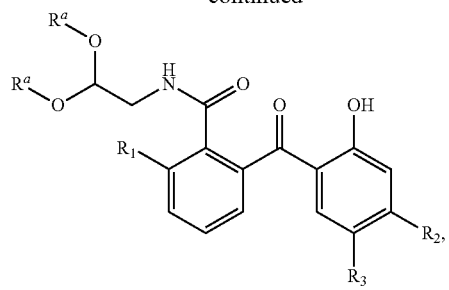
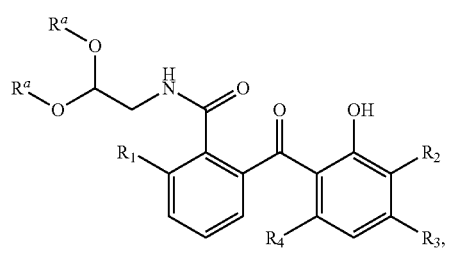
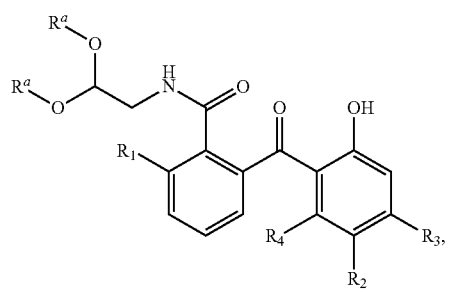
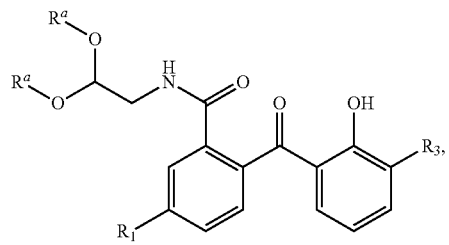
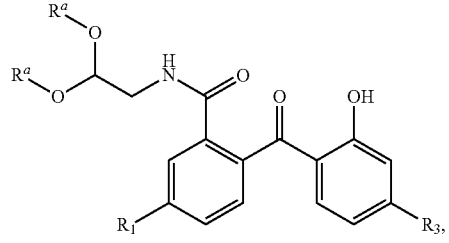
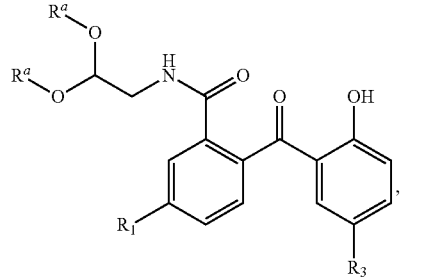

-continued

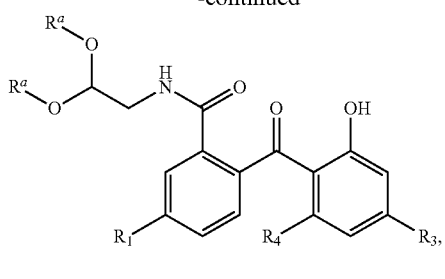

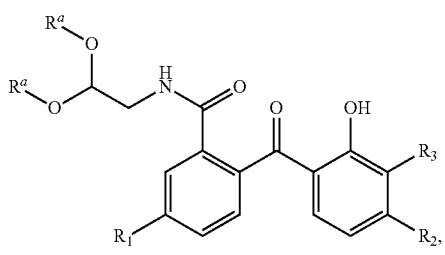

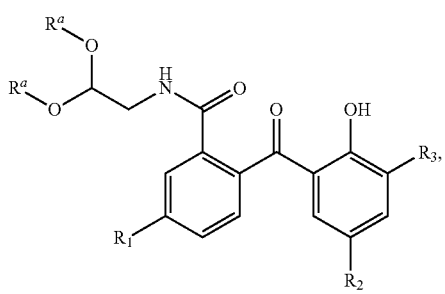

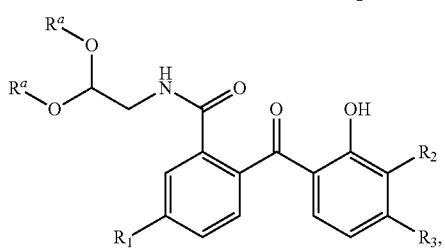

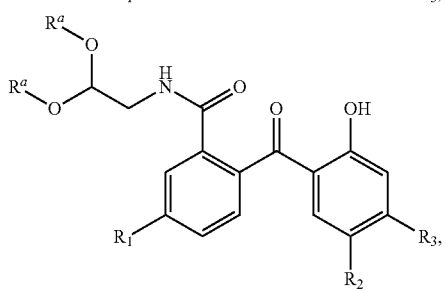

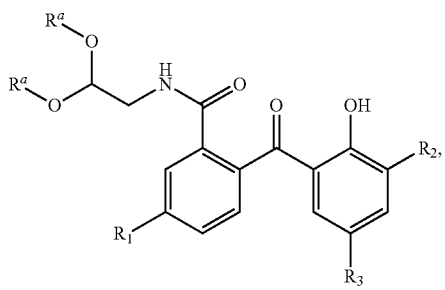

-continued

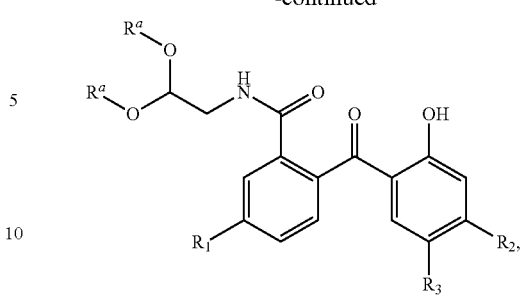

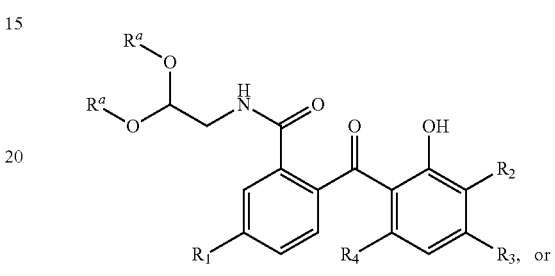

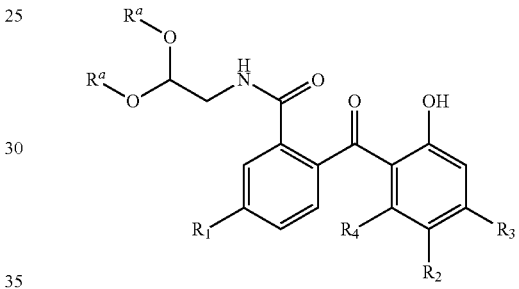, or

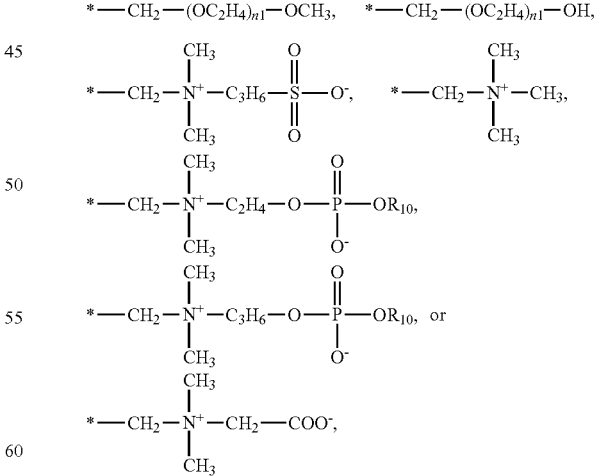

in which: $R^a$ is methyl or ethyl; $R_1$ and $R_2$ independent of each other are $CH_3$, $CCl_3$, $CF_3$, Cl, Br, NR'R", OH, or $OCH_3$; R' and R" independent of each other are H, methyl or ethyl; $R_3$ and $R_4$ independent of each other are $* - CH_2 - (OC_2H_4)_{n1} - OCH_3$,  $* - CH_2 - (OC_2H_4)_{n1} - OH$, $* - CH_2 - \underset{\underset{CH_3}{|}}{\overset{\overset{CH_3}{|}}{N^+}} - C_3H_6 - \underset{\underset{O}{||}}{\overset{\overset{O}{||}}{S}} - O^-$,  $* - CH_2 - \underset{\underset{CH_3}{|}}{\overset{\overset{CH_3}{|}}{N^+}} - CH_3$, $* - CH_2 - \underset{\underset{CH_3}{|}}{\overset{\overset{CH_3}{|}}{N^+}} - C_2H_4 - O - \underset{\underset{O^-}{|}}{\overset{\overset{O}{||}}{P}} - OR_{10}$, $* - CH_2 - \underset{\underset{CH_3}{|}}{\overset{\overset{CH_3}{|}}{N^+}} - C_3H_6 - O - \underset{\underset{O^-}{|}}{\overset{\overset{O}{||}}{P}} - OR_{10}$, or $* - CH_2 - \underset{\underset{CH_3}{|}}{\overset{\overset{CH_3}{|}}{N^+}} - CH_2 - COO^-$, $R_{10}$ is methyl or ethyl.

9. The acetal-containing, UV-absorbing compound of claim 4, wherein the acetal-containing, UV-absorbing compound is further defined by

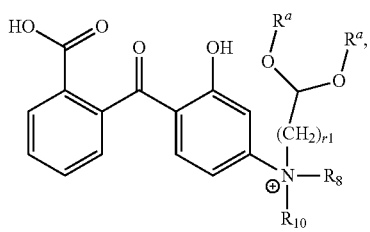
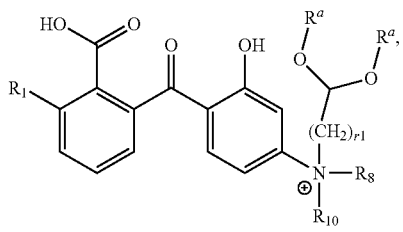
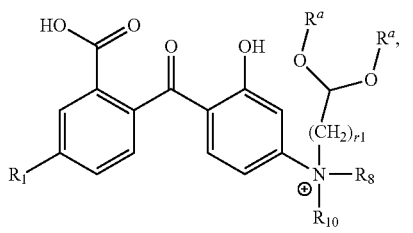
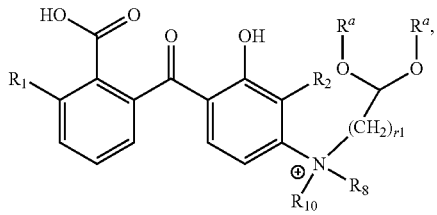
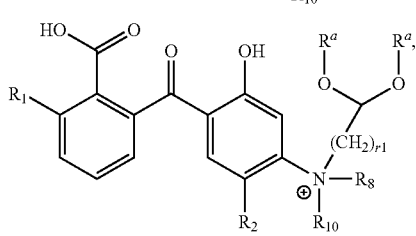
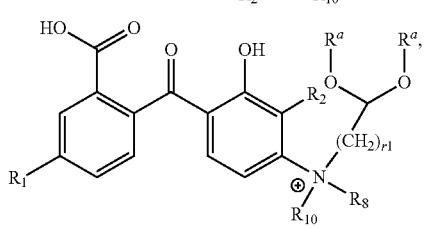
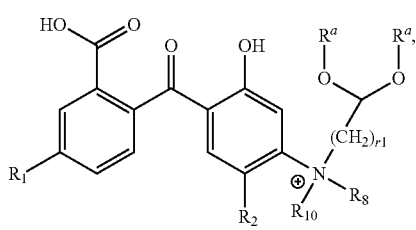
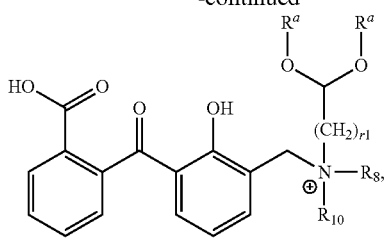
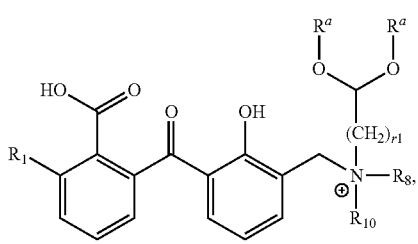
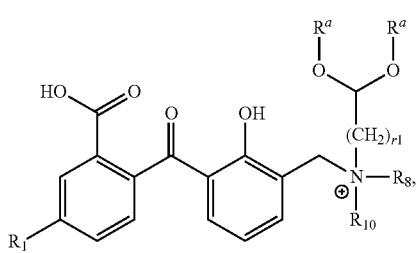
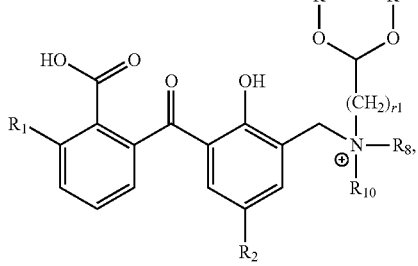
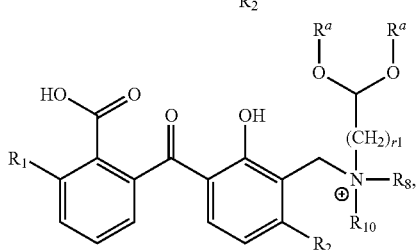
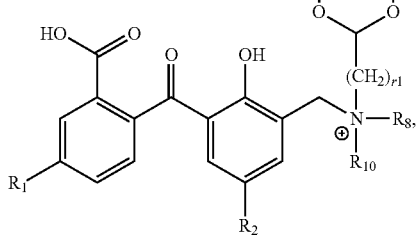

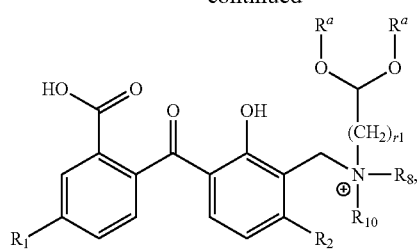
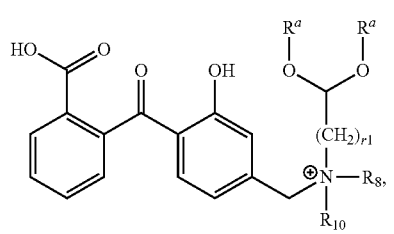
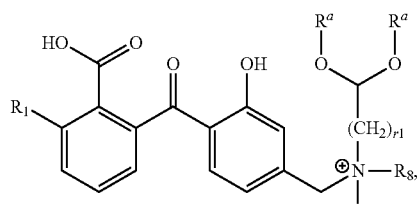
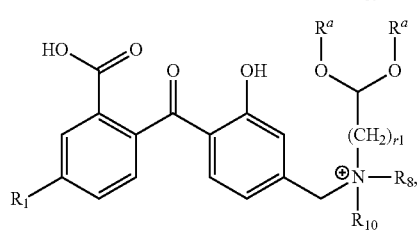
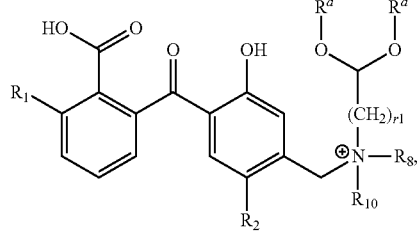
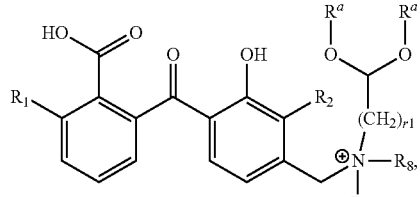
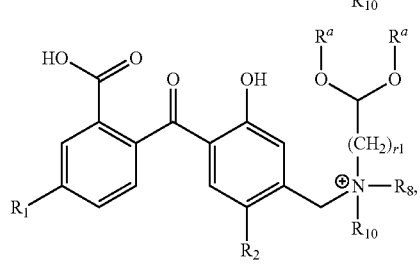
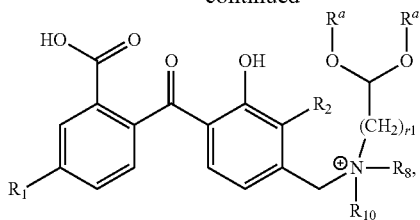
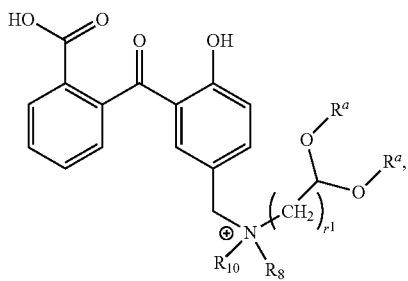
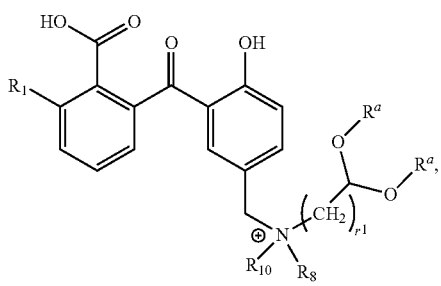
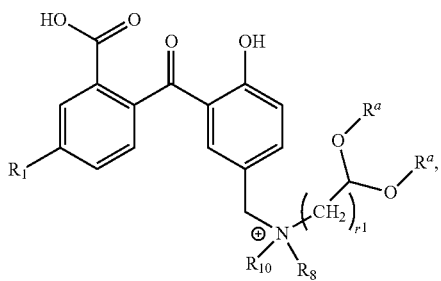
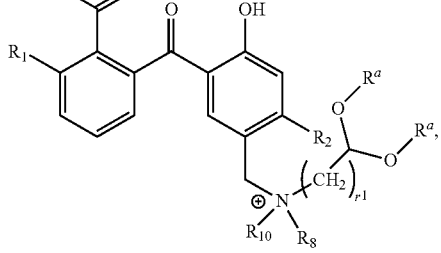
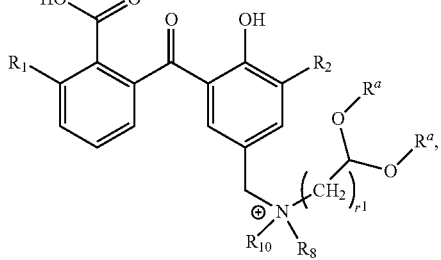

103
-continued
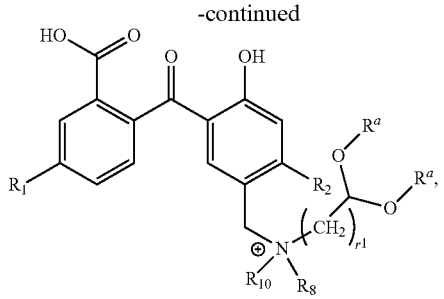
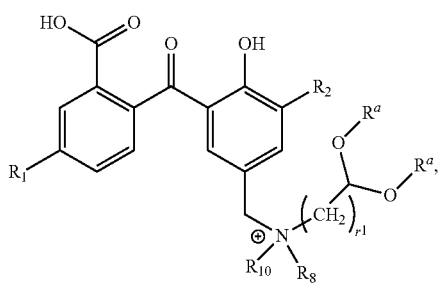
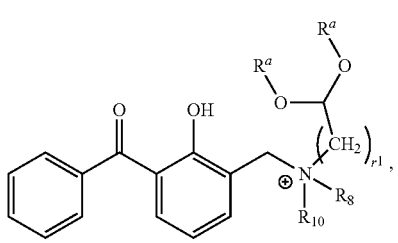
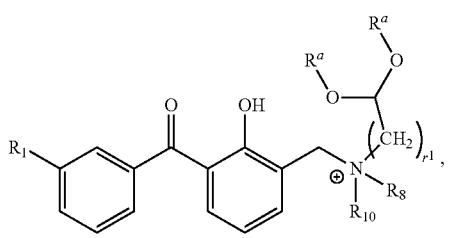
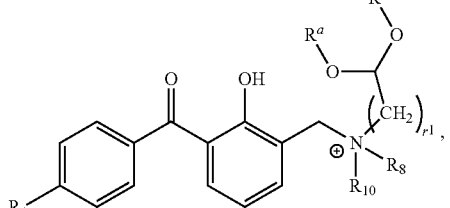
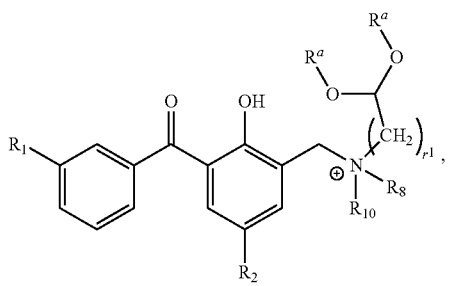
104
-continued
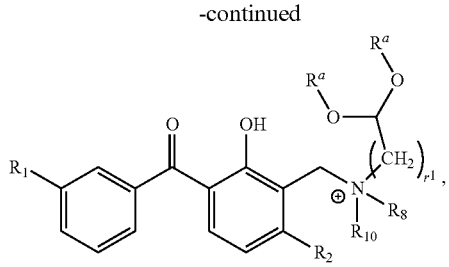
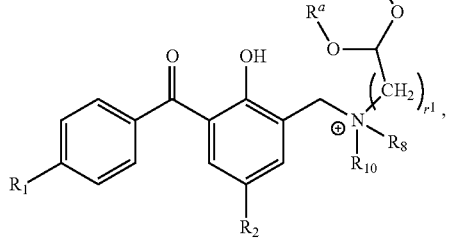
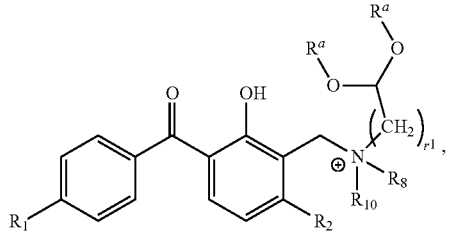
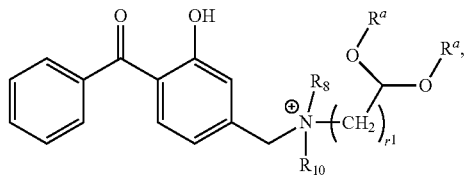
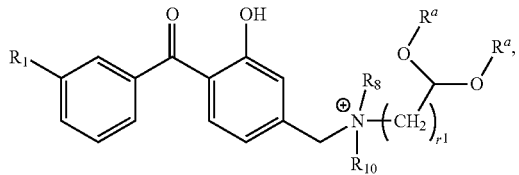
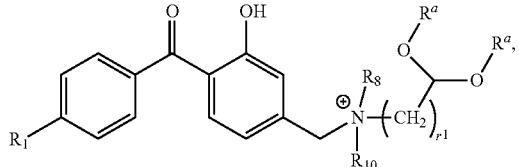
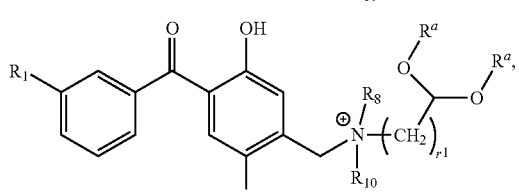
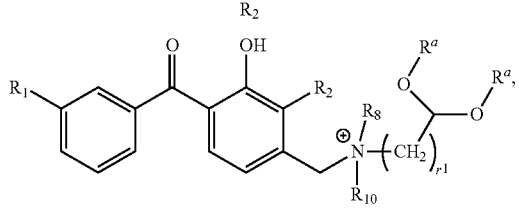

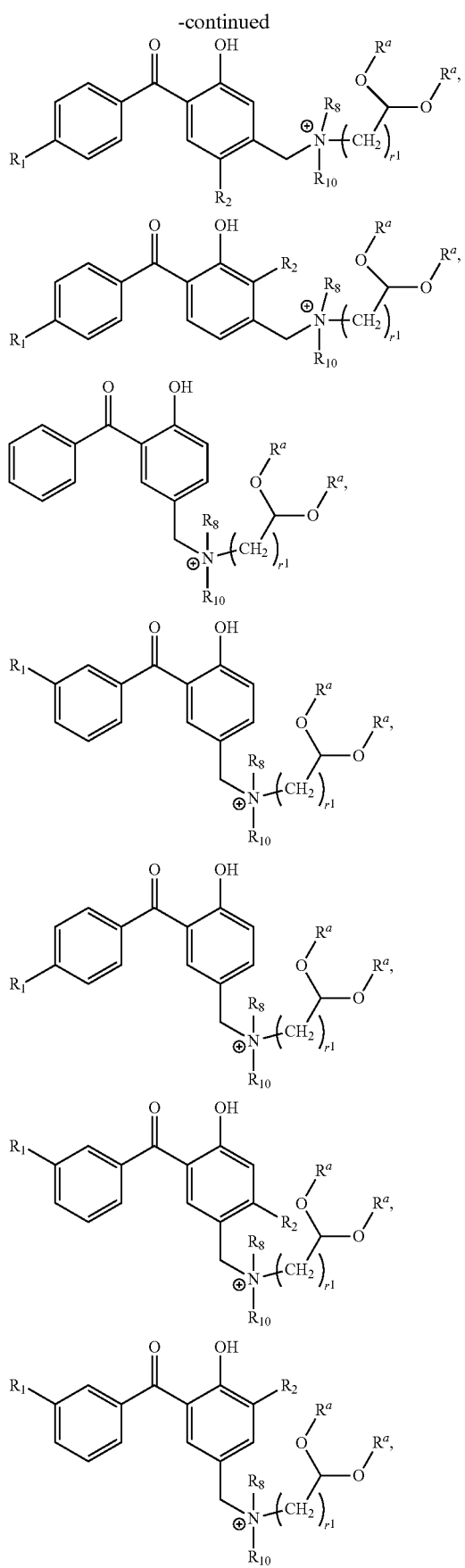
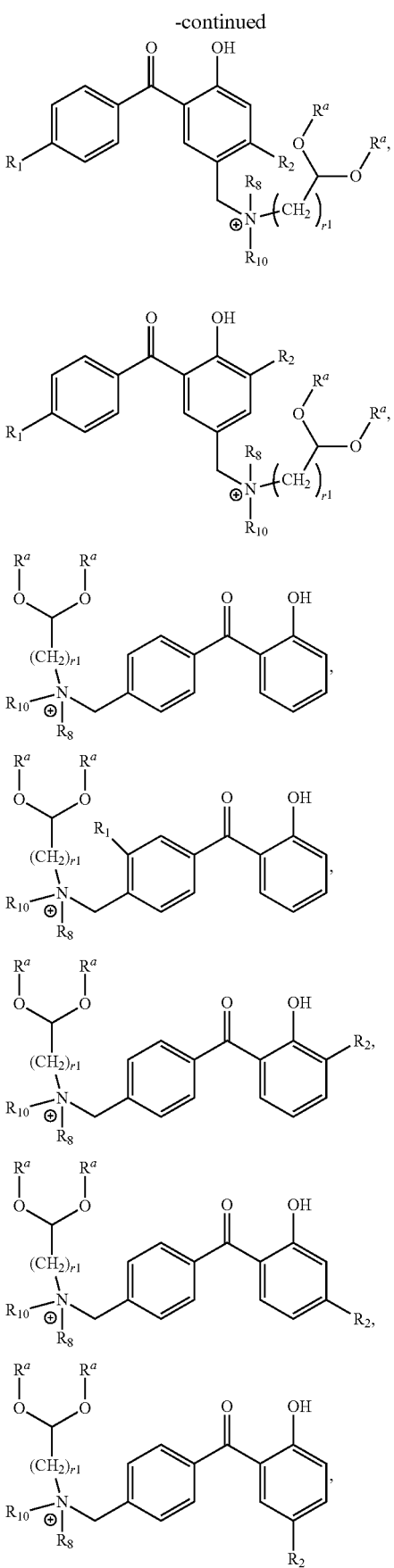

-continued

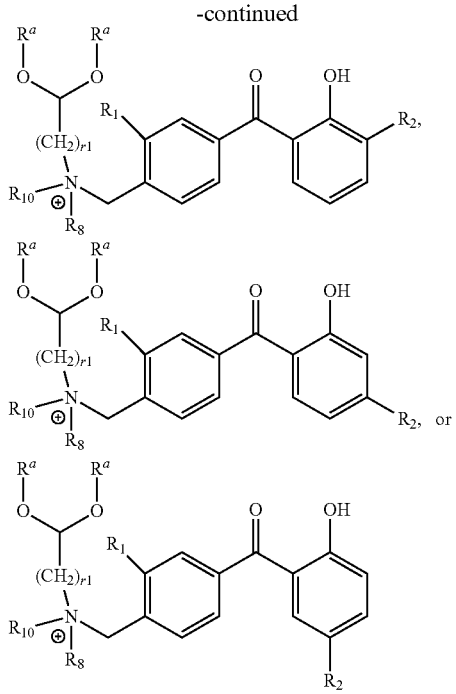

in which: $R^a$ is methyl or ethyl; $R_1$ and R2 independent of each other are $CH_3$, $CCl_3$, $CF_3$, Cl, Br, NR'R" OH, or $OCH_3$; in which R' and R" independent of each other are H or $C_1$-$C_4$ alkyl; $R_8$ is $CH_3$, $C_2H_5$,

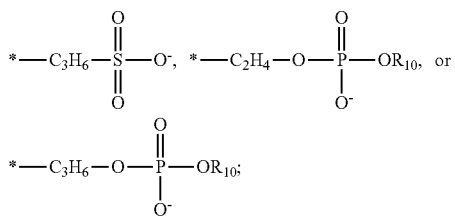

$R10$ is methyl or ethyl; and r1 is an integer of 3 to 6.

10. The acetal-containing, UV-absorbing compound of claim 5, wherein the acetal-containing, UV-absorbing compound is further defined by

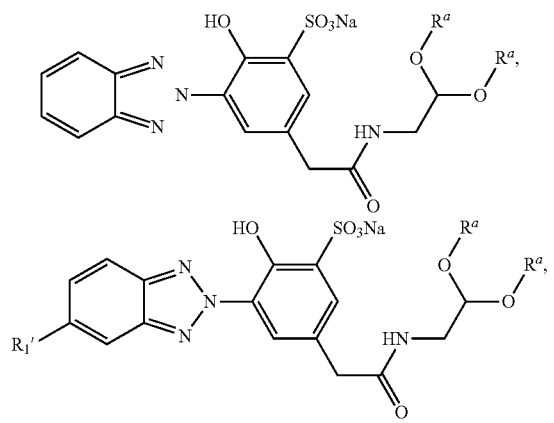

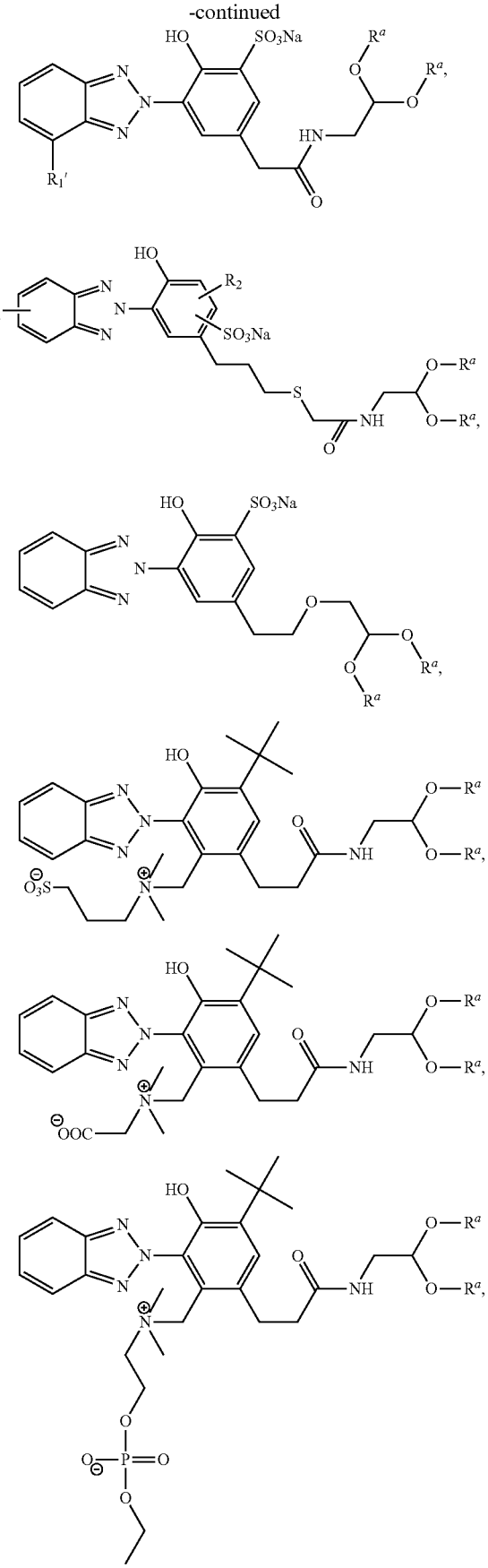

-continued
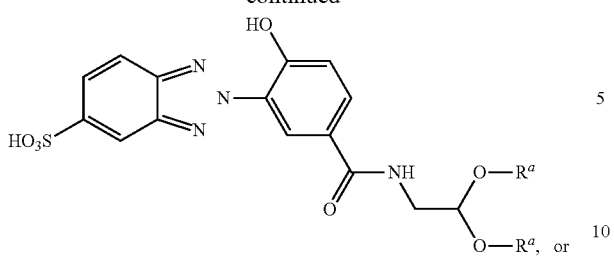
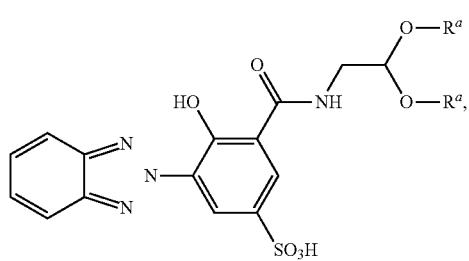
in which $R^a$ is methyl or ethyl; $R^o$ is H or $CH_3$; $R_1$ and $R_2$ independent of each other are H, $CH_3$, $CCl_3$, $CF_3$, Cl, Br, NR'R" in which R' and R" independent of each other are H or $C_1$-$C_4$ alkyl, OH, or $OCH_3$.
11. The acetal-containing, UV-absorbing compound of claim 6, wherein the acetal-containing, UV-absorbing compound is further defined by
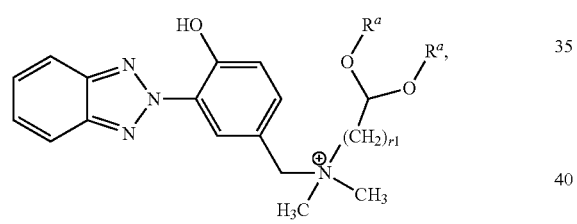
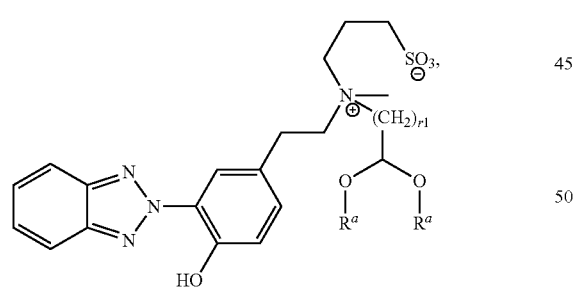
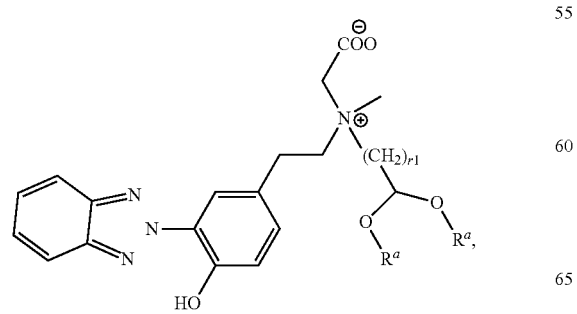
-continued
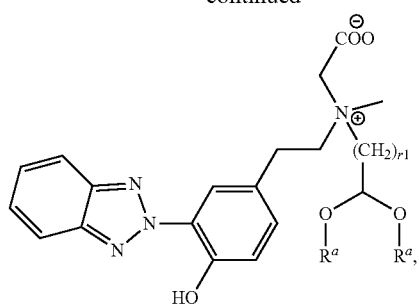
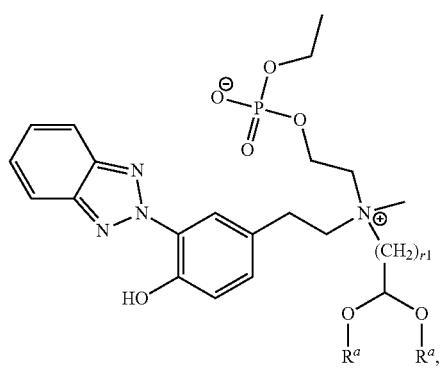
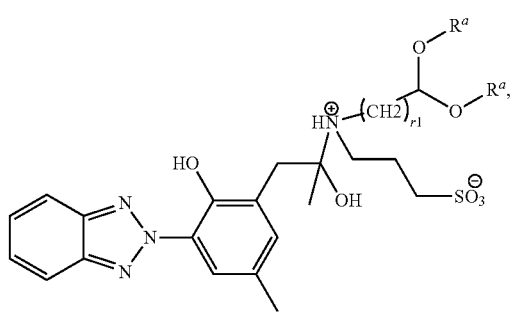
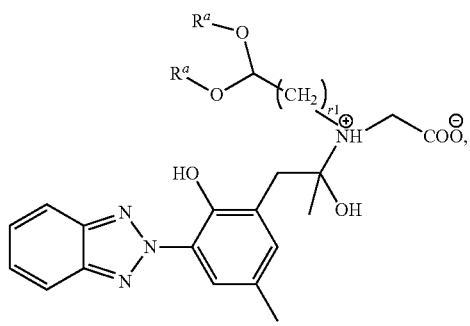
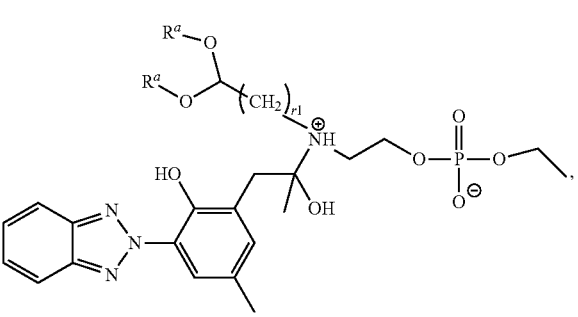

-continued
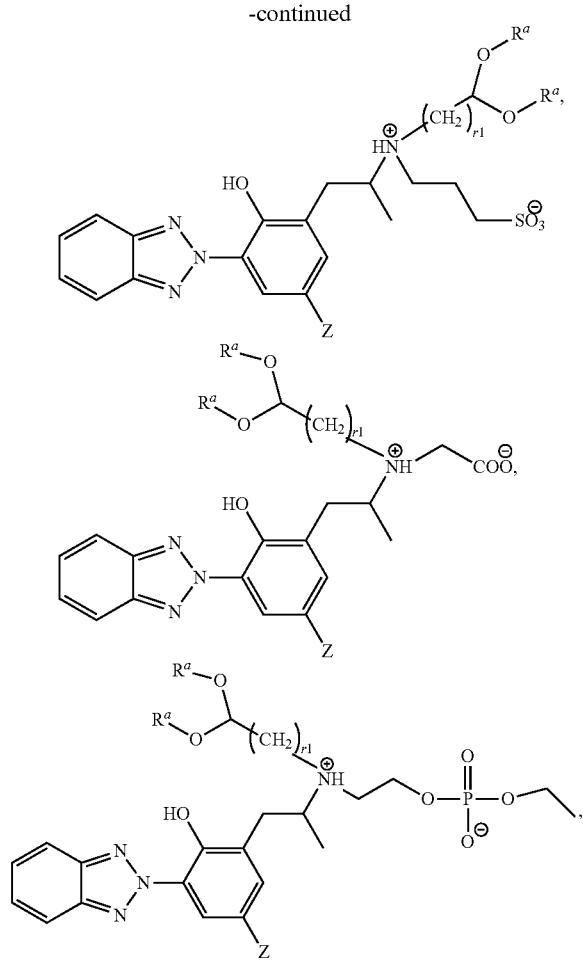
-continued
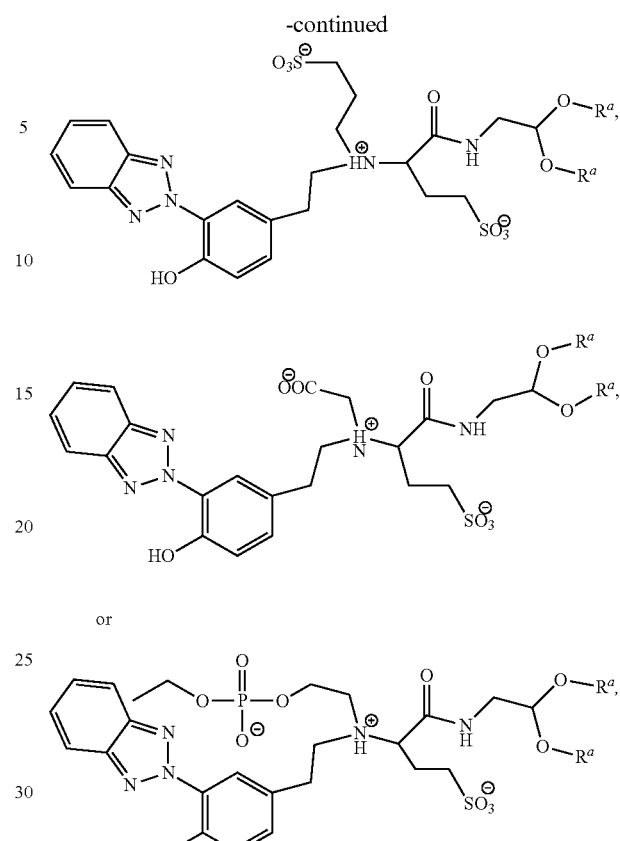
in which $R^a$ is methyl or ethyl, r1 is an integer of 3 to 6, and $Z=CH_3$ or COOH.
* * * * *